United States Patent
Gotoh et al.

(10) Patent No.: US 9,637,578 B2
(45) Date of Patent: May 2, 2017

(54) POLYMERIZABLE COMPOUND, POLYMERIZABLE COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Yasuyuki Gotoh, Ichihara (JP); Kenji Hirata, Ichihara (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/823,779

(22) Filed: Aug. 11, 2015

(65) Prior Publication Data
US 2016/0046744 A1 Feb. 18, 2016

(30) Foreign Application Priority Data
Aug. 11, 2014 (JP) ................. 2014-163623

(51) Int. Cl.
| | | |
|---|---|---|
| *C08F 122/20* | (2006.01) | |
| *C07C 69/54* | (2006.01) | |
| *C07C 69/653* | (2006.01) | |
| *C07C 69/73* | (2006.01) | |
| *C07C 69/82* | (2006.01) | |
| *C07C 69/86* | (2006.01) | |
| *C09K 19/38* | (2006.01) | |
| *C09K 19/34* | (2006.01) | |
| *C08F 122/18* | (2006.01) | |
| *C09K 19/04* | (2006.01) | |
| *C08F 122/10* | (2006.01) | |
| *C09K 19/30* | (2006.01) | |
| *C09K 19/18* | (2006.01) | |

(52) U.S. Cl.
CPC ............ *C08F 122/20* (2013.01); *C07C 69/54* (2013.01); *C07C 69/653* (2013.01); *C07C 69/73* (2013.01); *C07C 69/82* (2013.01); *C07C 69/86* (2013.01); *C08F 122/10* (2013.01); *C08F 122/18* (2013.01); *C09K 19/04* (2013.01); *C09K 19/3458* (2013.01); *C07C 2101/14* (2013.01); *C07C 2103/24* (2013.01); *C07C 2103/26* (2013.01); *C09K 2019/0448* (2013.01); *C09K 2019/181* (2013.01); *C09K 2019/301* (2013.01); *C09K 2019/3004* (2013.01); *C09K 2019/308* (2013.01); *C09K 2019/3009* (2013.01); *C09K 2019/3016* (2013.01); *C09K 2019/3021* (2013.01); *C09K 2019/3025* (2013.01); *C09K 2019/3071* (2013.01); *C09K 2019/3077* (2013.01); *C09K 2019/3083* (2013.01); *C09K 2019/3422* (2013.01)

(58) Field of Classification Search
CPC ....... C07C 69/01; C07C 69/007; C07C 69/54; C07C 69/587; C07C 69/602; C07C 69/734; C07C 69/736; C07C 43/14; C07C 43/164; C07C 43/166; C07C 43/215; C08F 136/22; C08F 112/32; C08F 36/02; C08F 36/04; C08F 236/04; C08F 122/20; C08F 265/06
USPC .......... 560/95, 201, 205, 224, 225; 526/327; 568/654, 687
See application file for complete search history.

(56) References Cited

U.S. PATENT DOCUMENTS

| | | |
|---|---|---|
| 2001/0006410 A1 | 7/2001 | Yamada et al. |
| 2004/0011996 A1 | 1/2004 | Klasen-Memmer et al. |
| 2005/0116200 A1 | 6/2005 | Nakanishi et al. |
| 2010/0309423 A1 | 12/2010 | Bernatz et al. |
| 2012/0056129 A1* | 3/2012 | Hasebe ..................... C08F 2/48 252/299.5 |
| 2013/0134354 A1 | 5/2013 | Gotoh et al. |

(Continued)

FOREIGN PATENT DOCUMENTS

| | | |
|---|---|---|
| CN | 101671252 A | 8/2015 |
| EP | 1889894 A | 2/2008 |
| JP | H10186330 A | 7/1998 |

(Continued)

*Primary Examiner* — Cynthia H Kelly
*Assistant Examiner* — Anna Malloy
(74) *Attorney, Agent, or Firm* — Hogan Lovells US LLP

(57) ABSTRACT

A polymerizable compound is provided having suitable polymerization reactivity, high conversion and high compatibility in a liquid crystal composition, a polymerizable composition containing the compound, a liquid crystal composite prepared using the composition, and a liquid crystal display device having the composite. The polymerizable compound has at least one monovalent group (A). The polymerizable composition contains the compound. The liquid crystal composition and the liquid crystal composite is prepared using the polymerizable composition. The liquid crystal display device has the liquid crystal composite.

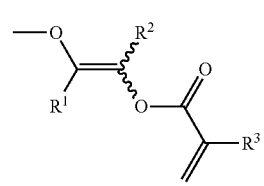

(A)

In the monovalent group (A), $R^1$ and $R^2$ are independently alkyl having 1 to 3 carbons, and in the alkyl, at least one of hydrogen may be replaced by fluorine, and $R^3$ is hydrogen or methyl.

10 Claims, No Drawings

(56) References Cited

U.S. PATENT DOCUMENTS

2014/0008572 A1    1/2014    Gotoh et al.

FOREIGN PATENT DOCUMENTS

| JP | 2003307720 A | 10/2003 |
| JP | 2004131704 A | 4/2004 |
| JP | 2006133619 A | 5/2006 |
| JP | 2010537256 A | 12/2012 |
| WO | 2013077343 A1 | 5/2013 |
| WO | 2014006962 A1 | 1/2014 |

* cited by examiner

POLYMERIZABLE COMPOUND, POLYMERIZABLE COMPOSITION AND LIQUID CRYSTAL DISPLAY DEVICE

TECHNICAL FIELD

The invention relates to a polymerizable compound, a polymerizable composition containing the polymerizable compound and a liquid crystal composition, a liquid crystal composite prepared from the polymerizable composition, and a liquid crystal display device.

BACKGROUND ART

A liquid crystal display device utilizes optical anisotropy, dielectric anisotropy and so forth of liquid crystal molecules in a liquid crystal composition. A classification based on an operating mode of the liquid crystal molecules includes a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a fringe field switching (FFS) mode and a vertical alignment (VA) mode.

A liquid crystal display device having a mode in which a polymer is combined with the liquid crystal composition is known. Examples of such a mode include a polymer sustained alignment (PSA) mode or a polymer stabilized (PS) mode. In the liquid crystal display device having the mode, the liquid crystal composition to which a polymerizable compound is added is injected into a display device. The display device is irradiated with ultraviolet light in a state of applying voltage between electrodes to polymerize the polymerizable compound to form the polymer in the liquid crystal composition. According to the method, a liquid crystal display device, in which a response time is shortened and image persistence is improved, is obtained.

The method can be applied to liquid crystal display devices having various operating modes, and such modes are known as a PS-TN mode, a PS-IPS mode, a PS-FFS mode, a PSA-VA mode and a PSA-OCB mode. The polymerizable compound to be used in the device having such a mode is considered to have high capability for aligning the liquid crystal molecules, but compatibility in the liquid crystal composition is far from high. An attempt has been so far made on improving the compatibility in the liquid crystal composition, but as the compatibility is improved, polymerization reactivity tends to decrease. Therefore, development has been desired for a polymerizable compound having a suitable balance between the compatibility and the polymerization reactivity.

CITATION LIST

Patent Literature

Patent literature No. 1: JP 2003-307720 A.
Patent literature No. 2: JP 2004-131704 A.
Patent literature No. 3: JP 2006-133619 A.
Patent literature No. 4: JP 2010-537256 A.
Patent literature No. 5: JP H10-186330 A.
Patent literature No. 6: EP 1889894 A.
Patent literature No. 7: CN 101671252 A.
Patent literature No. 8: WO 2013/77343 A.
Patent literature No. 9: WO 2014/6962 A.

SUMMARY OF INVENTION

Technical Problem

A first object of the invention is to provide a polymerizable compound having suitable polymerization reactivity, high conversion and high compatibility in a liquid crystal composition. A second object is to provide a liquid crystal composite satisfying at least one of physical properties such as a high maximum temperature of a nematic phase, a low minimum temperature of the nematic phase, a small viscosity, a suitable optical anisotropy, a large dielectric anisotropy, a suitable elastic constant, a large specific resistance and a suitable pretilt. The object is to provide a liquid crystal composite having a suitable balance regarding at least two of the physical properties. A third object is to provide a liquid crystal display device having a wide temperature range in which the devise can be used, a short response time, a high voltage holding ratio, a low threshold voltage, a large contrast ratio and a long service life.

Solution to Problem

The invention concerns a polymerizable compound having at least one monovalent group represented by formula (A), a polymerizable composition containing the compound and a liquid crystal composition, a liquid crystal composite prepared from the polymerizable composition, and a liquid crystal display device having the liquid crystal composite:

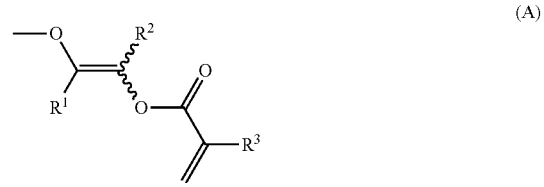

(A)

wherein, in formula (A), $R^1$ and $R^2$ are independently alkyl having 1 to 3 carbons, and in the alkyl, at least one of hydrogen may be replaced by fluorine, and $R^3$ is hydrogen or methyl.

The invention further concerns an optically anisotropic body, formed by polymerization of the polymerizable composition.

Advantageous Effects of Invention

A first advantage of the invention is a polymerizable compound having a suitable polymerization reactivity, high conversion and a high compatibility in a liquid crystal composition. A second advantage is a liquid crystal composite satisfying at least one of physical properties such as a high maximum temperature of a nematic phase, a low minimum temperature of the nematic phase, a small viscosity, a suitable optical anisotropy, a large dielectric anisotropy, a suitable elastic constant, a large specific resistance and a suitable pretilt. The advantage is the liquid crystal composite having a suitable balance regarding at least two of the physical properties. A third advantage is a liquid crystal display device having a wide temperature range in which the device can be used, a short response time, a high voltage holding ratio, a low threshold voltage, a large contrast ratio and a long service life.

DESCRIPTION OF EMBODIMENTS

Usage of terms herein is described below. "Liquid crystal compound" is a generic term for a non-polymerizable compound having a liquid crystal phase such as a nematic phase and a smectic phase, and a non-polymerizable compound having no liquid crystal phase but being mixed for the purpose of adjusting physical properties of a liquid crystal composition, such as a maximum temperature, a minimum temperature, viscosity and dielectric anisotropy. The compound has a 6-membered ring such as 1,4-cyclohexylene and 1,4-phenylene, and has rod like molecular structure. "Liquid crystal composition" is a mixture of the liquid crystal compounds. "Polymerizable compound" is a compound which is added to a composition for forming polymers in the composition. "Polymerizable composition" is a mixture of the polymerizable compound, the liquid crystal composition and additives. "Liquid crystal composite" includes a composite to be formed by polymerization of the polymerizable composition. "Liquid crystal display device" is a generic term for a liquid crystal display panel and a liquid crystal display module. "Maximum temperature of the nematic phase" is a phase transition temperature between the nematic phase and an isotropic phase in the liquid crystal composition, the polymerizable composition or the liquid crystal composite, and may be occasionally abbreviated as "maximum temperature." "Minimum temperature of the nematic phase" may be abbreviated as "minimum temperature." "Polymerization reactivity" means a degree of ease when a reactant is polymerized. "Conversion" means a weight ratio of a reactant consumed by a chemical reaction to a total reactant.

The liquid crystal composition is prepared by mixing the liquid crystal compounds. A ratio (content) of the liquid crystal compounds is expressed in terms of weight percent (% by weight) based on the weight of the liquid crystal composition. An additive such as an optically active compound, an antioxidant, an ultraviolet light absorber, a light stabilizer, a heat stabilizer, an antifoaming agent, a polymerizable compound, a polymerization initiator and a polymerization inhibitor is added to the composition, when necessary. A ratio (amount of addition) of the additive is expressed in weight percent (% by weight) based on the weight of the liquid crystal composition in a manner which is similar to the ratio of the liquid crystal compounds. Weight parts per million (ppm) is occasionally used. Except definitions described above, A ratio of the polymerization initiator and the polymerization inhibitor is expressed based on the weight of the polymerizable compound.

A compound represented by formula (1) is occasionally abbreviated as compound (1). At least one compound selected from the group of compounds represented by formula (1) is occasionally abbreviated as "compound (1)." "Compound (1)" means one compound, a mixture of two compounds or a mixture of three or more compounds, represented by formula (1). A same rule also applies to a compound represented by any other formula. In ring A1 of compound (1), a line crossing a circle means that a bonding position of P1-S1 group can be arbitrarily selected from the positions of ring such as a six-membered ring and a condensed ring. A same rule also applies to a symbol such as a $P^2$—$S^2$ group. In formulas (2) to (8), Hexagons surrounded by B1, C1 or D1 or the like are corresponded as ring B1, ring C1 and ring D1 respectively. A symbol of $R^{11}$ is used for a plurality of formulas such as formula (2) and formula (3). In the compounds, two terminal groups represented by two of arbitrary $R^{11}$ may be identical or different. In formula (8), when i is 2, two of $D^1$ exists in one formula. In the compound, two rings represented by two of $D^1$ may be identical or different. The same rule also applies to D When j is larger than 2. The same rule also applies to any other symbol such as the $P^1$—$S^1$ group.

An expression "at least one of "A" may be replaced by "B"" means that a position of "A" when the number of "A" is 1 is arbitrary, and the positions thereof also when the number of "A" is 2 or more can be selected without limitation. An expression "at least one of A may be replaced by B, C or D" means inclusion of a case where arbitrary A is replaced by B, a case where arbitrary A is replaced by C, a case where arbitrary A is replaced by D, and further a case where a plurality of A are replaced by at least two of B, C and D. For example, alkyl in which at least one of —CH2— may be replaced by —O— or —CH═CH— includes alkyl, alkenyl, alkoxy, alkoxyalkyl, alkoxyalkenyl and alkenyloxyalkyl. In addition, a case where replacement of two successive —CH2- by —O— results in forming —O—O— is not preferred. In alkyl or the like, a case where replacement of —CH2- of a methyl part (—CH2-H) by —O— results in forming —O—H is not preferred, either.

Then, 2-fluoro-1,4-phenylene means two divalent groups described below. In a chemical formula, fluorine may be leftward (L) or rightward (R). The same rule also applies to an asymmetrical divalent group derived from a ring such as tetrahydropyran-2,5-diyl.

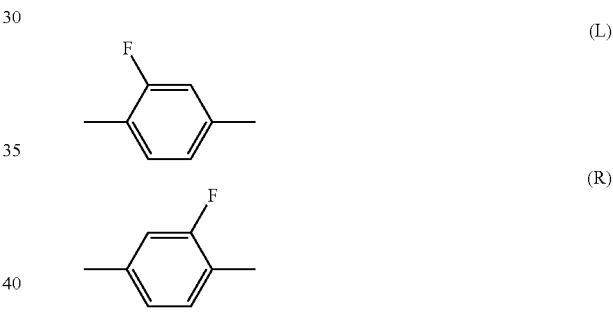

Halogen means fluorine, chlorine, bromine and iodine. Preferred halogen is fluorine or chlorine, further preferred halogen is fluorine.

The invention includes the content as described in items below.

Item 1. A polymerizable compound having at least one monovalent group represented by formula (A):

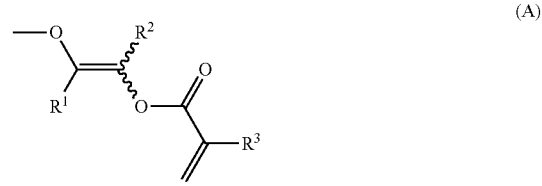

wherein, in formula (A), $R^1$ and $R^2$ are independently alkyl having 1 to 3 carbons, and in the alkyl, at least one of hydrogen may be replaced by fluorine, and $R^3$ is hydrogen or methyl.

Item 2. The polymerizable compound according to item 1, represented by formula (1):

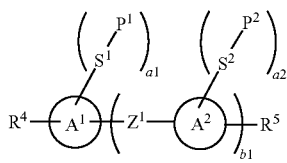

wherein, in formula (1),

P¹ and P² are independently a polymerizable group;

S¹ and S² are independently a single bond or alkylene having 1 to 10 carbons, and in the alkylene, at least one of —CH$_2$— may be replaced by —O—, —CO—, —COO— or —OCO—, at least one of —CH$_2$—CH$_2$— may be replaced by —CH═CH— or —C≡C—, and in the divalent groups, at least one of hydrogen may be replaced by halogen or alkyl having 1 to 3 carbons;

R⁴ is hydrogen or —S¹—P¹, and R⁵ is hydrogen or —S²—P²;

a1 and a2 are independently 0, 1, 2, 3 or 4;

a total of —S¹—P¹ and —S²—P² is 2 to 8, and at least one of all of —S¹—P¹ and all of —S²—P² is a monovalent group represented by formula (A):

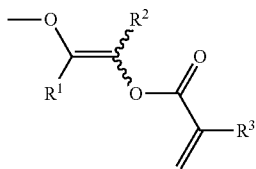

wherein, in formula (A), R¹ and R² are independently alkyl having 1 to 3 carbons, and R³ is hydrogen or methyl;

in formula (1), ring A¹ and ring A² are independently a divalent group derived from alicyclic hydrocarbon having 3 to 18 carbons, aromatic hydrocarbon having 6 to 18 carbons or heteroaromatic hydrocarbon having 3 to 18 carbons, in the divalent groups, at least one of hydrogen may be replaced by halogen, alkyl having 1 to 12 carbons, alkoxy having 1 to 12 carbons, alkenyl having 1 to 12 carbons or alkenyloxy having 1 to 12 carbons, and in the monovalent hydrocarbon groups, at least one of hydrogen may be replaced by halogen;

Z¹ is a single bond or alkylene having 1 to 10 carbons, in the alkylene, at least one of —CH$_2$— may be replaced by —O—, —CO—, —COO— or —OCO—, at least one of —CH$_2$—CH$_2$— may be replaced by —CH═CH—, —C(CH$_3$)═CH—, —CH═C(CH$_3$)—, —C(CH$_3$)═C(CH$_3$)— or —CH≡CH—, and in the divalent groups, at least one of hydrogen may be replaced by halogen;

b1 is 0, 1, 2 or 3.

Item 3. The polymerizable compound according to item 2, represented by formula (1), wherein, in formula (1), P¹ and P² are independently acryloyloxy or methacryloyloxy;

S¹ and S² are independently a single bond or alkylene having 1 to 4 carbons, in the alkylene, at least one of —CH$_2$— may be replaced by —O—, at least one of —CH$_2$—CH$_2$— may be replaced by —CH═CH— or —C≡C—, and in the divalent groups, at least one of hydrogen may be replaced by fluorine or alkyl having 1 to 3 carbons;

a1 and a2 are independently 0, 1, 2 or 3;

a total of —S¹—P¹ and —S²—P² is 2 to 6, and at least one of —S¹—P¹ and of —S²—P² is a monovalent group represented by formula (A):

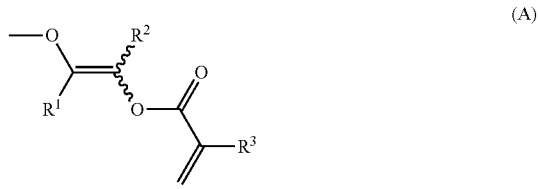

wherein, in formula (A), R¹ and R² are methyl, and R³ is hydrogen or methyl;

in formula (1), ring A¹ and ring A² are independently a divalent group derived from aromatic hydrocarbon having 6 to 18 carbons or heteroaromatic hydrocarbon having 3 to 18 carbons, in the divalent groups, at least one of hydrogen may be replaced by fluorine, chlorine, alkyl having 1 to 4 carbons, alkoxy having 1 to 4 carbons, alkenyl having 1 to 4 carbons or alkenyloxy having 1 to 4 carbons, and in the monovalent hydrocarbon groups, at least one of hydrogen may be replaced by fluorine or chlorine;

Z¹ is a single bond or alkylene having 1 to 4 carbons, in the alkylene, at least one of —CH$_2$— may be replaced by —O—, —CO—, —COO— or —OCO—, and at least one of —CH$_2$—CH$_2$— may be replaced by —CH═CH—, —C(CH$_3$)═CH—, —CH═C(CH$_3$)—, —C(CH$_3$)═C(CH$_3$)— or —CH≡CH—, and in the divalent groups, at least one of hydrogen may be replaced by fluorine or chlorine;

b1 is 0, 1 or 2.

Item 4. The polymerizable compound according to any one of items 1 to 3, represented by formula (1-1):

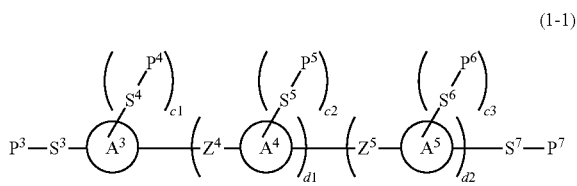

wherein, in formula (1-1),

P³, P⁴, P⁵, P⁶ and P⁷ are independently acryloyloxy or methacryloyloxy;

S³, S⁴, S⁵, S⁶ and S⁷ are independently a single bond or alkylene having 1 to 4 carbons, in the alkylene, at least one of —CH$_2$— may be replaced by —O—, at least one of —CH$_2$—CH$_2$— may be replaced by —CH═CH— or —C≡C—, and in the divalent groups, at least one of hydrogen may be replaced by fluorine, methyl or ethyl;

c1, c2 and c3 are independently 0, 1 or 2, and a sum of c1, c2 and c3 is 0, 1 or 2;

at least one of —S³—P³, of all of —S⁴—P⁴, all of —S⁵—P⁵, all of —S⁶—P⁶ and —S⁷—P⁷ is a monovalent group represented by formula (A):

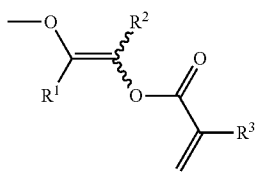

wherein, in formula (A), $R^1$ and $R^2$ are methyl, and $R^3$ is hydrogen or methyl;

in formula (1-1), ring $A^3$, ring $A^4$ and ring $A^5$ are independently 1,4-phenylene, naphthalene-1,4-diyl, naphthalene-1,5-diyl, naphthalene-2,6-diyl, fluorene-2,7-diyl or phenanthrene-2,7-diyl, and in the rings, at least one of hydrogen may be replaced by fluorine, alkyl having 1 to 3 carbons, and alkyl having 1 to 3 carbons in which at least one of hydrogen was replaced by fluorine or chlorine;

$Z^4$ and $Z^5$ are independently a single bond, alkylene having 1 to 4 carbons, —COO—, —OCO—, —CH$_2$O—, —OCH$_2$—, —CF$_2$O—, —OCF$_2$—, —CH=CH—, —CH=CH—COO—, —OCO—CH=CH—, —C(CH$_3$)=CH—COO—, —OCO—CH=C(CH$_3$)—, —CH=C(CH$_3$)—COO—, —OCO—(CH$_3$)C=CH—, —C(CH$_3$)=C(CH$_3$)—COO—, —OCO—C(CH$_3$)=C(CH$_3$)—, —CO—CH=CH—, —CH=CH—CO—, —C(CH$_3$)=C(CH$_3$)—, —CH=CH—CH$_2$O—, —OCH$_2$—CH=CH—, —CH=CH—OCH$_2$—, —CH$_2$O—CH=CH— or —CH≡CH—;

d1 and d2 are independently 0 or 1.

Item 5. The polymerizable compound according to item 4, represented by formula (1-1), wherein, in formula (1-1) described in item 4, $P^3$, $P^4$, $P^5$, $P^6$ and $P^7$ are independently acryloyloxy or methacryloyloxy;

$S^3$, $S^4$, $S^5$, $S^6$ and $S^7$ are independently a single bond or —OC(CH$_3$)=C(CH$_3$);

c1, c2 and c3 are independently 0, 1 or 2, and a sum of c1, c2 and c3 is 0, 1 or 2;

at least one of —S$^3$—P$^3$, of all of —S$^4$—P$^4$, all of —S$^5$—P$^5$, all of —S$^6$—P$^6$ and —S$^7$—P$^7$ is a monovalent group represented by formula (A):

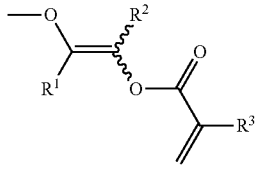

wherein, in formula (A), $R^1$ and $R^2$ are methyl, and $R^3$ is hydrogen or methyl;

in formula (1-1), ring $A^3$, ring $A^4$ and ring $A^5$ are independently 1,4-phenylene, naphthalene-1,4-diyl, naphthalene-1,5-diyl, naphthalene-2,6-diyl, fluorene-2,7-diyl or phenanthrene-2,7-diyl, and in the rings, at least one of hydrogen may be replaced by fluorine, methyl or trifluoromethyl;

$Z^4$ and $Z^5$ are independently a single bond, ethylene, —COO—, —OCO—, —CH=CH—, —CH=CH—COO—, —OCO—CH=CH— or —CH≡CH—;

d1 and d2 are independently 0 or 1.

Item 6. The polymerizable compound according to item 5, represented by formulas (1-1-1) to (1-1-3):

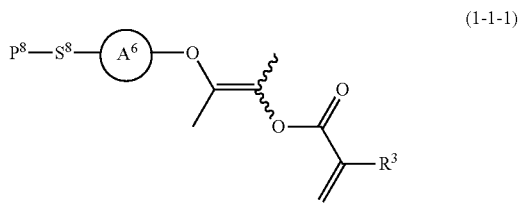

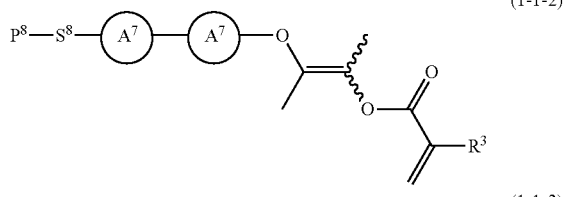

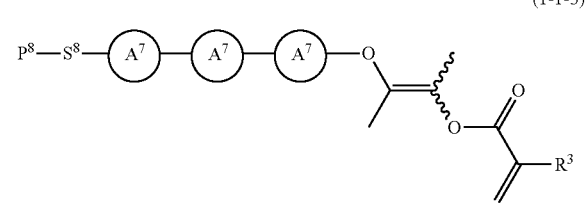

wherein, in formulas (1-1-1) to (1-1-3), $P^8$ is acryloyloxy or methacryloyloxy; $S^8$ is a single bond or —OC(CH$_3$)=C(CH$_3$)—; ring $A^6$ is naphthalene-1,4-diyl, naphthalene-2,6-diyl, fluorene-2,7-diyl or phenanthrene-2,7-diyl; ring $A^7$ is 1,4-phenylene in which at least one of hydrogen may be replaced by fluorine or methyl, naphthalene-1,4-diyl or naphthalene-2,6-diyl; and $R^3$ is hydrogen or methyl.

Item 7. A polymerizable composition, containing at least one polymerizable compound according to any one of items 1 to 6.

Item 8. The polymerizable composition according to item 7, further containing at least one compound selected from the group of compounds represented by formulas (2) to (4):

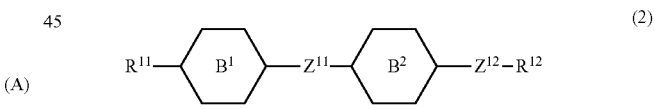

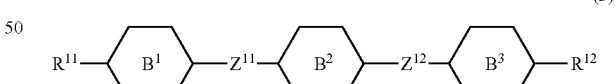

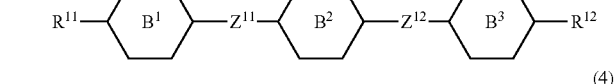

wherein, in formulas (2) to (4), $R^{11}$ and $R^{12}$ are independently alkyl having 1 to 10 carbons or alkenyl having 2 to 10 carbons, and in the alkyl or the alkenyl, at least one of —CH$_2$— may be replaced by —O—, and at least one of hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl;

$Z^{11}$, $Z^{12}$ and $Z^{13}$ are independently a single bond, —CH$_2$CH$_2$—, —CH═CH—, or —COO—.

Item 9. The polymerizable composition according to item 7 or 8, further containing at least one compound selected from the group of compounds represented by formulas (5) to (7):

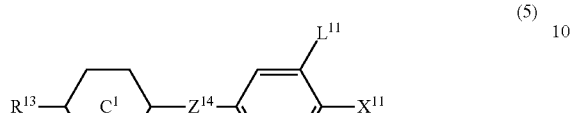
(5)

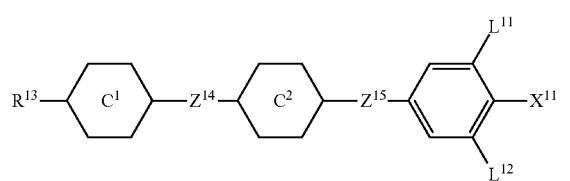
(6)

(7)

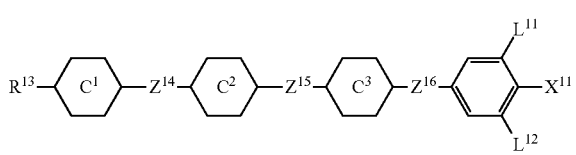

wherein, in formulas (5) to (7), $R^{13}$ is alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine;

$X^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;

ring $C^1$, ring $C^2$ and ring $C^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —CH$_2$CH$_2$—, —CH═CH—, —COO—, —CF$_2$O—, —OCF$_2$—, —CH$_2$O— or —(CH$_2$)$_4$—;

$L^{11}$ and $L^{12}$ are independently hydrogen or fluorine.

Item 10. The polymerizable composition according to any one of items 7 to 9, further containing at least one compound selected from the group of compounds represented by formula (8):

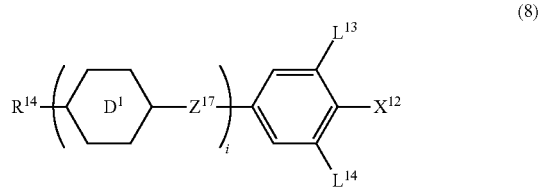
(8)

wherein, in formula (8), $R^{14}$ is alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine;

$X^{12}$ is —C≡N or —C═C—C≡N;

ring $D^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{17}$ is a single bond, —CH$_2$CH$_2$—, —COO—, —CF$_2$O—, —OCF$_2$— or —CH$_2$O—;

$L^{13}$ and $L^{14}$ are independently hydrogen or fluorine;

i is 1, 2, 3 or 4.

Item 11. A liquid crystal composite, formed by polymerization of the polymerizable composition according to any one of items 7 to 10.

Item 12. An optically anisotropic body, formed by polymerization of the polymerizable composition according to any one of items 7 to 10.

Item 13. A liquid crystal display device, composed of the polymerizable composition according to any one of items 7 to 10 or the liquid crystal composite according to item 11.

Item 14. Use of at least one selected from the group of the compound according to any one of items 1 to 6, the polymerizable composition according to any one of items 7 to 10, and the liquid crystal composite according to item 11 in a liquid crystal display device.

The invention further includes the following items: (a) the polymerizable composition, further containing at least one of additives such as the optically active compound, the antioxidant, the ultraviolet light absorber, the light stabilizer, the heat stabilizer, the antifoaming agent, the polymerization initiator and the polymerization inhibitor; (b) the polymerizable composition, further containing at least one polymerization initiator; (c) the polymerizable composition, further containing a polymerizable compound having no monovalent group represented by formula (A); (d) use of compound (1) in a polymerizable composition adapted for a liquid crystal display device having a PSA mode; (e) use of compound (1) in the liquid crystal display device having the PSA mode; (f) use of at least one compound selected from the group of compounds represented by formulas (1), (1-1) and (1-1-1) to (1-1-3) in the liquid crystal display device having the PSA mode; (g) use of the polymerizable composition containing at least one compound described above in the liquid crystal display device having the PSA mode; (h) use of a liquid crystal composite formed by polymerization of the polymerizable composition in the liquid crystal display device having the PSA mode; and (i) use of the compound, the polymerizable composition, or the liquid crystal composite in the liquid crystal display device having a mode such as PS-TN, PS-IPS, PS-FFS, PSA-VA or PSA-OCB.

The invention further includes the following items: (j) use of a composition, containing a compound represented by formula (1), and at least one compound selected from the group of compounds represented by formulas (2), (3) and (4) in the liquid crystal display device having the PSA mode; (k) use of a composition, containing a compound represented by formula (1), and at least one compound selected from the group of compounds represented by formulas (5), (6) and (7) in the liquid crystal display device having the PSA mode; and (l) use of a composition, containing a compound represented by formula (1), and at least one compound selected from the group of compounds represented by formula (8) in the liquid crystal display device having the PSA mode.

The polymerizable compound of the invention will be first described, and then, In the order of synthesis method, the polymerizable composition, a liquid crystal composite and the liquid crystal display device, we will describe them.

1. Polymerizable Compound

The polymerizable compound of the invention has at least one monovalent group (A).

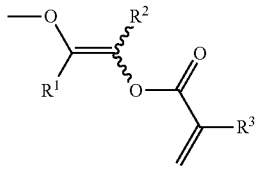
(A)

In monovalent group (A), $R^1$ and $R^2$ are independently alkyl having 1 to 3 carbons, and in the alkyl, at least one of hydrogen may be replaced by fluorine, and $R^3$ is hydrogen or methyl.

A preferred polymerizable compound is compound (1), and has a feature of having monovalent group (A). A configuration of monovalent group (A) has E-form and Z-form as shown below. The configuration of monovalent group (A) may be in E-form or Z-form. In preparing compound (1), compound (1) may be obtained as a mixture of E-form and Z-form. Both E-form and Z-form of compound (1) are preferred. In monovalent group (A), a wave line from a carbon of a double bond represents E-form or Z-form of monovalent group (A), or a mixture of the both.

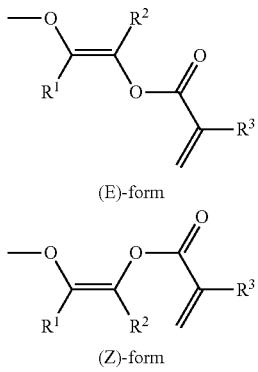

First, compound (1) has a rod like molecular structure similar to the structure of the liquid crystal compound, and therefore compound (1) has a high compatibility in the liquid crystal composition. Accordingly, compound (1) is suitable as a polymerizable compound required for the device having the PSA mode. Second, compound (1) has suitable polymerizability. Accordingly, compound (1) can be stably stored. Upon polymerization, a rate of photoreaction can be easily controlled. When its polymerization, velocity of photochemical reaction thereof is easily controlled. It is able to polymerize them by irradiating suitable quantity of ultraviolet light. Excess of the ultraviolet light is not required. Third, in compound (1), both E-form and Z-form is existed, and it is able to use only E-form. It is also able to use only Z-form. It is also able to use mixture of the both.

In compound (1), preferred examples of each of polymerizable group P, connecting group S, ring A and bonding group Z are as described below. The examples also apply to a subordinate compound of compound (1). In compound (1), the physical properties can be arbitrarily adjusted by suitably combining kinds of the groups. Amount higher than natural abundance of isotope such as $^2H$ (deuterium) and $^{13}C$ of compound (1) is acceptable since significant difference is shown in the physical properties of the compound.

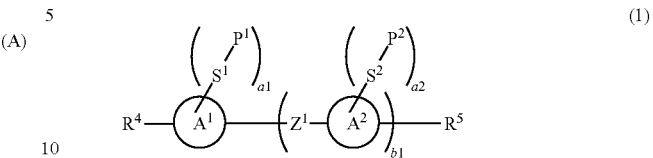
(1)

In formula (1), $P^1$ and $P^2$ are independently polymerizable groups. Examples of the polymerizable group include acryloyloxy, methacryloyloxy, acrylamide, methacrylamide, vinyloxy, vinylcarbonyl, oxiranyl, oxetanyl, 3,4-epoxycyclohexyl or maleimide. In the groups, at least one of hydrogen may be replaced by fluorine, methyl or trifluoromethyl. Preferred example of the polymerizable group include acryloyloxy (P-1), vinyloxy (P-2) or oxiranyl (P-3), in which $M^1$ and $M^2$ are independently hydrogen, fluorine, methyl or trifluoromethyl. Further preferred example is acryloyloxy (P-1). Particularly preferred example is acryloyloxy (—OCO—CH=$CH_2$) or methacryloyloxy (—OCO—($CH_3$)C=$CH_2$).

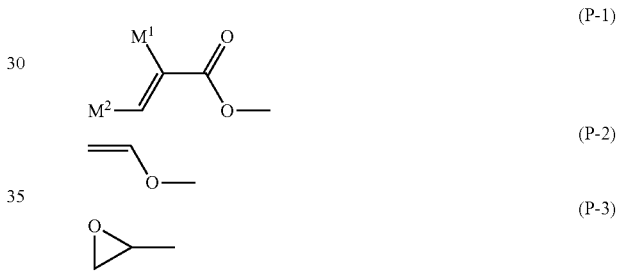

In formula (1), $S^1$ and $S^2$ are independently a single bond or alkylene having 1 to 10 carbons, in the alkylene, at least one of —$CH_2$— may be replaced by —O—, —CO—, —COO— or —OCO—, at least one of —$CH_2$—$CH_2$— may be replaced by —CH=CH— or and in the divalent groups, at least one of hydrogen may be replaced by halogen or alkyl having 1 to 3 carbons.

Preferred examples of $S^1$ or $S^2$ include a single bond, —$CH_2$—, —$CH_2$O—, —O$CH_2$—, —COO—, —OCO—, —$CH_2CH_2$—, —CH=CH—, —$(CH_2)_3$—, —$CH_2CH_2$O—, —O$CH_2CH_2$—, —CH=CH—O—, —O—CH=CH—, —$(CH_2)_4$—, —$(CH_2)_3$—O—, —O—$(CH_2)_3$—, —$(CH_2)_4$—, —$(CH_2)_4$O— or —O$(CH_2)_4$—. Further preferred examples include a single bond, —$CH_2$—, —$CH_2$O—, —O$CH_2$—, —COO—, —OCO—, —CH=CH—, —$CH_2CH_2$O—, —O$CH_2CH_2$—, —CH=CH—O— or —O—CH=CH—. The particularly preferred examples include a single bond, —$CH_2$—, —CH=CH—, —CH=CH—O—, —O—CH=CH—, —$CH_2CH_2$O— or —O$CH_2CH_2$—. The most preferred examples include a single bond. Both cis-form and trans-form of configuration of a double bond of —CH=CH— is acceptable. Trans-form is preferred than cis-form.

In formula (1), $R^4$ is hydrogen or —$S^1$—$P^1$, and $R^5$ is hydrogen or —$S^2$—$P^2$. Then, a1 and a2 are independently 0, 1, 2, 3 or 4. A total of —$S^1$—$P^1$ and —$S^2$—$P^2$ is 2 to 8. Then, —$S^1$—$P^1$ or —$S^2$—$P^2$ is a monovalent group that participates in the polymerization. Th sum of the groups is 2 to 8.

The sum of the preferred examples include 2 to 6, and sum of further preferred examples include 2 or 3. Most preferred examples include 2.

In formula (1), at least one of —$S^1$—$P^1$ and —$S^2$—$P^2$ is a monovalent group represented by formula (A).

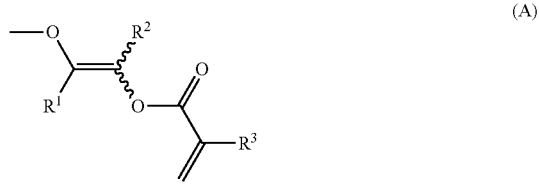

(A)

In formula (A), $R^1$ and $R^2$ are independently alkyl having 1 to 3 carbons, and $R^3$ is hydrogen or methyl. Preferred $R^1$ or $R^2$ is methyl or ethyl. Further preferred $R^1$ or $R^2$ is methyl. When both of a1 and a2 are 1, a compound is preferred in which —$S^1$—$P^1$ is monovalent group (A), and —$S^2$—$P^2$ is acryloyloxy or methacryloyloxy.

In formula (1), ring $A^1$ and ring $A^2$ are independently a divalent group derived by eliminating two of hydrogen from alicyclic hydrocarbon having 3 to 18 carbons, aromatic hydrocarbon having 6 to 18 carbons or heteroaromatic hydrocarbon having 3 to 18 carbons. In the divalent groups, at least one of hydrogen may be replaced by halogen, alkyl having 1 to 12 carbons, alkoxy having 1 to 12 carbons, alkenyl having 1 to 12 carbons or alkenyloxy having 1 to 12 carbons. In the monovalent hydrocarbon groups, at least one of hydrogen may be replaced by halogen.

Examples of the alicyclic hydrocarbon include cyclopropane, cyclobutane, cyclohexane, cycloheptane and cyclooctane, represented by $C_nH_{2n}$. Other examples include decahydronaphthalene. Specific examples of the aromatic hydrocarbon include benzene, naphthalene, anthracene, phenanthrene, fluorene, indan, indene and tetrahydronaphthalene. Specific examples of the heteroaromatic hydrocarbon include pyridine, pyrimidine, furan, pyran, thiophene and benzofuran. The hydrocarbons may be replaced by a monovalent group such as fluorine, chlorine and alkyl. Preferred examples of ring $A^1$ or ring $A^2$ include benzene, fluorobenzene, naphthalene, fluorene or phenanthrene. Further preferred examples include benzene or naphthalene.

In formula (1), $Z^1$ is a single bond or alkylene having 1 to 10 carbons, in the alkylene, at least one of —$CH_2$— may be replaced by —O—, —CO—, —COO— or —OCO—, at least one of —$CH_2$—$CH_2$— may be replaced by —CH═CH—, —C($CH_3$)═CH—, —CH═C($CH_3$)—, —C($CH_3$)═C($CH_3$)— or —C≡CH—, and in the divalent groups, at least one of hydrogen may be replaced by halogen.

Preferred examples of $Z^1$ include a single bond, alkylene having 1 to 4 carbons, —COO—, —OCO—, —$CH_2$O—, —O$CH_2$—, —$CF_2$O—, —O$CF_2$—, —CH═CH—, —CH═CH—COO—, —OCO—CH═CH—, —C($CH_3$)═CH—COO—, —OCO—CH═C($CH_3$)—, —CH═C($CH_3$)—COO—, —OCO—($CH_3$)C═CH—, —C($CH_3$)═C($CH_3$)—COO—, —OCO—C($CH_3$)═C($CH_3$)—, —CO—CH═CH—, —CH═CH—CO—, —C($CH_3$)═C($CH_3$)—, —CH═CH—$CH_2$O—, —O$CH_2$—CH═CH—, —CH═CH—O$CH_2$—, —$CH_2$O—CH═CH— or —CH≡CH—. Further preferred examples include a single bond, ethylene, —COO—, —OCO—, —CH═CH—, —CH═CH—COO—, —OCO—CH═CH— or —CH≡CH—. Most preferred examples include a single bond.

In formula (1), b1 is 0, 1, 2 or 3. When b1 is 0, the compound has one ring represented by ring $A^1$. In the above case, preferred ring $A^1$ is a divalent group derived by eliminating two of hydrogen from a condensed ring such as naphthalene, anthracene or phenanthrene. When b1 is 1, the compound has ring $A^1$ and ring $A^2$. In the above case, preferred ring $A^1$ or ring $A^2$ is a divalent group derived from benzene, or benzene in which hydrogen is replaced by a substituent such as fluorine or methyl. When b1 is 2, the compound has three rings of ring $A^1$, and ring $A^2$ and ring $A^2$. Preferred ring $A^1$ or ring $A^2$ is a divalent group derived from benzene, or benzene in which hydrogen is replaced by a substituent such as fluorine.

2. Synthesis Method

The synthesis method of compound (1) will be described. Compound (1) can be prepared by suitably combining methods in synthetic organic chemistry. A method for introducing an objective terminal group, ring and bonding group into a starting material is described in books such as Houben-Wyle, Methoden der Organische Chemie (Georg-Thieme Verlag, Stuttgart), Organic Syntheses (John Wily & Sons, Inc.), Organic Reactions (John Wily & Sons, Inc.), Comprehensive Organic Synthesis (Pergamon Press) and New Experimental Chemistry Course (Shin Jikken Kagaku Koza in Japanese) (Maruzen Co., Ltd.).

2-1. Formation of Bonding Group Z

An example of a method for forming bonding group Z in compound (1) is as described in a scheme below. In the scheme, $MSG^1$ (or $MSG^2$) is a monovalent organic group having at least one ring. Monovalent organic groups represented by a plurality of $MSG^1$ (or $MSG^2$) may be identical or different. Compounds (1A) to (1I) correspond to compound (1). In formation of ester, a method of synthesis of a compound having —COO— is shown. A compound having —OCO— can also be prepared by the synthesis method which is similar to the method. Other asymmetrical bonding groups can also be formed in the similar manner.

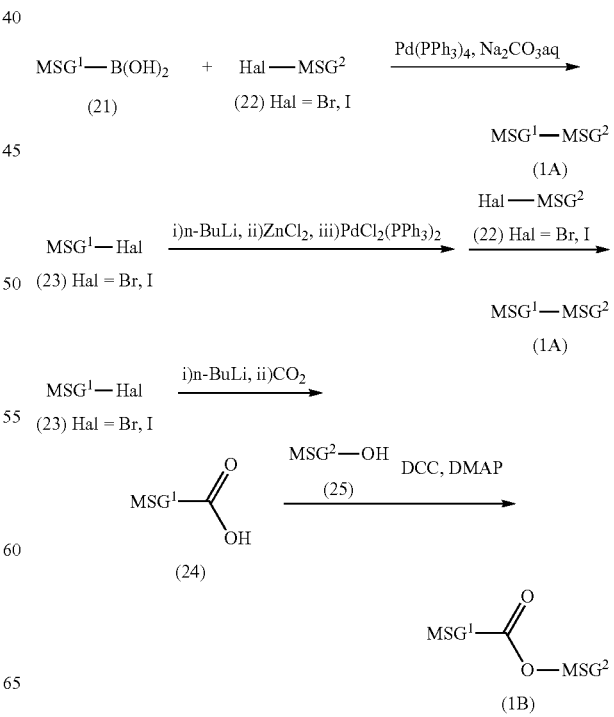

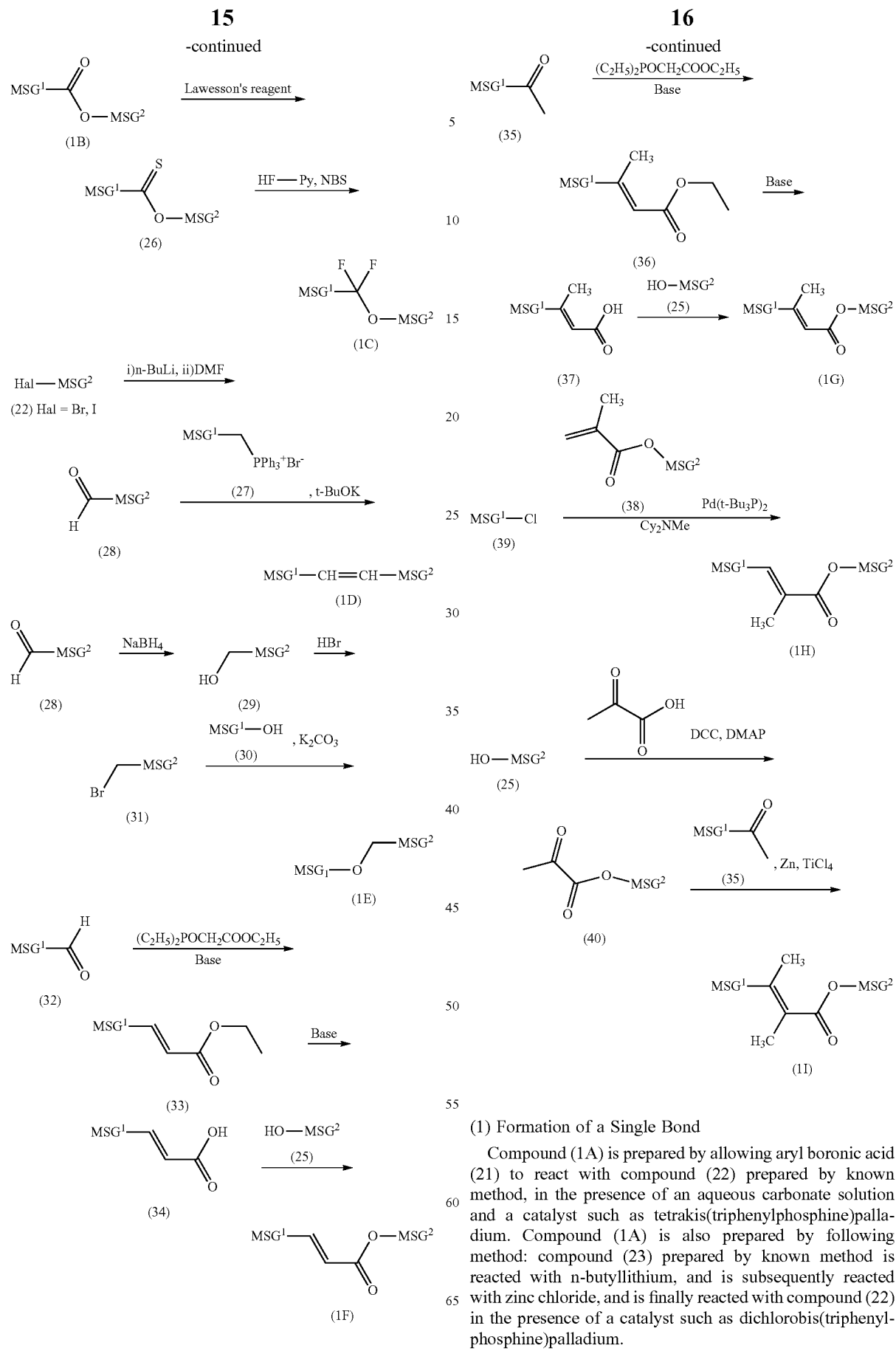

(1) Formation of a Single Bond

Compound (1A) is prepared by allowing aryl boronic acid (21) to react with compound (22) prepared by known method, in the presence of an aqueous carbonate solution and a catalyst such as tetrakis(triphenylphosphine)palladium. Compound (1A) is also prepared by following method: compound (23) prepared by known method is reacted with n-butyllithium, and is subsequently reacted with zinc chloride, and is finally reacted with compound (22) in the presence of a catalyst such as dichlorobis(triphenylphosphine)palladium.

(2) Formation of —COO—

Carboxylic acid (24) is obtained, by allowing compound (23) to react with n-butyllithium and subsequently reacting with carbon dioxide. Compound (1B) is prepared by allowing dehydrating mixture of compound (24) and phenol (25) which is prepared according to a publicly known method, in the presence of 1,3-dicyclohexylcarbodiimide (DCC) and N,N-dimethyl-4-aminopyridine (DMAP).

(3) Formation of —CF$_2$O—

Compound (26) is obtained by treating compound (1B) with a thiation reagent such as Lawesson's reagent. Compound (1C) is prepared by fluorinating compound (26) in the presence of a hydrogen fluoride-pyridine complex and N-bromosuccinimide (NBS). Refer to M. Kuroboshi et al., Chem. Lett., 1992, 827. Compound (1C) is also prepared by fluorinating compound (26) in the presence of (diethylamino)sulfur trifluoride (DAST). See W. H. Bunnelle et al., J. Org. Chem. 1990, 55, 768. The bonding groups can also be formed according to the method described in Peer. Kirsch et al., Angew. Chem. Int. Ed. 2001, 40, 1480.

(4) Formation of —CH=CH—

Aldehyde (28) is obtained by, treating compound (22) with n-butyllithium and then allowing the treated compound to react with formamide such as N,N-dimethylformamide (DMF). Compound (1D) is prepared by allowing phosphorus ylide generated by treating phosphonium salt (27) prepared by a known method, with a base such as potassium tert-butoxide to react with aldehyde (28). A cis isomer thereof might be generated depending on reaction conditions, and the cis isomer is isomerized into a trans isomer by a known method, when necessary.

(5) Formation of —CH$_2$O—

Compound (29) is obtained by reducing compound (28) with a reducing agent such as sodium borohydride. Compound (31) is obtained by halogen-substituting the obtained compound by using hydrobromic acid or the like. Compound (1E) is prepared by allowing compound (31) to react with compound (30) in the presence of potassium carbonate or the like.

(6) Formation of —CH=CH—COO—

Phosphorus ylide is prepared by allowing a base such as sodium hydride to act on ethyl diethylphosphonoacetate, and ester (33) is obtained by allowing the phosphorus ylide to react with aldehyde (32). Carboxylic acid (34) is obtained by hydrolyzing ester (33) in the presence of a base such as sodium hydroxide. Compound (1F) is prepared by allowing dehydrating mixture of the compound and compound (25).

(7) Formation of —C(CH$_3$)=CH—COO—

Phosphorus ylide is prepared by allowing a base such as sodium hydride to act on ethyl diethylphosphonoacetate, and ester (36) is obtained by allowing the phosphorus ylide to react with methyl ketone (35). Next, carboxylic acid (37) is obtained by hydrolyzing ester (36) in the presence of a base such as sodium hydroxide. Then, compound (1G) is prepared by dehydrating mixture of the resulting compound and compound (25).

(8) Formation of —CH=C(CH$_3$)—COO—

Compound (1H) is prepared by allowing mixture of compound (38) which is prepared by known synthesis method and compound (39) which is prepared by known method, in the presence of a base such as N,N-dicyclohexylmethylamine (Cy$_2$NMe) and a catalyst such as bis(tri-tert-butylphosphine)palladium.

(9) Formation of —C(CH$_3$)=C(CH$_3$)—COO—

Compound (40) is obtained by dehydrating mixture of compound (25) and pyruvic acid. Compound (1I) is prepared by allowing compound (40) to react with compound (35) in the presence of zinc and titanium tetrachloride.

2-2. Formation of Connecting Group S

P$^1$ or P$^2$ is a polymerizable group. Preferred examples of the polymerizable group include acryloyloxy (P-1), vinyloxy (P-2) and oxiranyl (P-3). In formula (P-1), M$^1$ and M$^2$ are independently hydrogen, fluorine, methyl or trifluoromethyl.

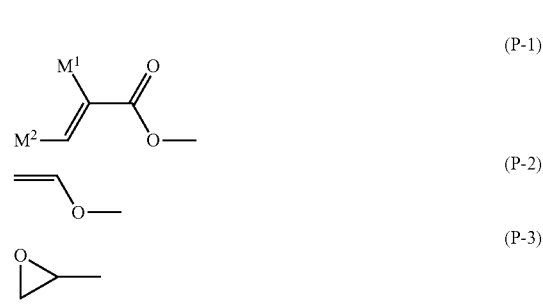

An example of a method for preparing a compound in which the polymerizable group is bonded with a ring through connecting group S is as described below. First, an example in which connecting group S is a single bond will be shown.

(1) Formation of a Single Bond

A method for forming a single bond is as described in a scheme below. In the scheme, MSG$^1$ is a monovalent organic group having at least one ring. Compounds (1S) to (1X) correspond to compound (1).

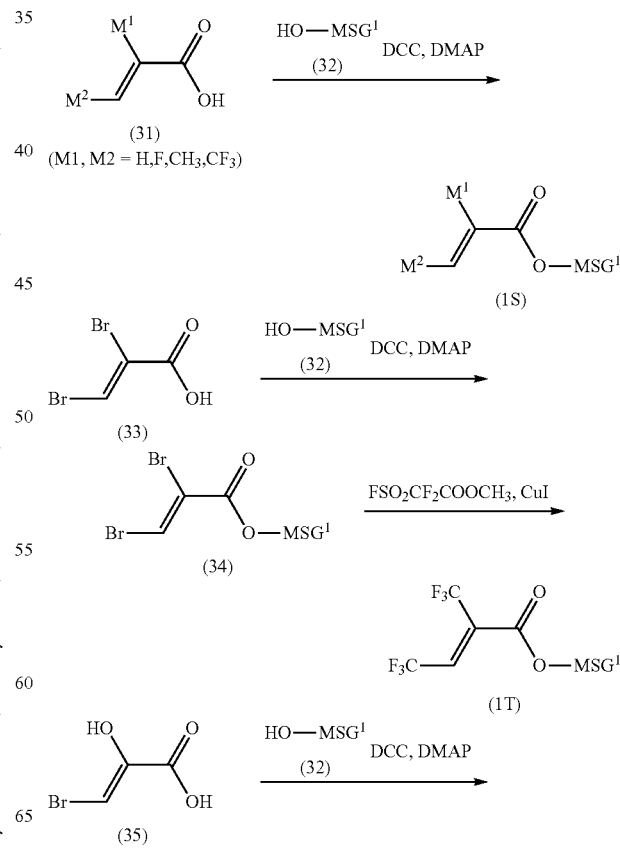

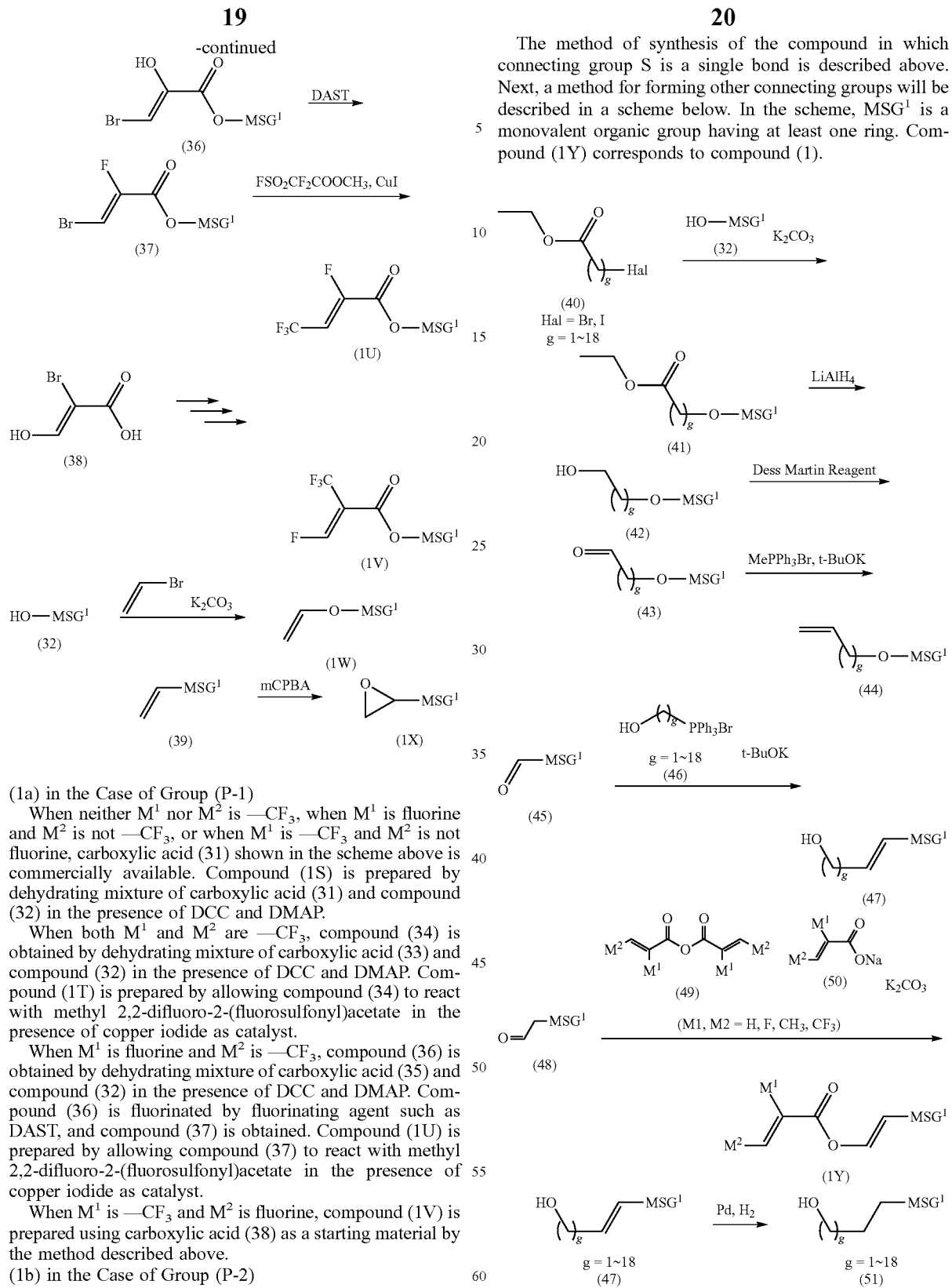

The method of synthesis of the compound in which connecting group S is a single bond is described above. Next, a method for forming other connecting groups will be described in a scheme below. In the scheme, MSG$^1$ is a monovalent organic group having at least one ring. Compound (1Y) corresponds to compound (1).

(1a) in the Case of Group (P-1)

When neither M$^1$ nor M$^2$ is —CF$_3$, when M$^1$ is fluorine and M$^2$ is not —CF$_3$, or when M$^1$ is —CF$_3$ and M$^2$ is not fluorine, carboxylic acid (31) shown in the scheme above is commercially available. Compound (1S) is prepared by dehydrating mixture of carboxylic acid (31) and compound (32) in the presence of DCC and DMAP.

When both M$^1$ and M$^2$ are —CF$_3$, compound (34) is obtained by dehydrating mixture of carboxylic acid (33) and compound (32) in the presence of DCC and DMAP. Compound (1T) is prepared by allowing compound (34) to react with methyl 2,2-difluoro-2-(fluorosulfonyl)acetate in the presence of copper iodide as catalyst.

When M$^1$ is fluorine and M$^2$ is —CF$_3$, compound (36) is obtained by dehydrating mixture of carboxylic acid (35) and compound (32) in the presence of DCC and DMAP. Compound (36) is fluorinated by fluorinating agent such as DAST, and compound (37) is obtained. Compound (1U) is prepared by allowing compound (37) to react with methyl 2,2-difluoro-2-(fluorosulfonyl)acetate in the presence of copper iodide as catalyst.

When M$^1$ is —CF$_3$ and M$^2$ is fluorine, compound (1V) is prepared using carboxylic acid (38) as a starting material by the method described above.

(1b) in the Case of Group (P-2)

Compound (1W) is prepared by allowing compound (32) to react with vinyl bromide in the presence of potassium carbonate or the like.

(1c) in the Case of Group (P-3)

Vinyl compound (39) which is prepared by publicly known method, is oxidized by using meta-chloroperbenzoic acid (mCPBA) or the like, and compound (1X) is obtained.

(2) Formation of —(CH$_2$)$_g$—O—

Compound (40) which is prepared by publicly known method is reacted with compound (32) in the presence of potassium carbonate or the like, and compound (41) is obtained. Compound (41) is reduced by a reducing agent such as lithium aluminum hydride, and compound (42) is obtained. Compound (42) is oxidized by an oxidizing agent such as a Dess-Martin reagent, and aldehyde (43) is obtained. Phosphorus ylide, which is generated by treating methyltriphenylphosphonium bromide in the presence of base such as potassium tert-butoxide, is reacted with aldehyde (43), and compound (44) is obtained.

When group (P-1) is introduced into compound (42), dehydrating mixture of compound (42) and compound (31) is performed by the method described above. When group (P-2) is introduced into compound (42), a reaction of compound (42) and vinyl bromide is performed by the method described above. When group (P-3) is introduced into compound (44), an epoxidation reaction of compound (44) is performed by the method described above.

(3) Formation of —$(CH_2)_g$—CH=CH—

Phosphonium salt (46), which is prepared by a publicly known method, is reacted with a base such as potassium tert-butoxide by publicly known method, and subsequently reacted with aldehyde (45), and compound (47) is obtained. When group (P-1) is introduced into compound (47), dehydrating mixture of compound (42) and compound (32) is performed by the method described above. When group (P-2) is introduced into compound (47), a reaction of compound (47) and vinyl bromide is performed by method described above. When group (P-3) is introduced into compound (47), —$CH_2OH$ is converted into —CH=$CH_2$, and then an epoxidation reaction is performed by method described above.

(4) Formation of —CH=CH—

Compound (1Y) is prepared by allowing aldehyde (48), which is prepared according to publicly known method, to react with acid anhydride (49) and sodium carboxylate (50) in the presence of potassium carbonate or the like.

(5) Formation of —$(CH_2)_g$—

Alcohol (51) is prepared by hydrogenating compound (47) in the presence of a catalyst such as palladium on carbon. Methods for introducing $M^2CH=CM^1$-COO—, a vinyloxy group or an epoxy group into the alcohol is described above.

Compound (1) has further suitable polymerization reactivity, higher conversion and higher compatibility in the liquid crystal composition, compared with compounds corresponding. Compound (1) has a suitable balance regarding at least two of the physical properties. Accordingly, compound (1) is available to add to the liquid crystal composition for the PSA mode.

3. Polymerizable Composition

A polymerizable composition contains at least one of compound (1) as a first component. A component of the composition may include only the first component. The composition may also contain other components such as a second component and a third component. A kind of the second component or the like depends on an application of an objective polymer. The polymerizable composition may further contain any other polymerizable compound different from compound (1) as the second component. Preferred examples of other polymerizable compounds include acrylate, methacrylate, a vinyl compound, a vinyloxy compound, propenyl ether, an epoxy compound (oxirane, oxetane) and vinyl ketone. Further preferred examples include a compound having at least one of acryloyloxy and a compound having at least one of methacryloyloxy. Still further preferred examples include a compound having both acryloyloxy and methacryloyloxy.

Additional examples of other polymerizable compounds include compounds (M-1) to (M-12). In compounds (M-1) to (M-12), $R^{25}$, $R^{26}$ and $R^{27}$ are independently hydrogen or methyl; u, x and y are independently 0 or 1; v and w are independently an integer from 1 to 10; and $L^{21}$, $L^{22}$, $L^{23}$, $L^{24}$, $L^{25}$ and $L^{26}$ are independently hydrogen or fluorine.

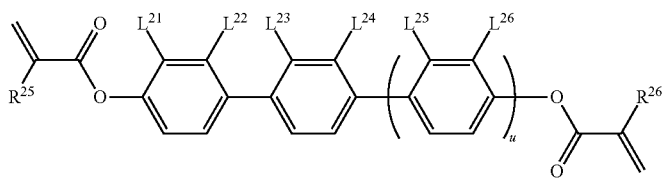

(M-1)

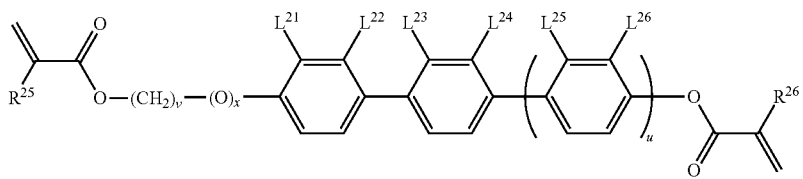

(M-2)

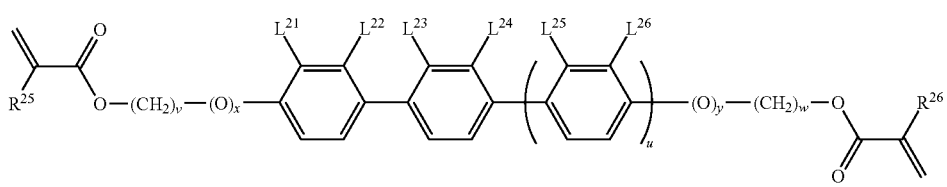

(M-3)

-continued
(M-4)
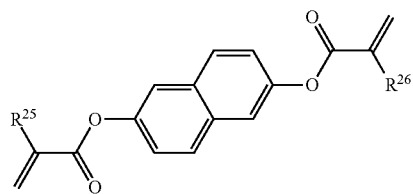
(M-5)
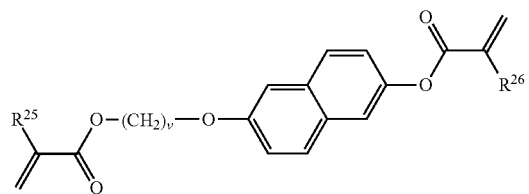
(M-6)
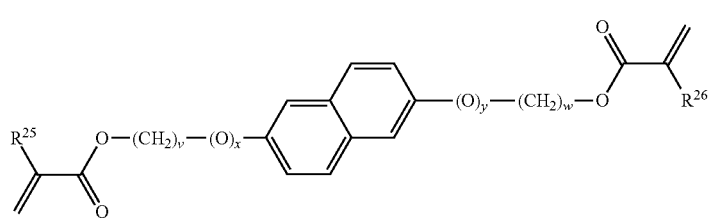
(M-7)
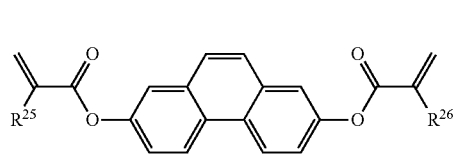
(M-8)
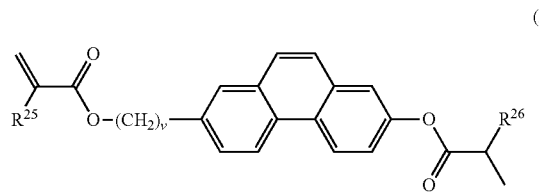
(M-9)
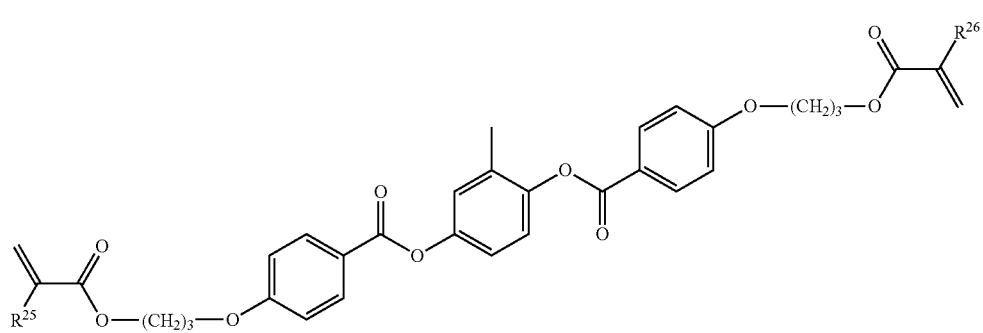
(M-10)
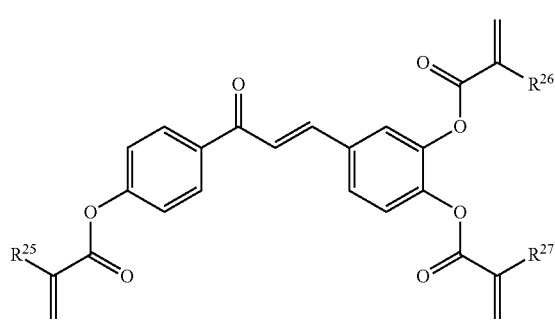
(M-11)
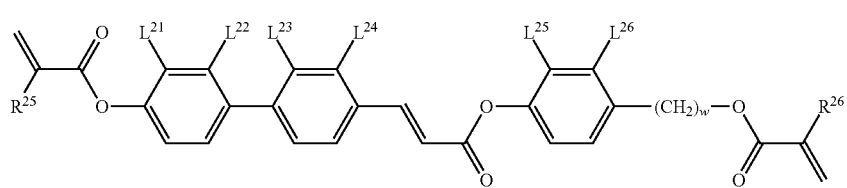

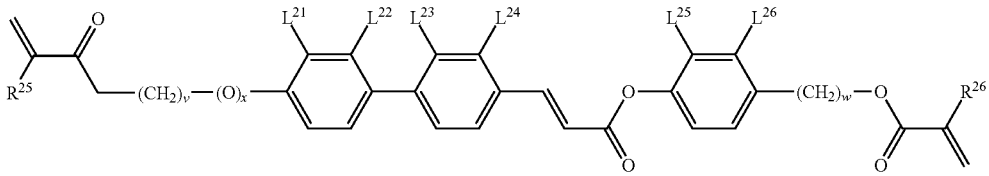

(M-12)

When the second component of the polymerizable composition is a polymerizable compound having a liquid crystal phase, an optically anisotropic body is formed by allowing polymerization while controlling alignment of liquid crystal molecules. The optically anisotropic body can be used for a phase difference film, a polarized light device, a circularly polarized light device, an elliptically polarized light device, an antireflection film, a selective reflection film, a color compensation film, a viewing angle compensation film or the like. An additive such as a polymerization initiator may be added to the polymerizable composition for the purpose of adjusting physical properties of the optically anisotropic body.

The polymerizable composition may also contain the liquid crystal composition as the second component. When a liquid crystal display device having a mode such as PS-TN, PS-IPS, PS-FFS, PSA-VA and PSA-OCB is targeted, the polymerizable composition preferably contains compound (1) as component A, and further contains a compound selected from components B, C and D shown below. Component B includes compounds (2) to (4). Component C includes compounds (5) to (7). Component D includes compound (8). Upon preparing such a polymerizable composition, components B, C and D are preferably selected in taking consideration of positive or negative dielectric anisotropy, magnitude of dielectric anisotropy, or the like. The polymerizable composition, which is taking considerations and is prepared by properly selecting the component, has a high maximum temperature, a low minimum temperature, a small viscosity, a suitable optical anisotropy (in other words, large and small of optical anisotropy), a large positive or negative dielectric anisotropy and a suitable elastic constant (in other words, large and small of elastic constant).

The polymerizable composition is prepared by adding compound (1) to the liquid crystal composition. Additives may be added to the composition, when necessary. In such a polymerizable composition, an amount of addition of compound (1), namely, component A is in the range of approximately 0.05% by weight to approximately 20% by weight based on the liquid crystal composition. Further preferred amount of addition is in the range of approximately 0.1% by weight to approximately 10% by weight. Most preferred amount of addition is in the range of approximately 0.2% by weight to approximately 1% by weight. At least one of other polymerizable compounds different from compound (1) may be further added thereto. In the above case, an amount of addition of compound (1) and any other polymerizable compound in total is preferably within the range described above. Physical properties of the polymer to be formed can be adjusted by properly selecting any other polymerizable compound. Examples of other polymerizable compounds include acrylate and methacrylate, as previously described. The examples also include compounds (M-1) to (M-12).

Component B is a compound in which two terminal groups are alkyl or the like. Specific preferred examples of component B include compounds (2-1) to (2-11), compounds (3-1) to (3-19) or compounds (4-1) to (4-7). In the compounds of component B, $R^{11}$ and $R^{12}$ are independently alkyl having 1 to 10 carbons or alkenyl having 2 to 10 carbons, and in the alkyl or the alkenyl, at least one of —$CH_2$— may be replaced by —O—, and at least one of hydrogen may be replaced by fluorine.

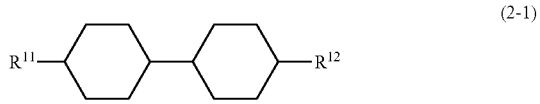

(2-1)

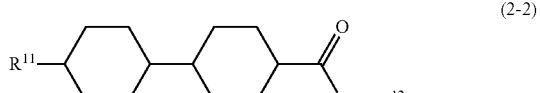

(2-2)

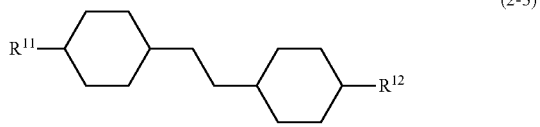

(2-3)

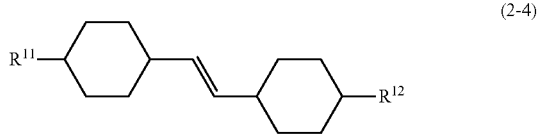

(2-4)

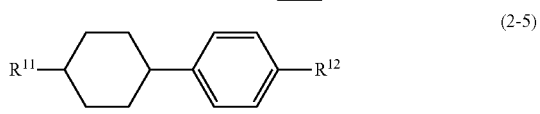

(2-5)

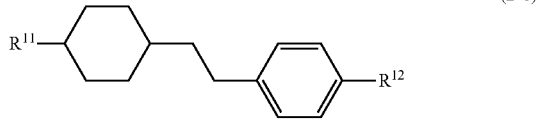

(2-6)

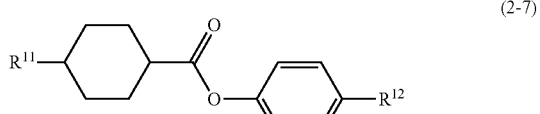

(2-7)

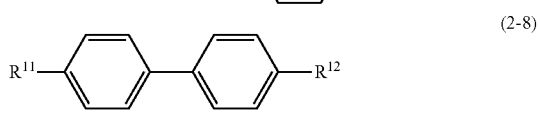

(2-8)

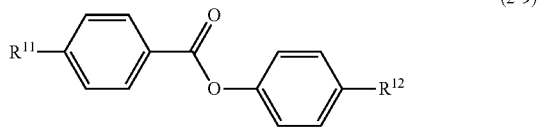

(2-9)

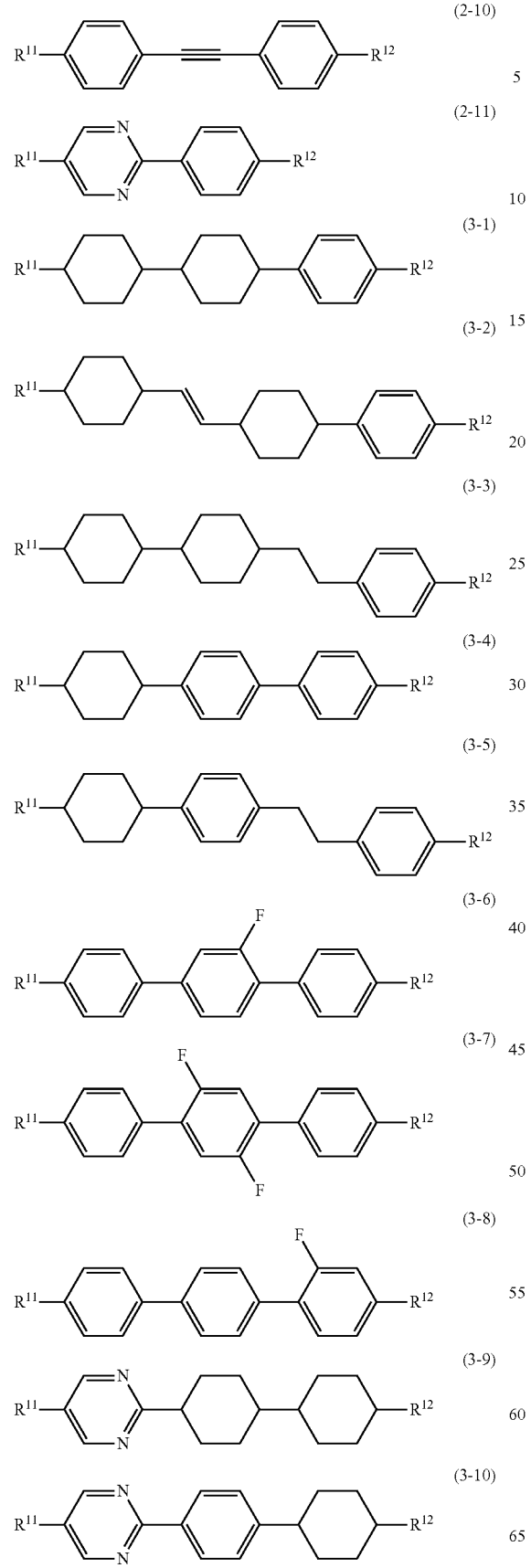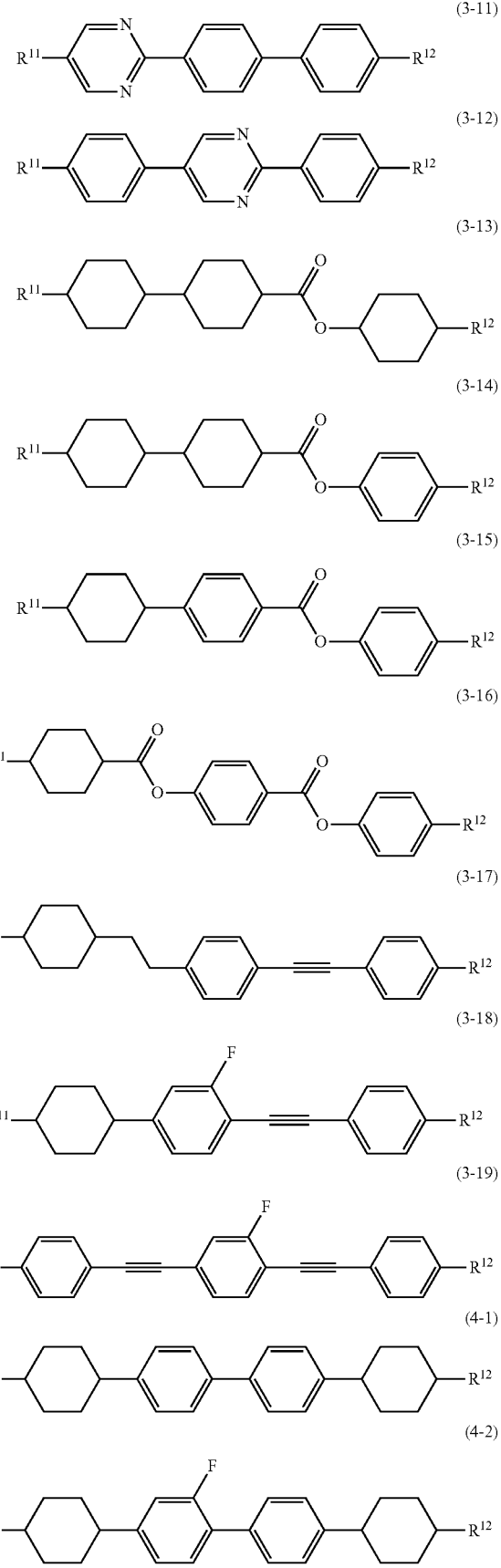

-continued (4-3)
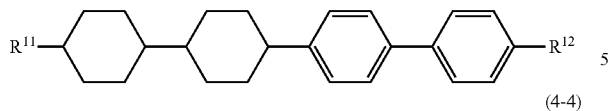

(4-4)
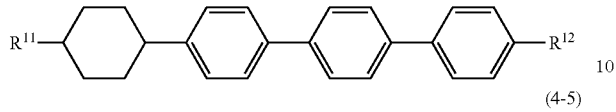

(4-5)
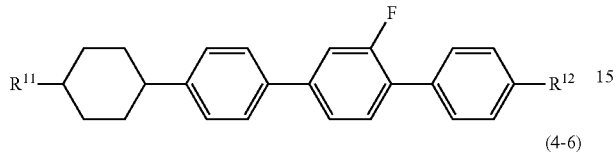

(4-6)
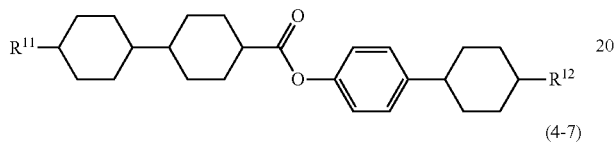

(4-7)
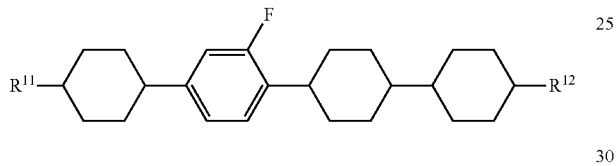

Component B has a small absolute value of dielectric anisotropy, and therefore is a compound in which the value is nearly neutral. Compound (2) is effective in adjusting the viscosity or the optical anisotropy. Compounds (3) and (4) are effective in extending the temperature range of the nematic phase by increasing the maximum temperature, or effective in adjusting the optical anisotropy.

If a content of component B is increased, the dielectric anisotropy of the composition decreases, but the viscosity decreases. Thus, the content is preferably increased, as long as a required value of threshold voltage of the device is satisfied. Accordingly, when preparing a composition for a mode such as PS-IPS and PSA-VA, the content of component B is preferably, based on the weight of the liquid crystal composition, in the range of approximately 30% by weight or more, and further preferably, in the range of approximately 40% by weight or more.

Component C includes a compound having a halogen-containing or fluorine-containing group at a right terminal. Specific preferred examples of component C include compounds (5-1) to (5-16), compounds (6-1) to (6-113) or compounds (7-1) to (7-57). In the compounds of component C, $R^{13}$ is alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine; and $X^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$.

(5-1)
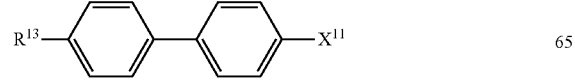

(5-2)
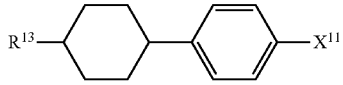

(5-3)

(5-4)
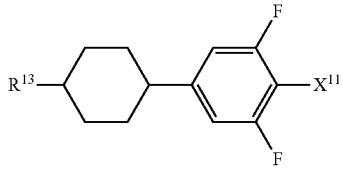

(5-5)
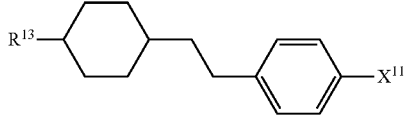

(5-6)
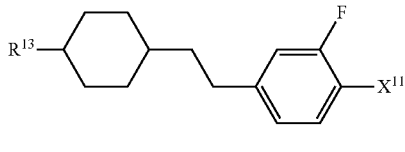

(5-7)
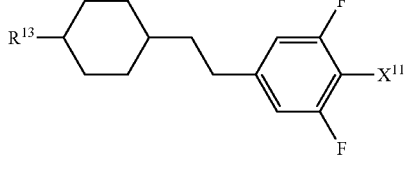

(5-8)
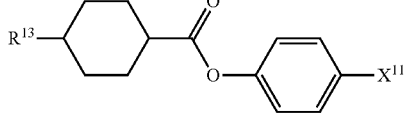

(5-9)
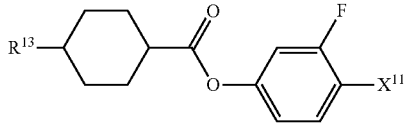

(5-10)
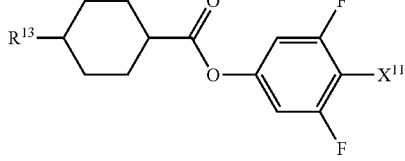

(5-11)
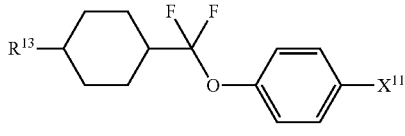

(5-12)

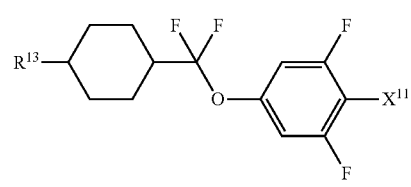 (5-13)
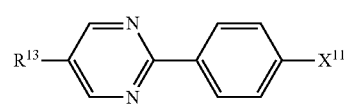 (5-14)
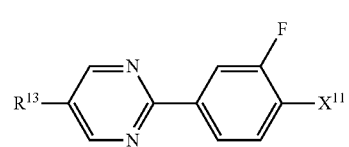 (5-15)
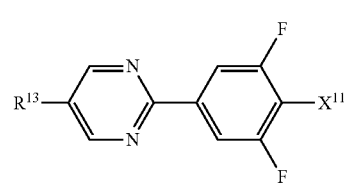 (5-16)
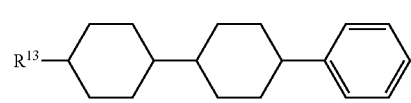 (6-1)
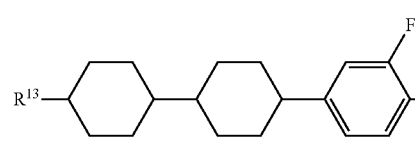 (6-2)
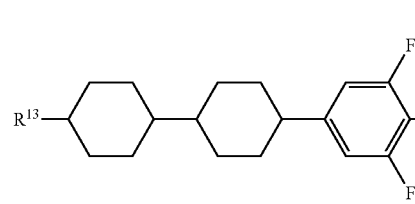 (6-3)
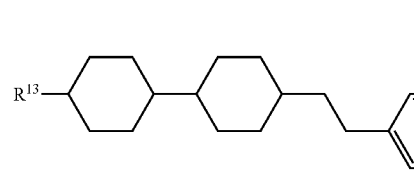 (6-4)
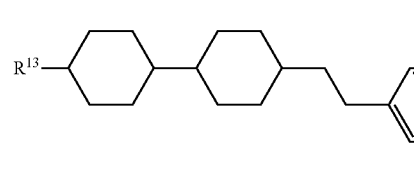 (6-5)
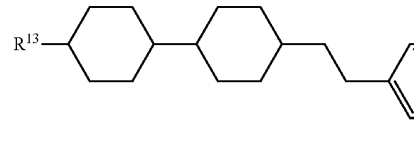 (6-6)
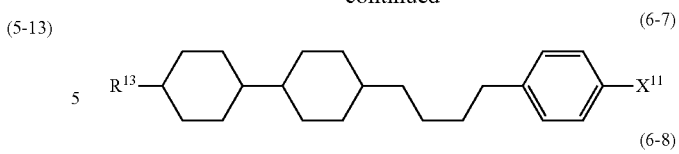 (6-7)
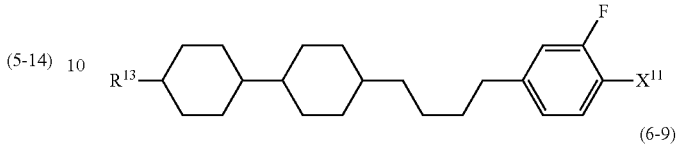 (6-8)
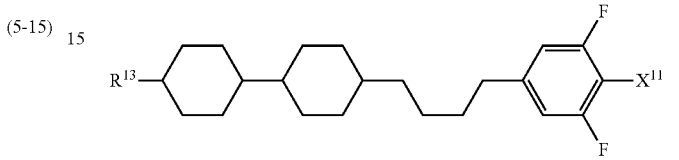 (6-9)
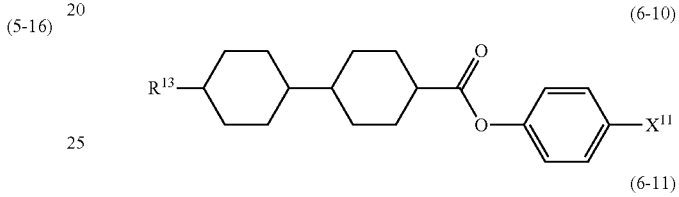 (6-10)
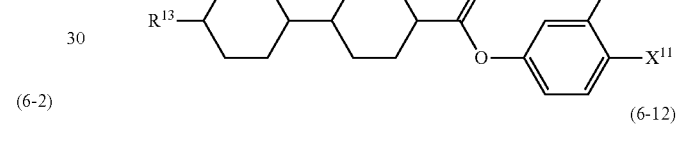 (6-11)
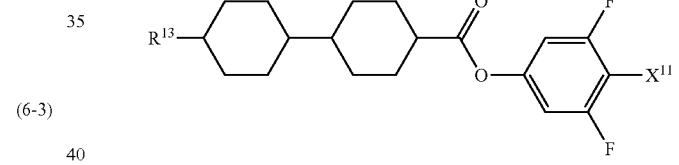 (6-12)
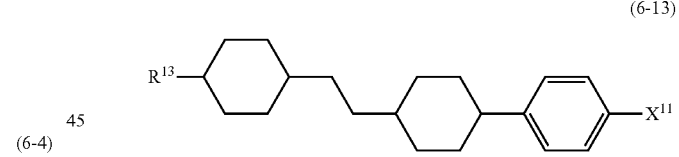 (6-13)
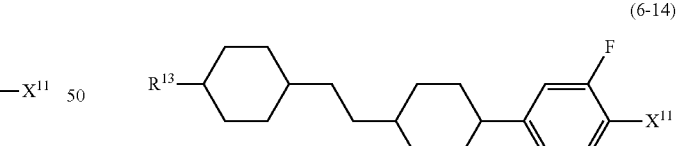 (6-14)
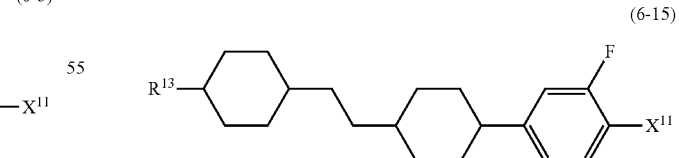 (6-15)
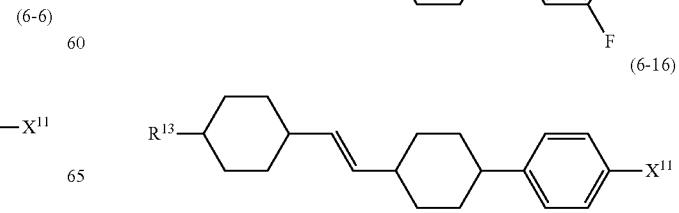 (6-16)

(6-17)
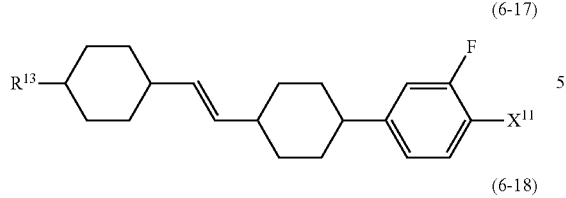
(6-18)
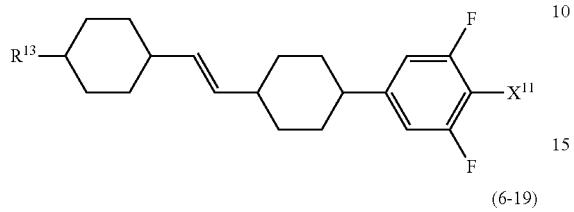
(6-19)
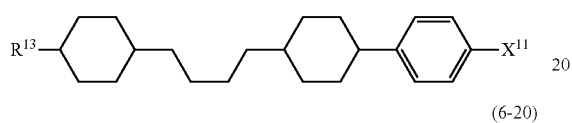
(6-20)
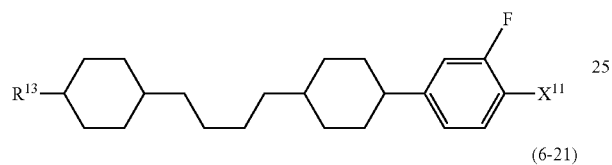
(6-21)
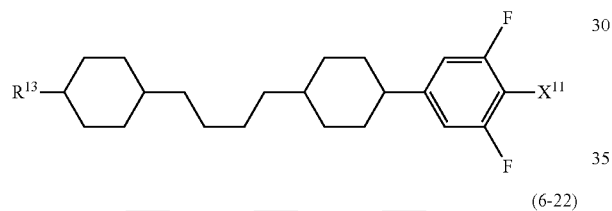
(6-22)
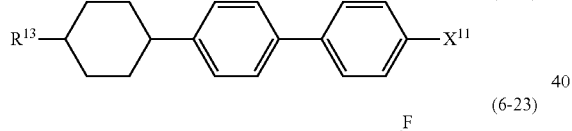
(6-23)
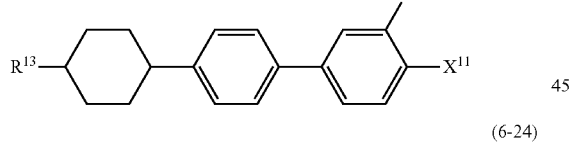
(6-24)
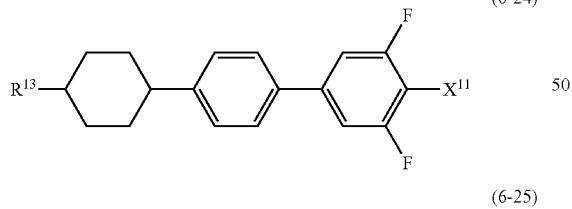
(6-25)
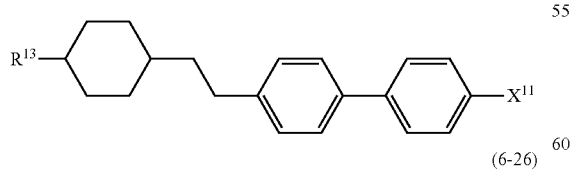
(6-26)
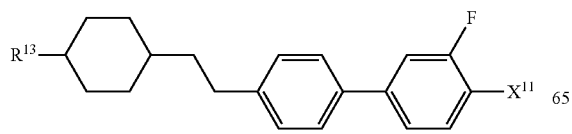
(6-27)
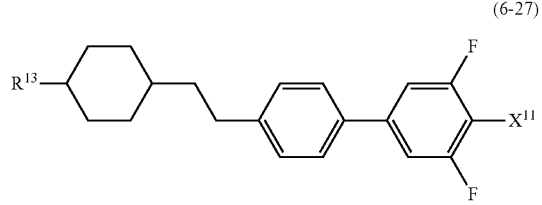
(6-28)
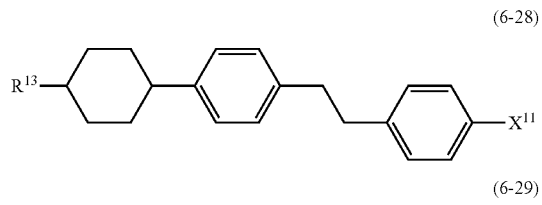
(6-29)
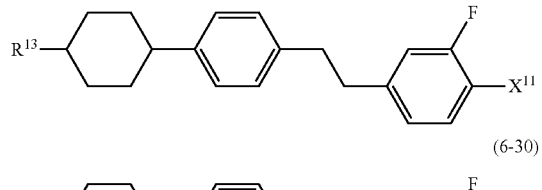
(6-30)
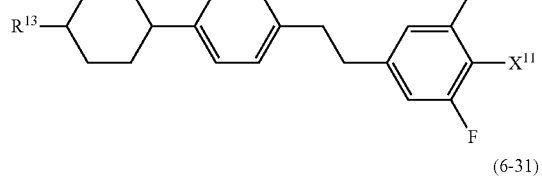
(6-31)
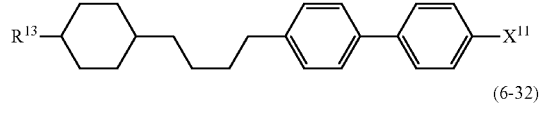
(6-32)
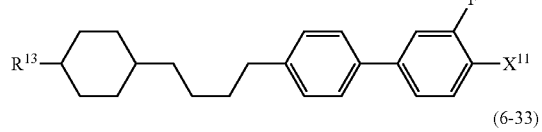
(6-33)
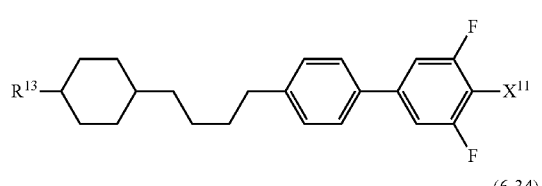
(6-34)
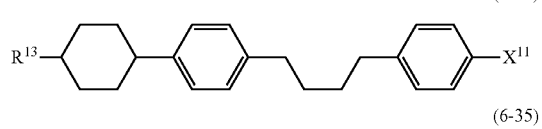
(6-35)
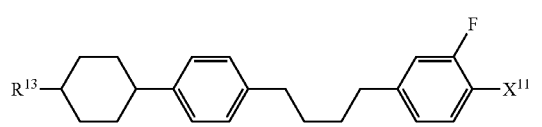
(6-36)
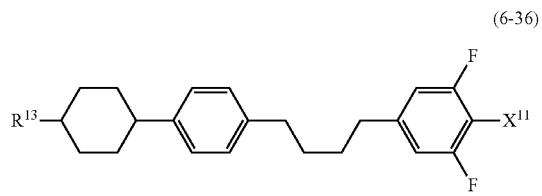

(6-37) 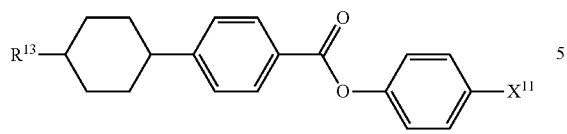
(6-38) 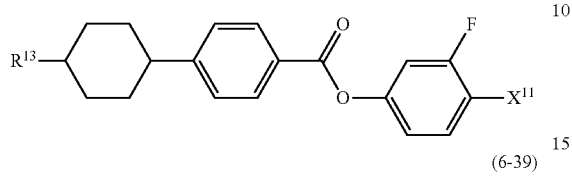
(6-39) 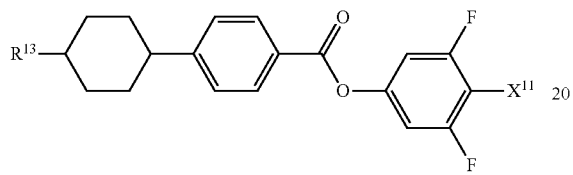
(6-40) 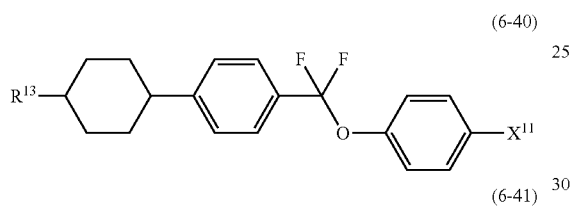
(6-41) 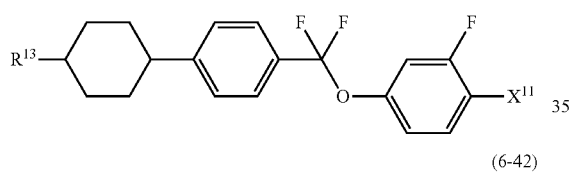
(6-42) 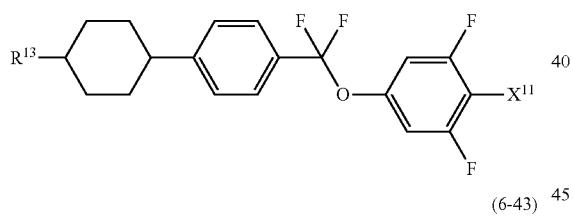
(6-43) 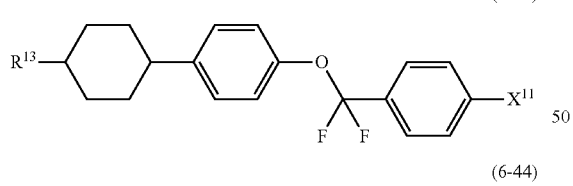
(6-44) 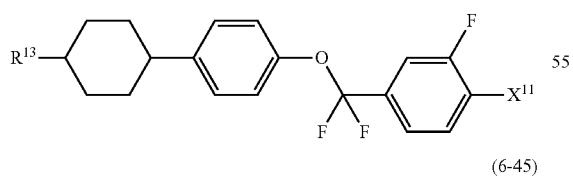
(6-45) 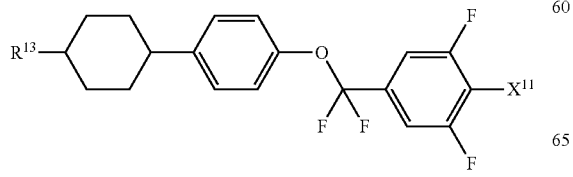
(6-46) 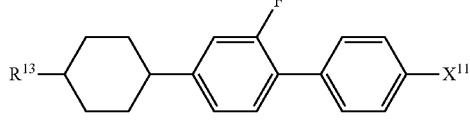
(6-47) 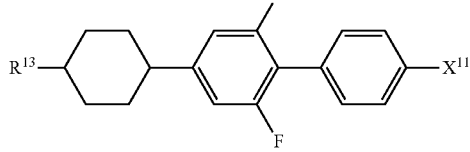
(6-48) 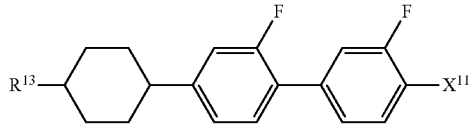
(6-49) 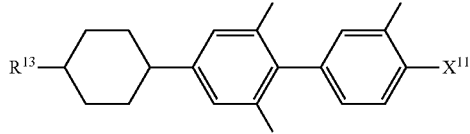
(6-50) 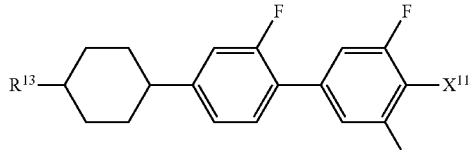
(6-51) 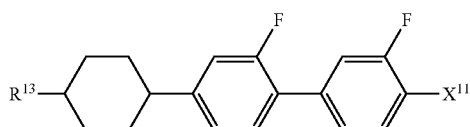
(6-52) 
(6-53) 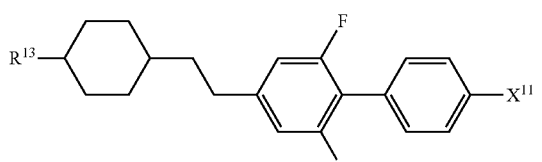
(6-54) 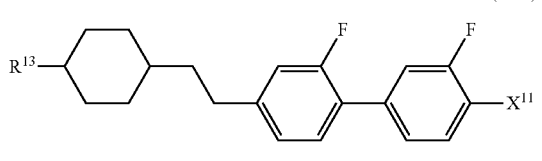

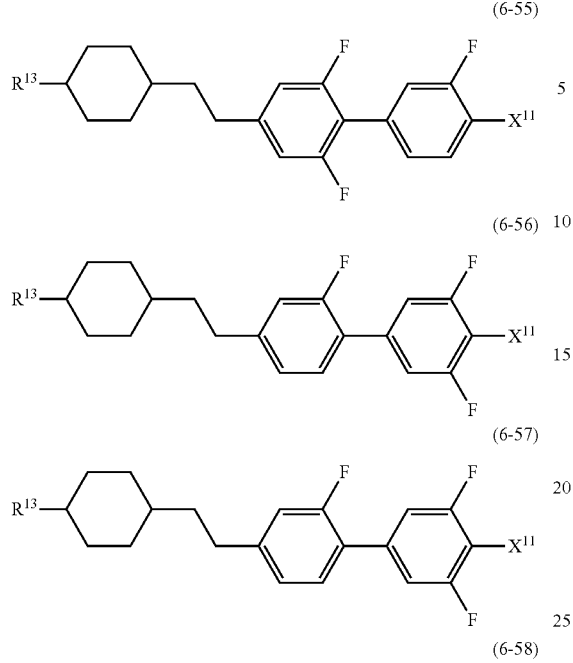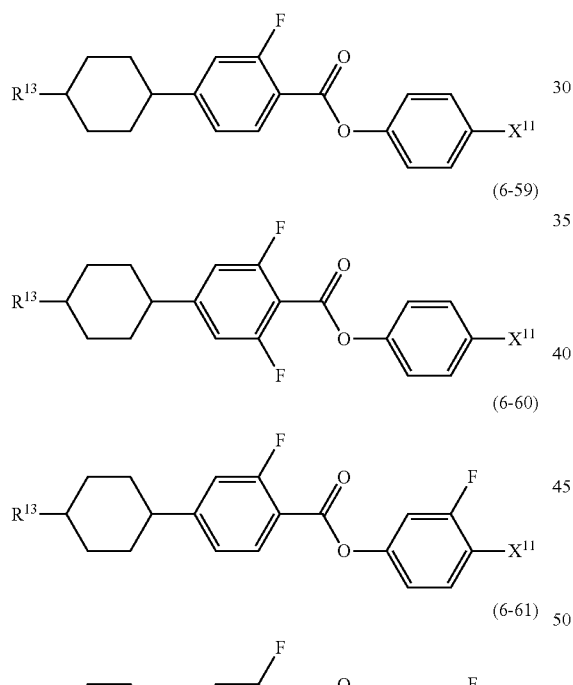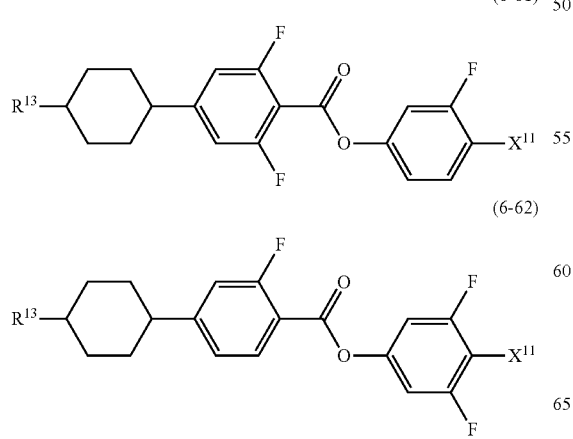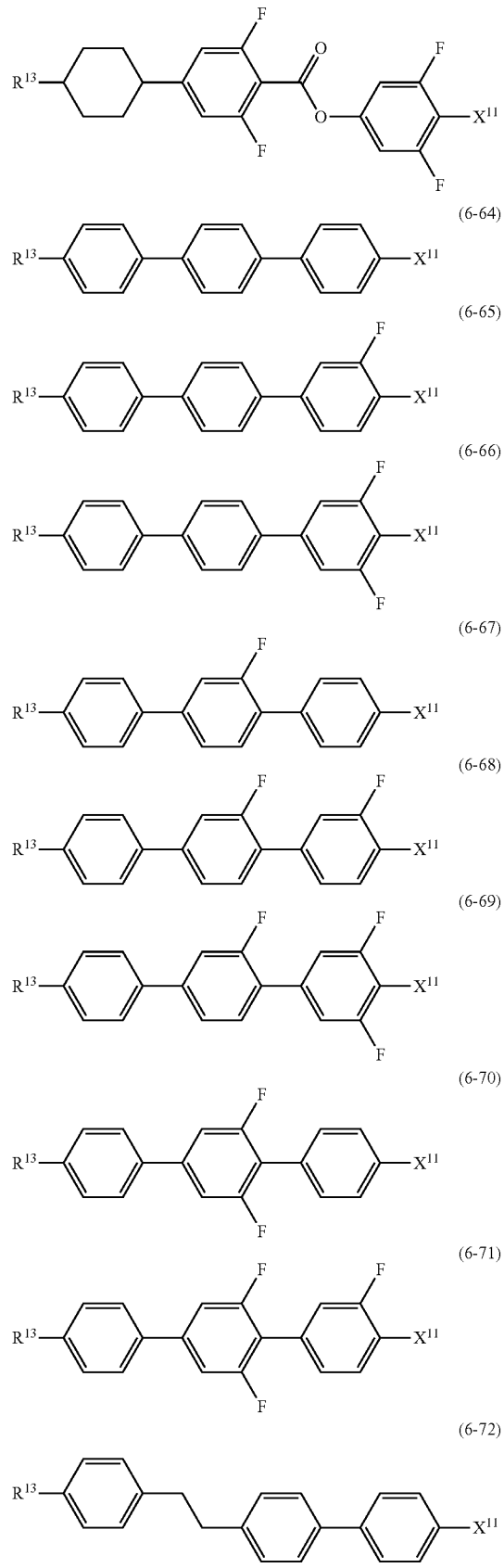

(6-73) 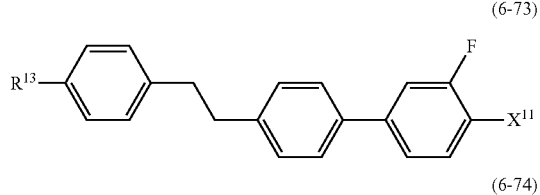
(6-74) 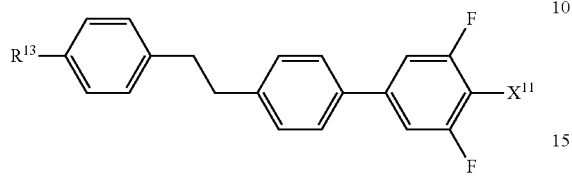
(6-75) 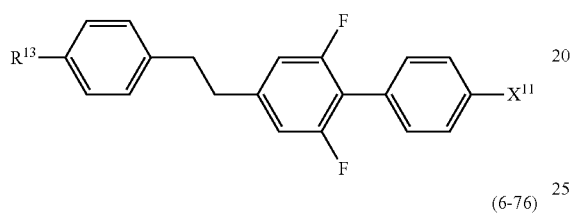
(6-76) 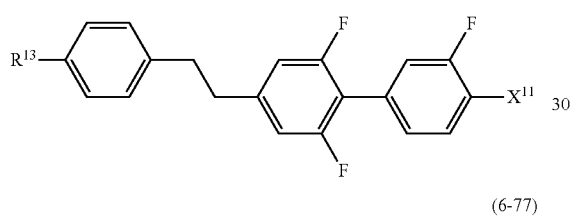
(6-77) 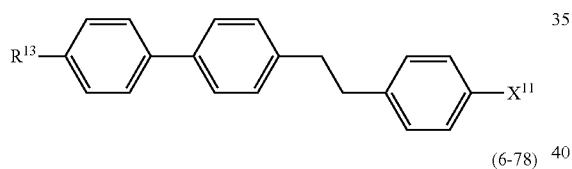
(6-78) 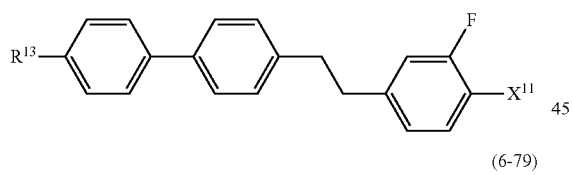
(6-79) 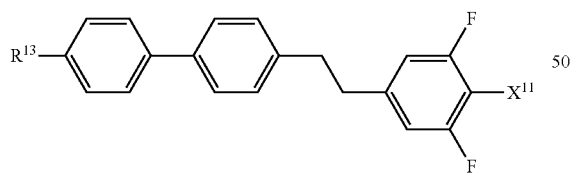
(6-80) 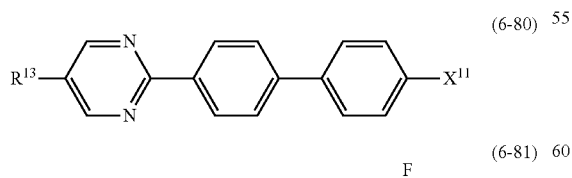
(6-81) 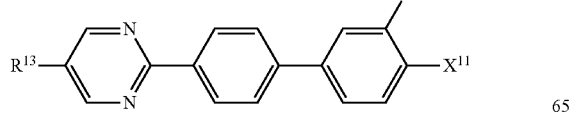
(6-82) 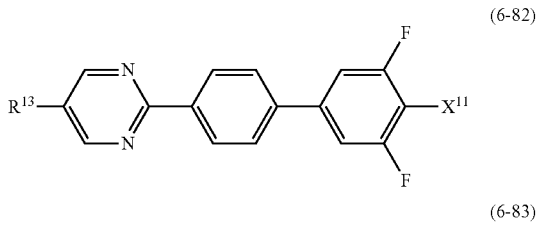
(6-83) 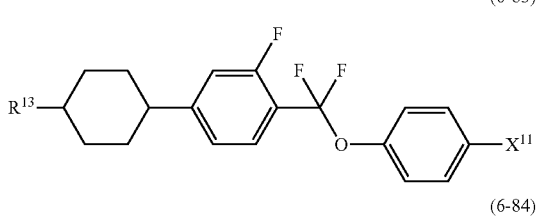
(6-84) 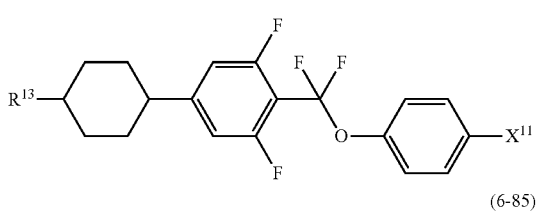
(6-85) 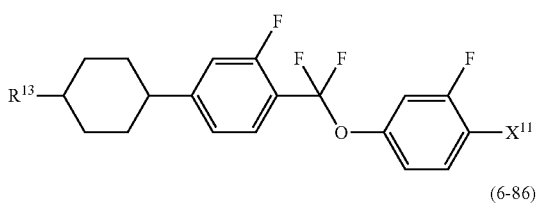
(6-86) 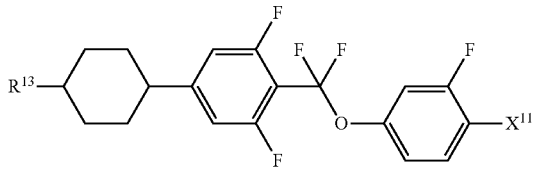
(6-87) 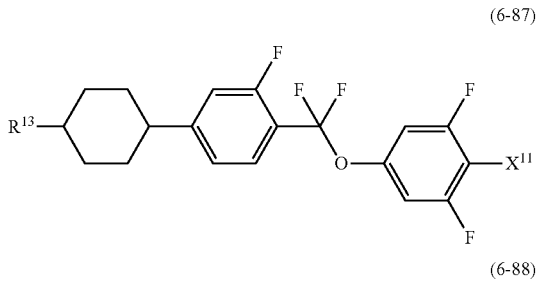
(6-88) 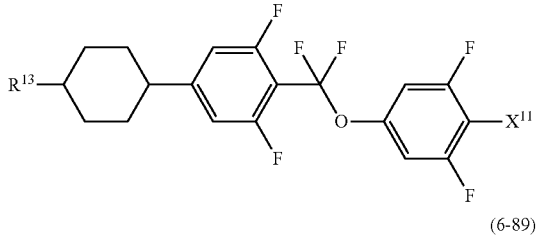
(6-89) 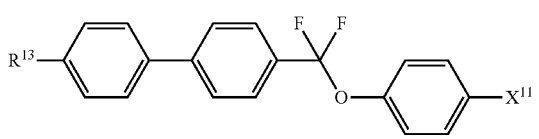

(6-90)
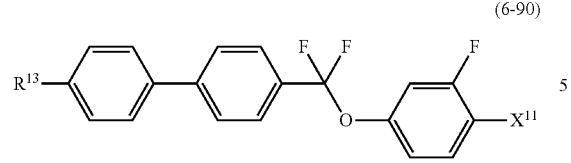
(6-91)
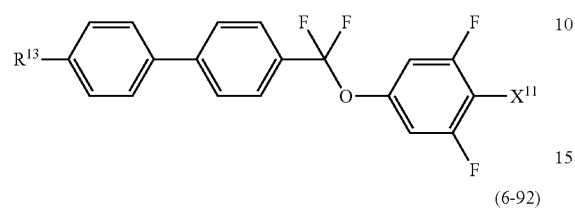
(6-92)
(6-93)
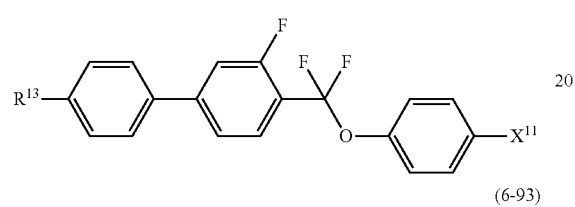
(6-94)
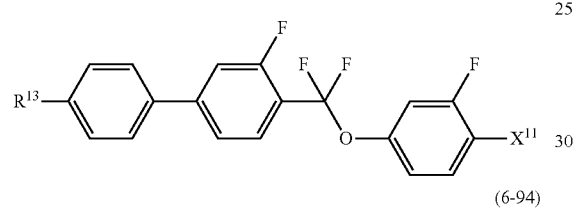
(6-95)
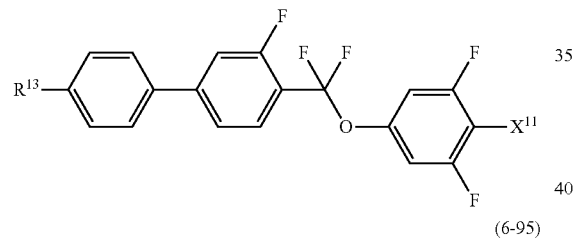
(6-96)
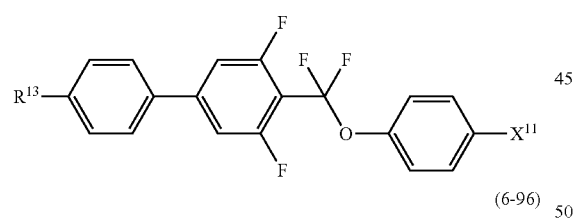
(6-97)
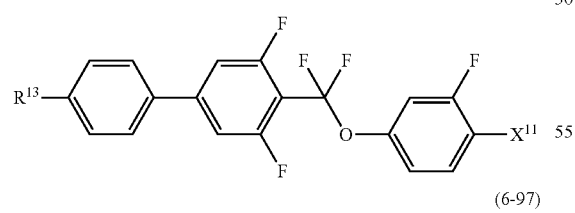
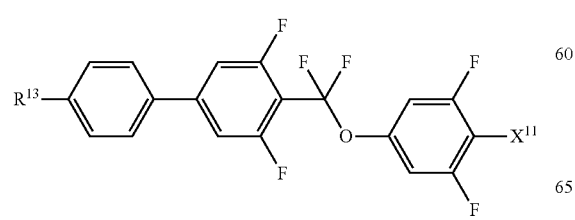
(6-98)
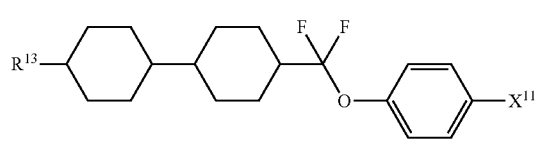
(6-99)
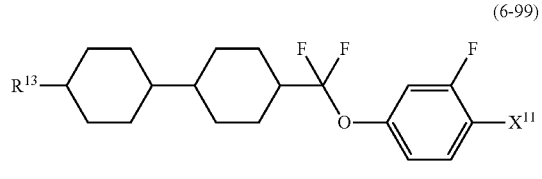
(6-100)
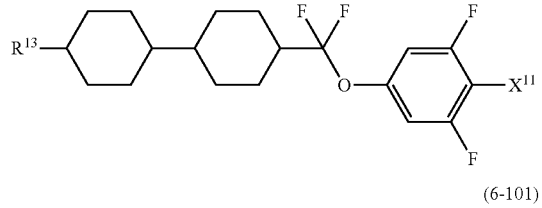
(6-101)
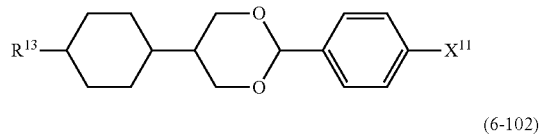
(6-102)
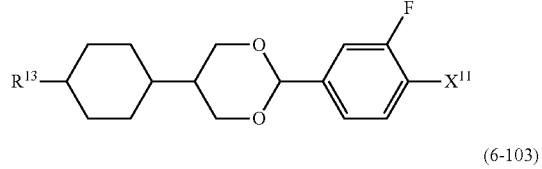
(6-103)
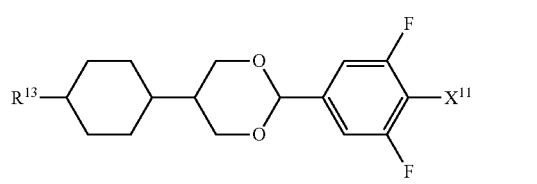
(6-104)
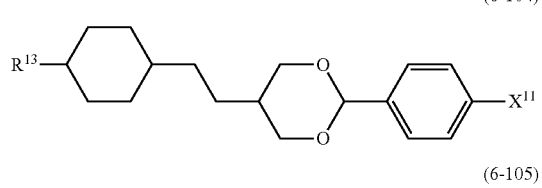
(6-105)
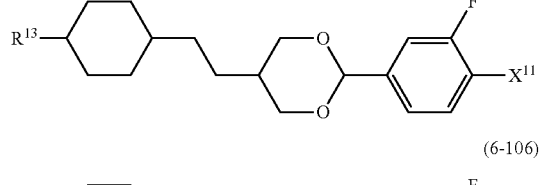
(6-106)
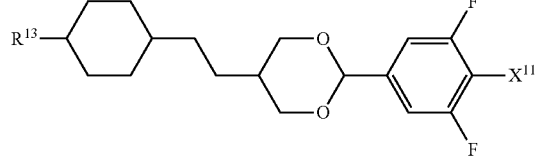

(6-107)
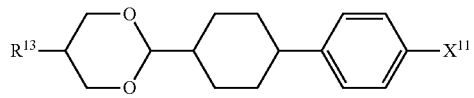
(6-108)
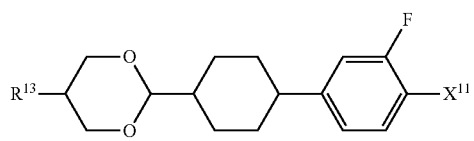
(6-109)
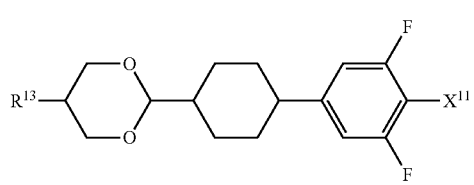
(6-110)
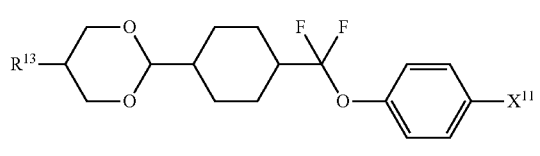
(6-111)
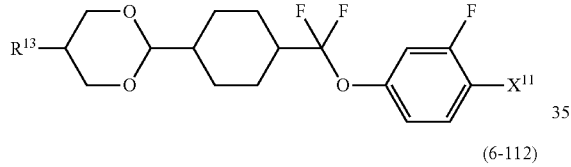
(6-112)
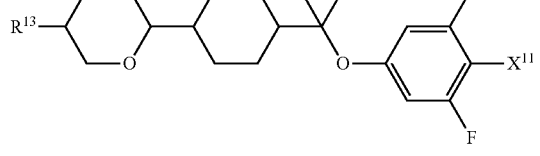
(6-113)
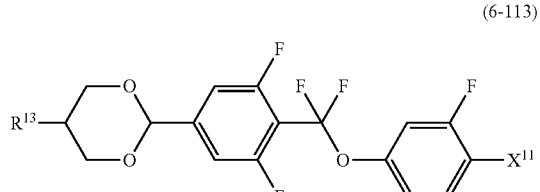
(7-1)
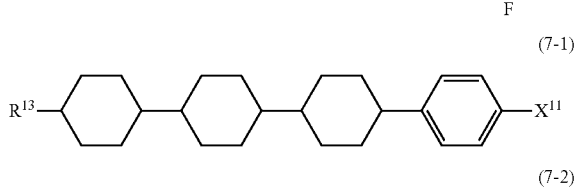
(7-2)
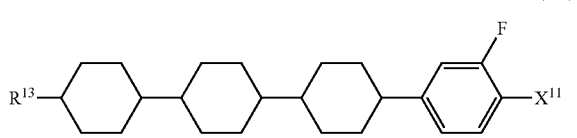
(7-3)
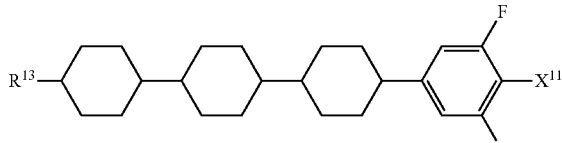
(7-4)
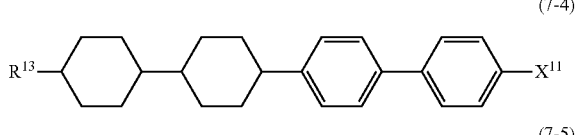
(7-5)
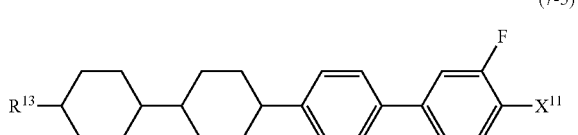
(7-6)
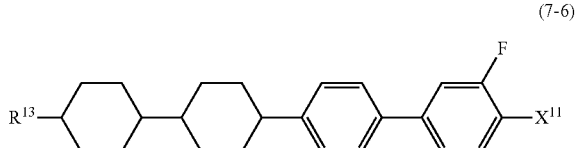
(7-7)
(7-8)
(7-9)
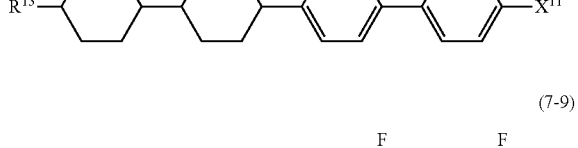
(7-10)
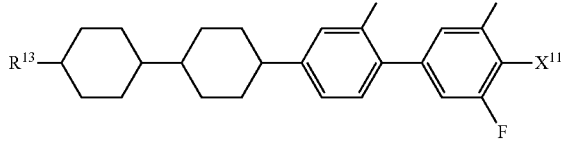
(7-11)
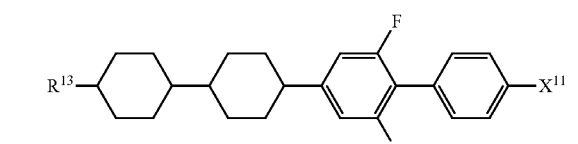
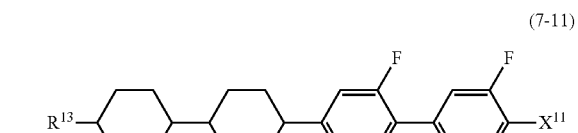
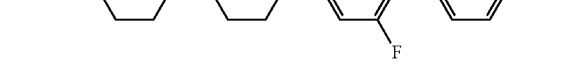

(7-12) 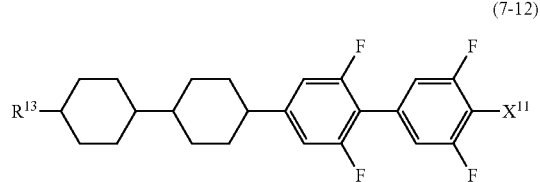
(7-13) 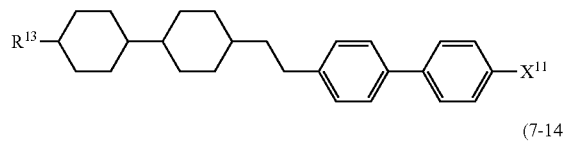
(7-14) 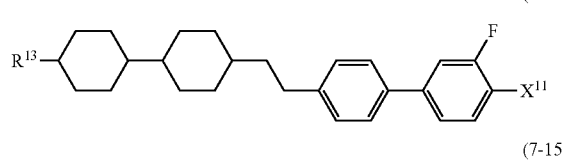
(7-15) 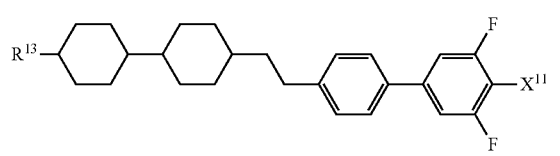
(7-16) 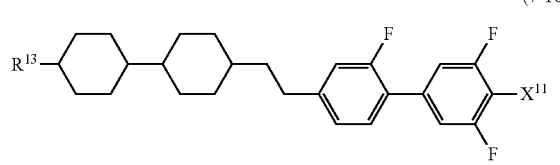
(7-17) 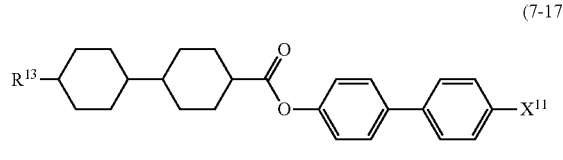
(7-18) 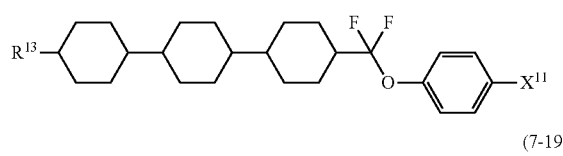
(7-19) 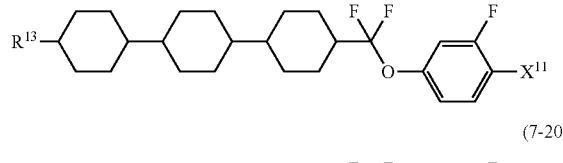
(7-20) 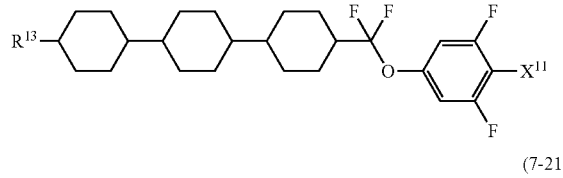
(7-21) 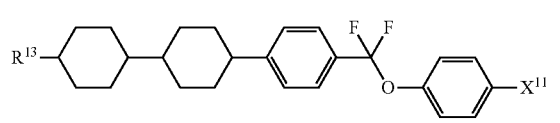
(7-22) 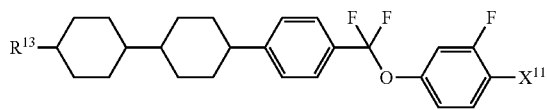
(7-23) 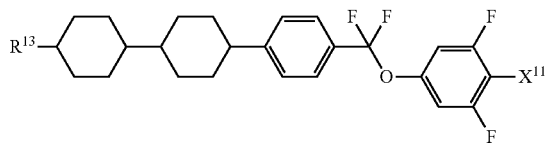
(7-24) 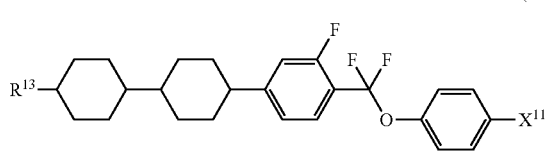
(7-25) 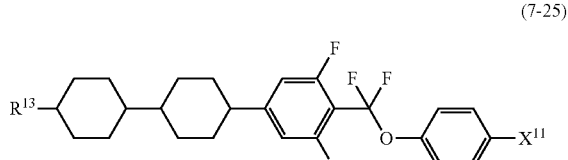
(7-26) 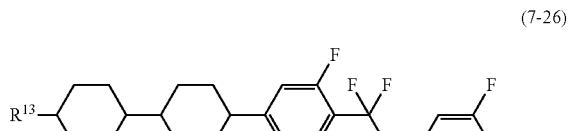
(7-27) 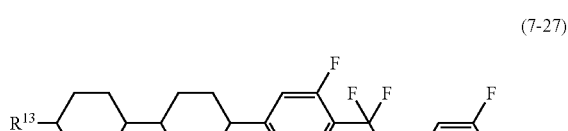
(7-28) 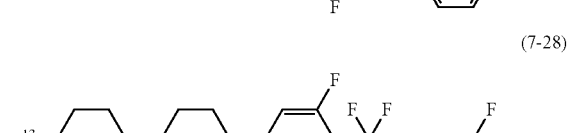
(7-29) 
(7-30) 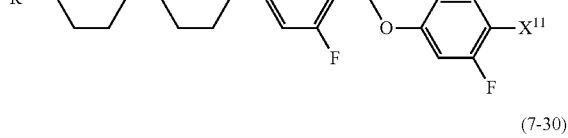

(7-31)
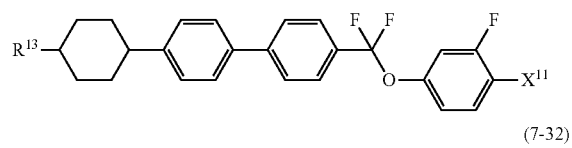
(7-32)
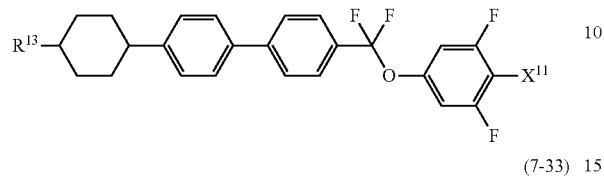
(7-33)
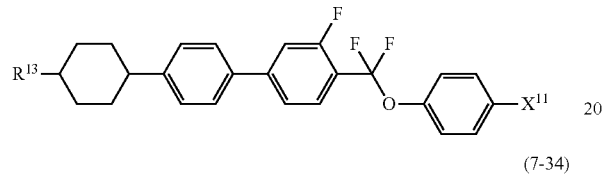
(7-34)
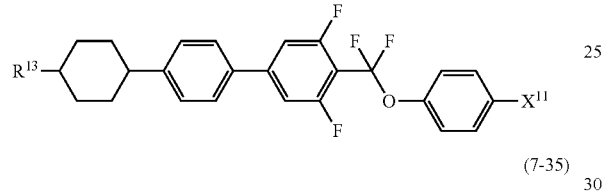
(7-35)
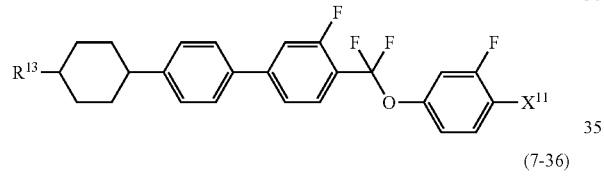
(7-36)
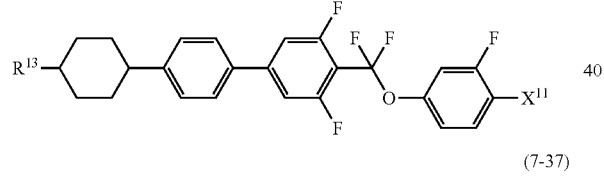
(7-37)
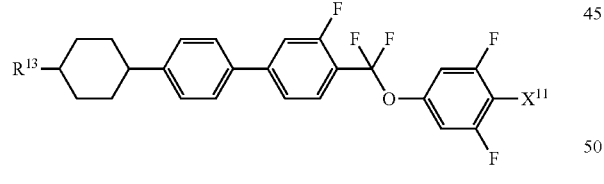
(7-38)
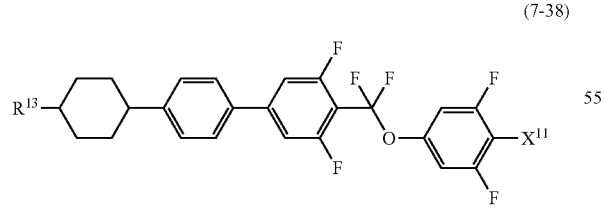
(7-39)
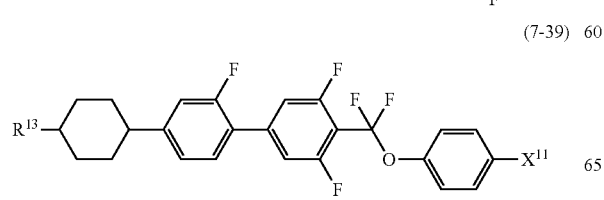
(7-40)
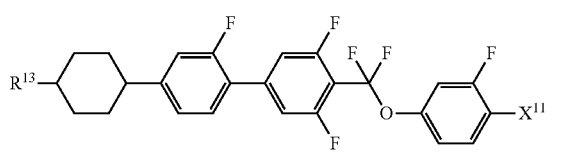
(7-41)
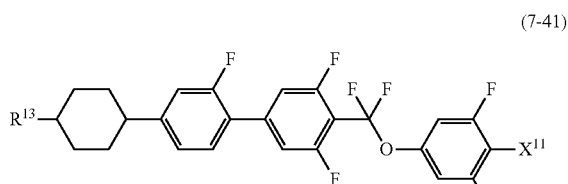
(7-42)
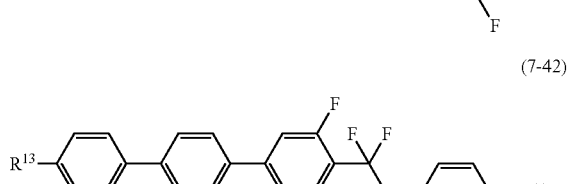
(7-43)
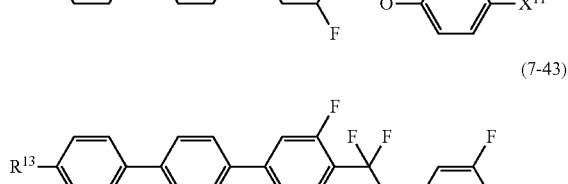
(7-44)
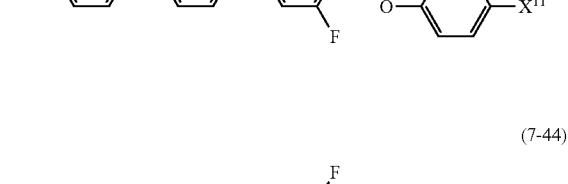
(7-45)
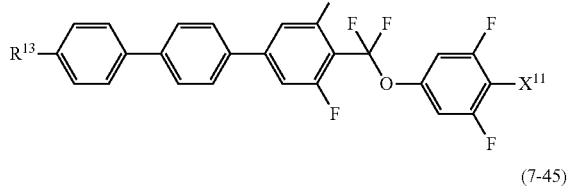
(7-46)
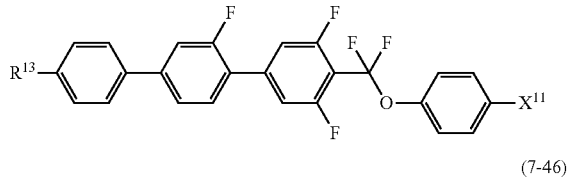
(7-47)
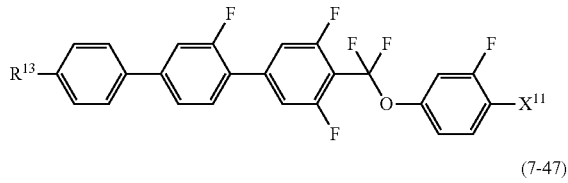
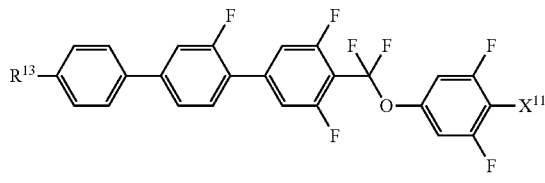

(7-48) 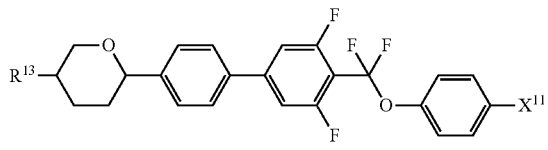

(7-49) 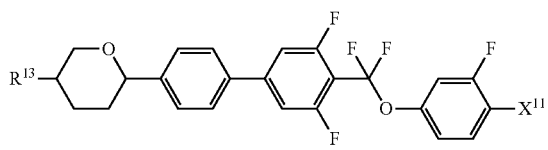

(7-50) 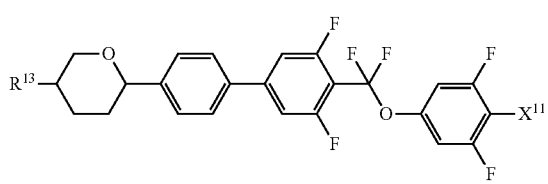

(7-51) 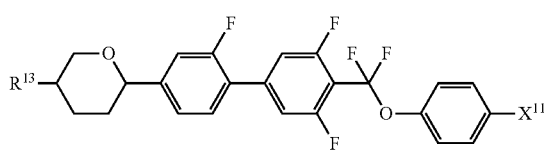

(7-52) 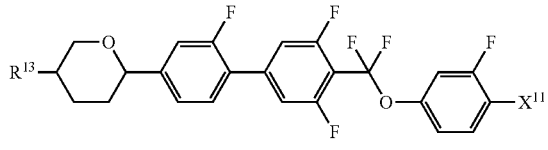

(7-53) 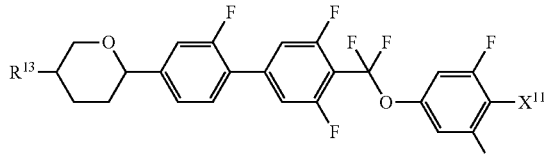

(7-54) 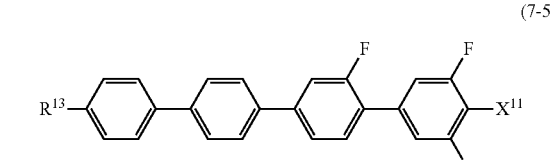

(7-55) 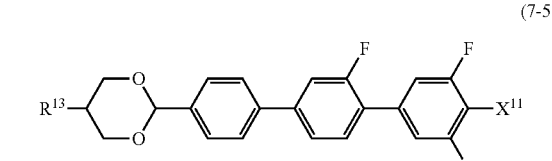

(7-56) 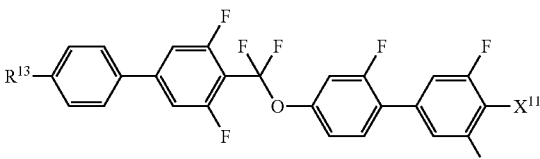

(7-57) 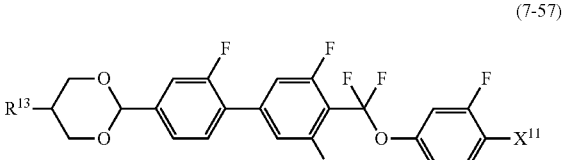

Component C has positive dielectric anisotropy and superb stability to heat, light or the like, and therefore is used when preparing a composition for a mode such as PS-IPS, PS-FFS and PSA-OCB. A content of component C is, based on the weight of the liquid crystal composition, suitably in the range of approximately 1% by weight to approximately 99% by weight, preferably in the range of approximately 10% by weight to approximately 97% by weight, and further preferably in the range of approximately 40% by weight to approximately 95% by weight. When component C is added to a composition having negative dielectric anisotropy, a content of component C is preferably in the range of approximately 30% by weight or less based on the weight of the liquid crystal composition. Addition of component C allows adjustment of an elastic constant of the composition and adjustment of a voltage-transmittance curve of a device.

Component D includes compound (8) in which a right-terminal group is —C≡N or —C≡C—C≡N. Specific preferred examples of component D include compounds (8-1) to (8-64). In the compounds of component D, $R^{14}$ is alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine; and $X^{12}$ is —C≡N or —C≡C—C≡N.

(8-1) 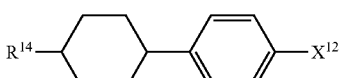

(8-2) 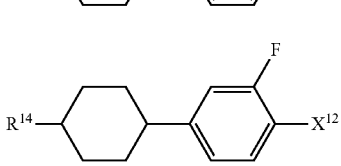

(8-3) 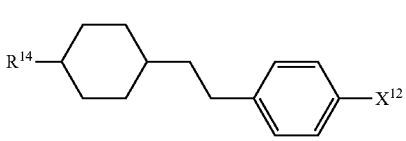

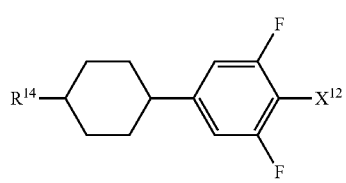 (8-4)
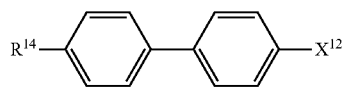 (8-5)
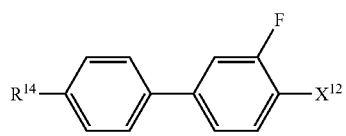 (8-6)
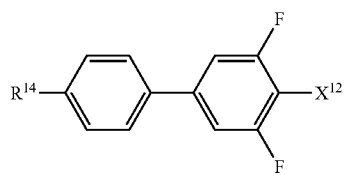 (8-7)
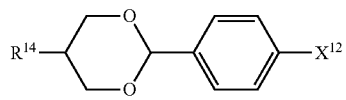 (8-8)
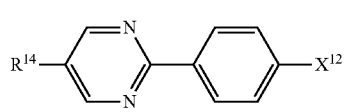 (8-9)
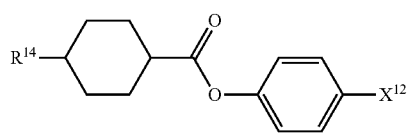 (8-10)
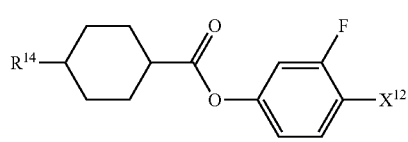 (8-11)
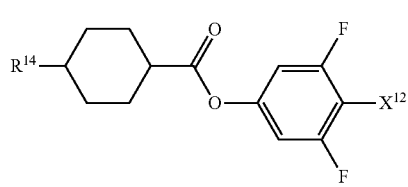 (8-12)
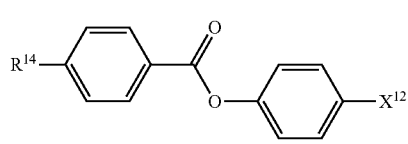 (8-13)
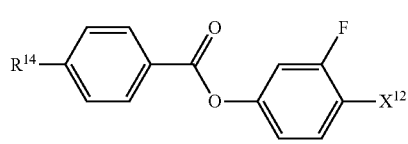 (8-14)
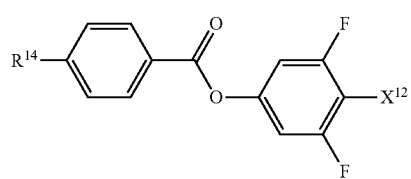 (8-15)
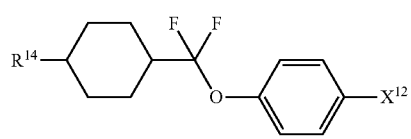 (8-16)
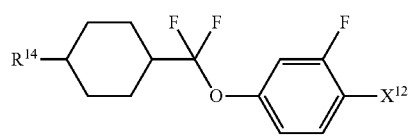 (8-17)
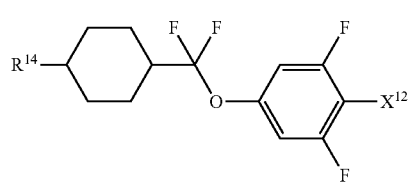 (8-18)
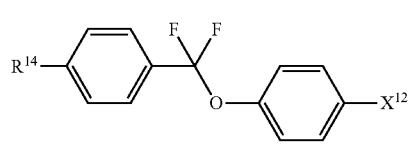 (8-19)
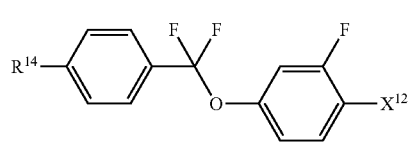 (B-20)
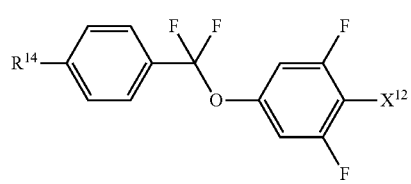 (B-21)
 (B-22)
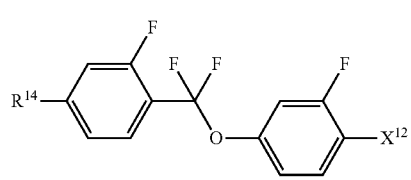 (B-23)

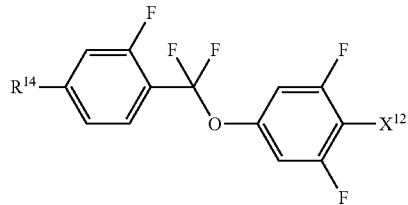 (B-24)
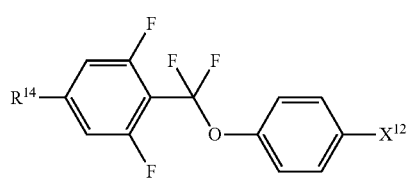 (B-25)
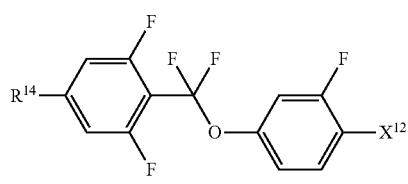 (B-26)
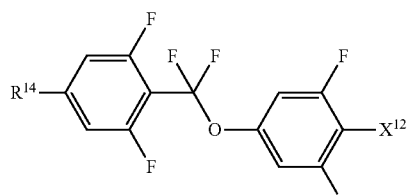 (B-27)
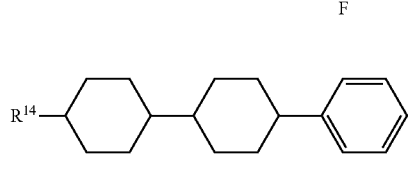 (B-28)
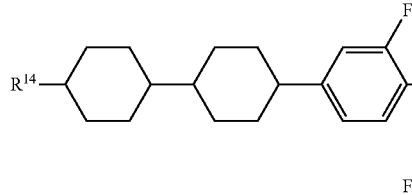 (B-29)
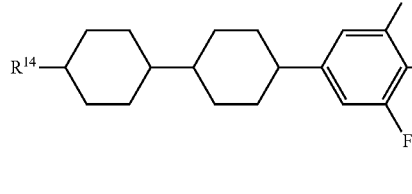 (B-30)
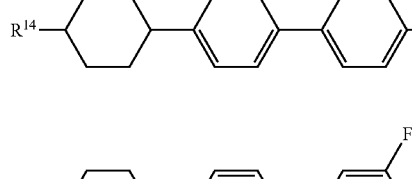 (B-31)
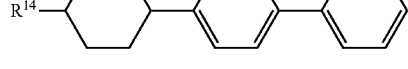 (B-32)
(B-33)
(B-34)
(B-35)
(B-36)
(B-37)
(B-38)
(B-39)
(B-40)
(B-41)
(B-42)

(B-43)
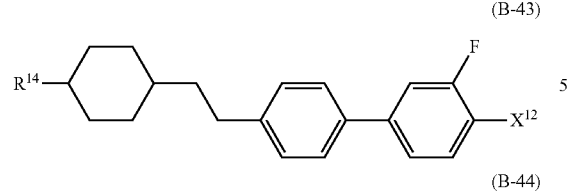
(B-44)
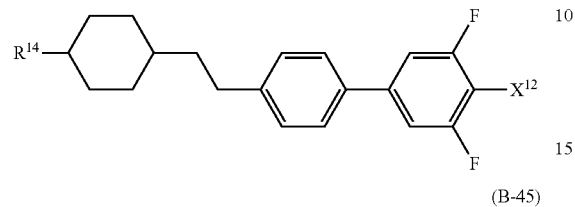
(B-45)
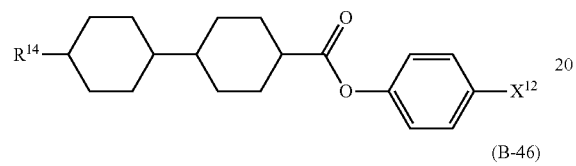
(B-46)
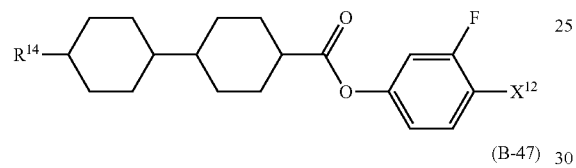
(B-47)
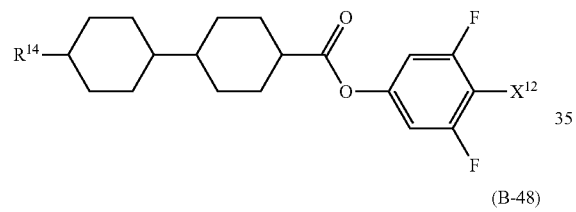
(B-48)
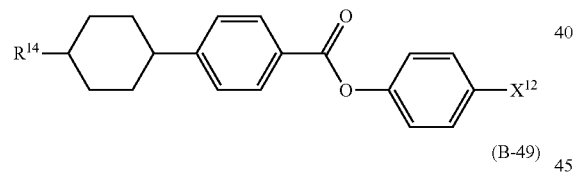
(B-49)
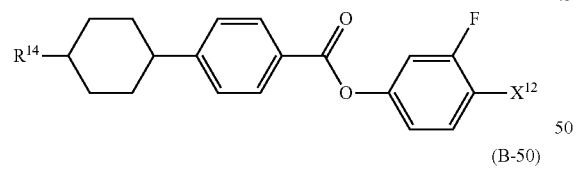
(B-50)
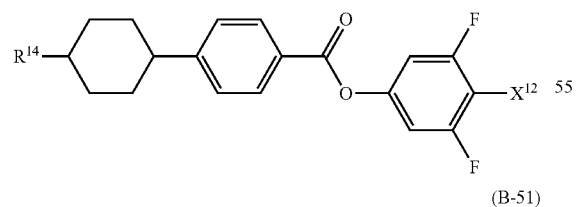
(B-51)
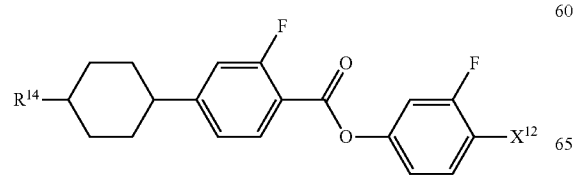
(B-52)
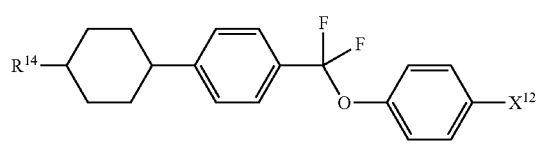
(B-53)
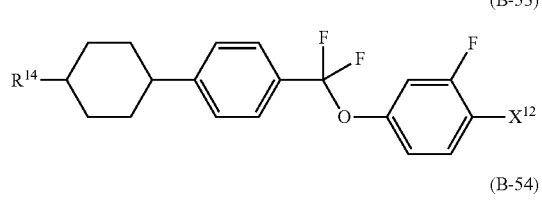
(B-54)
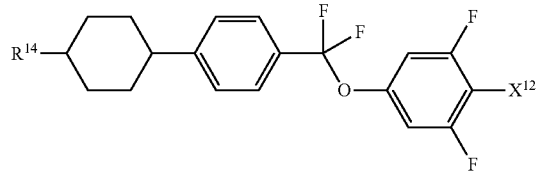
(B-55)
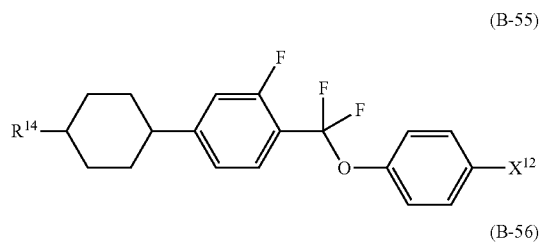
(B-56)
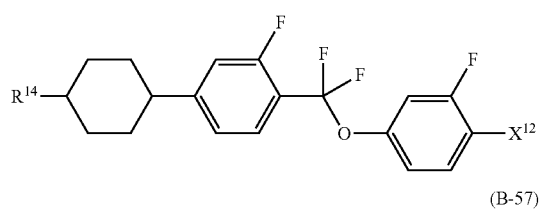
(B-57)
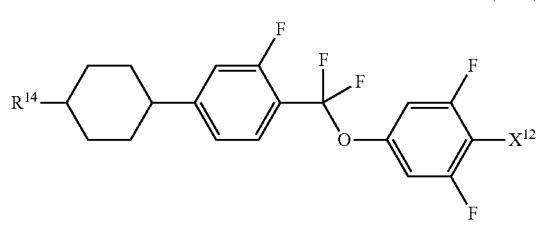
(B-58)
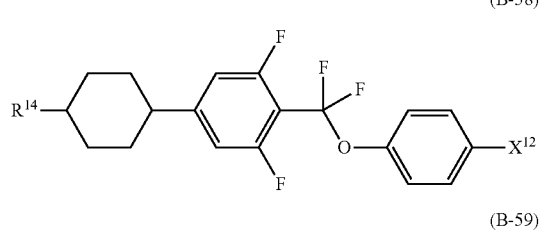
(B-59)
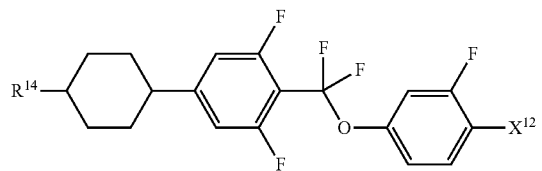

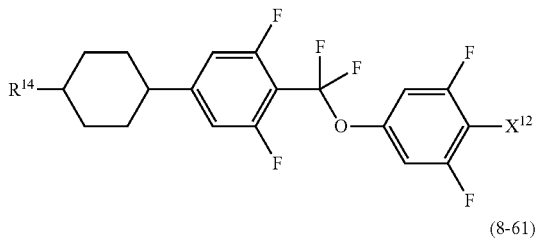

(B-60)

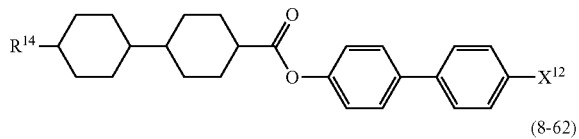

(8-61)

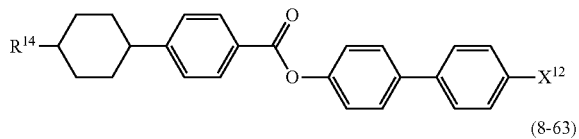

(8-62)

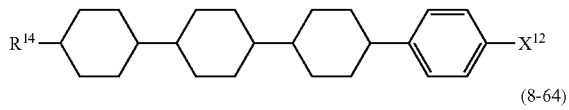

(8-63)

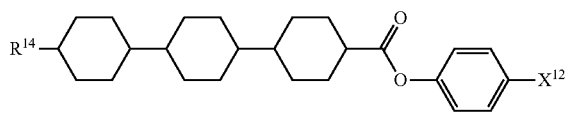

(8-64)

Component D has a large value of positive dielectric anisotropy, and therefore is mainly used when preparing a composition for a mode such as PS-TN. Dielectric anisotropy of the composition can be increased by adding component D. Component D is effective in extending the temperature range of the liquid crystal phase, adjusting the viscosity or adjusting the optical anisotropy. Component D is also useful for adjustment of the voltage-transmittance curve of the device.

When preparing the composition for the mode such as PS-TN, a content of component D is, based on the weight of the liquid crystal composition, suitably in the range of approximately 1% by weight to approximately 99% by weight, preferably in the range of approximately 10% by weight to approximately 97% by weight, and further preferably in the range of approximately 40% by weight to approximately 95% by weight. When component D is added to a composition having negative dielectric anisotropy, a content of component D is preferably in the range of approximately 30% by weight or less based on the weight of the liquid crystal composition. Addition of component D allows adjustment of the elastic constant of the composition and adjustment of the voltage-transmittance curve of the device.

The polymerizable composition is prepared by method for dissolution of required components at temperature higher than room temperature, or the like. According to an application, an additive may be added to the composition. Examples of the additives include an optically active compound, an antioxidant, an ultraviolet light absorber, a light stabilizer, a heat stabilizer, an antifoaming agent, a polymerization initiator and a polymerization inhibitor. Such additives are well known to those skilled in the art, and are described in literature.

The optically active compound is effective in inducing helical structure to provide liquid crystal molecules with a required twist angle, thereby preventing inverted twist. Addition of the optically active compound allows adjustment of helical pitch thereof. Two or more optically active compounds may be added thereto for the purpose of adjusting temperature dependence of the helical pitch. Specific preferred examples of the optically active compound include compounds (Op-1) to (Op-18) described below. In compound (Op-18), ring J is 1,4-cyclohexylene or 1,4-phenylene, and $R^{28}$ is alkyl having 1 to 10 carbons.

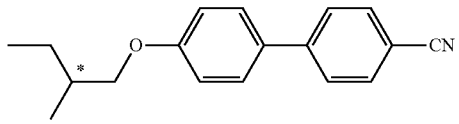  (Op-1)

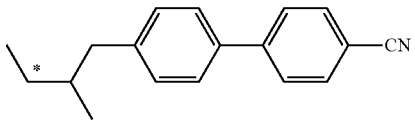  (Op-2)

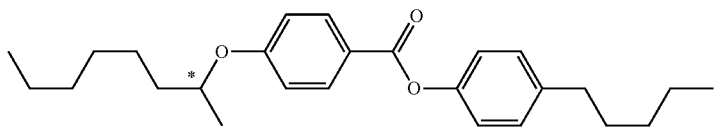  (Op-3)

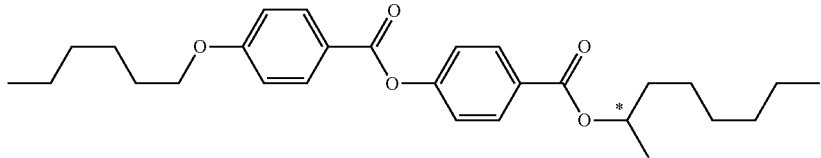  (Op-4)

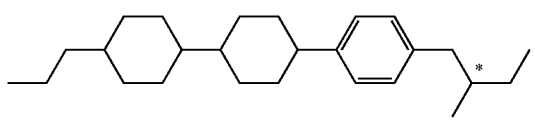  (Op-5)

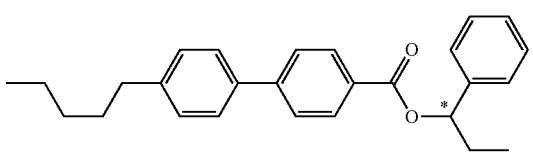  (Op-6)

(Op-7)
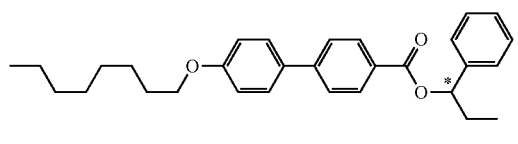
(Op-8)
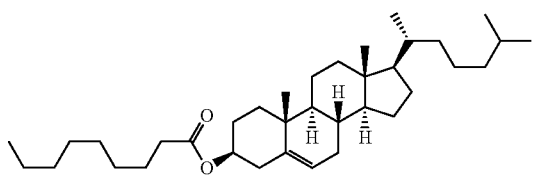
(Op-9)
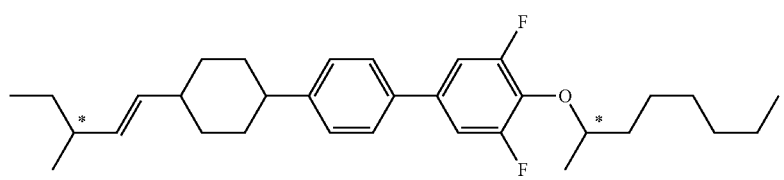
(Op-10)
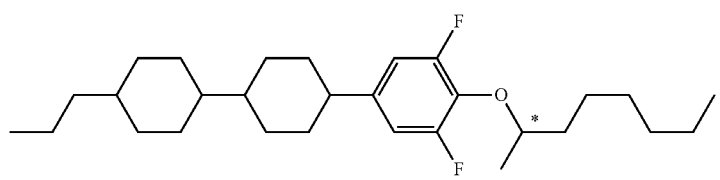
(Op-11)
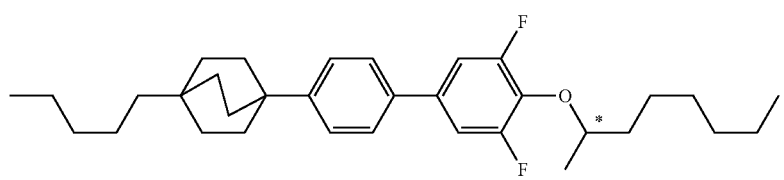
(Op-12)
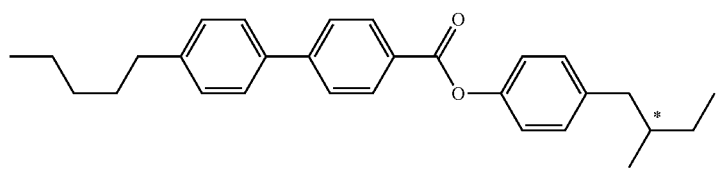
(Op-13)
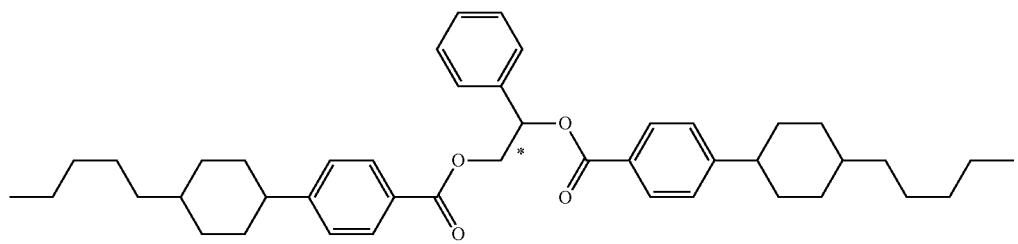
(Op-14)
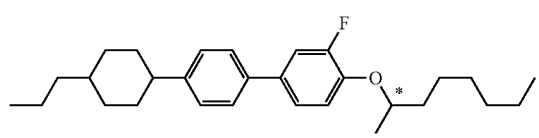
(Op-15)
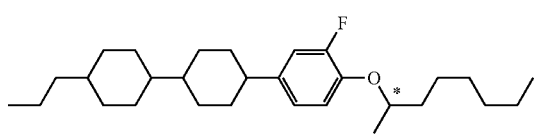
(Op-16)
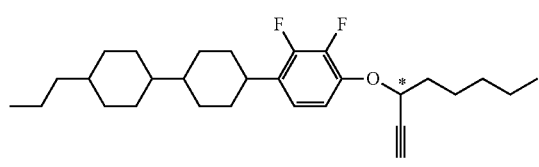
(Op-17)
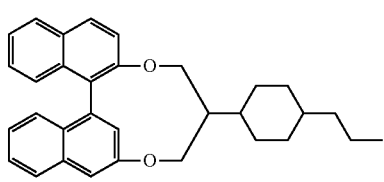

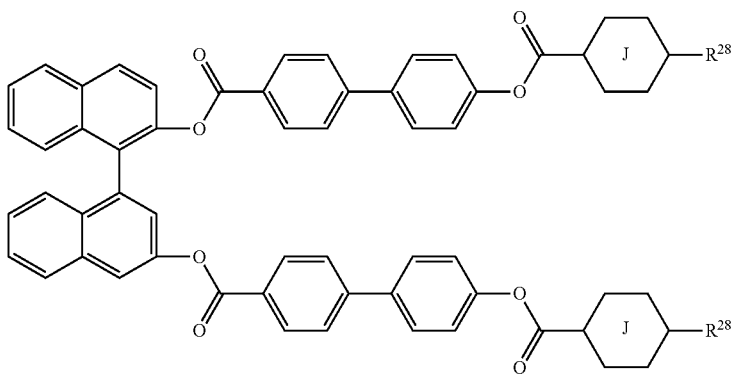
(Op-18)

The antioxidant is effective in order to maintain a large voltage holding ratio. Specific preferred examples of the antioxidants include compounds (AO-1) and (AO-2) described below; IRGANOX 415, IRGANOX 565, IRGANOX 1010, IRGANOX 1035, IRGANOX 3114 and IRGANOX 1098 (trade name: BASF SE). The ultraviolet light absorber is effective in preventing a decrease in the maximum temperature. Preferred examples of the ultraviolet light absorbers include a benzophenone derivative, a benzoate derivative and a triazole derivative. Specific examples include compounds (AO-3) and (AO-4) described below; TINUVIN 329, TINUVIN P, TINUVIN 326, TINUVIN 234, TINUVIN 213, TINUVIN 400, TINUVIN 328 and TINUVIN 99-2 (trade name: BASF SE); 1,4-diazabicyclo[2.2.2]octane (DABCO).

The light stabilizer such as an amine having steric hindrance is preferred in order to maintain a large voltage holding ratio. Specific preferred examples of the light stabilizers include compounds (AO-5) and (AO-6) described below, TINUVIN 144, TINUVIN 765 and TINUVIN 770DF (trade name: BASF SE). The heat stabilizer is also effective in order to maintain a large voltage holding ratio, and specific preferred examples include IRGAFOS 168 (trade name: BASF SE). The antifoaming agent is effective in order to prevent foam formation. Preferred examples of the antifoaming agent include dimethyl silicone oil and methylphenyl silicone oil.

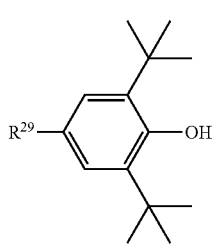
(AO-1)

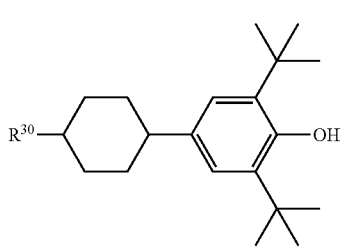
(AO-2)

(AO-3)

(AO-4)

(AO-5)

(AO-6)

In compound (AO-1), $R^{29}$ is alkyl having 1 to 20 carbons, alkoxy having 1 to 20 carbons, —$COOR^{32}$ or —$CH_2CH_2COOR^{32}$, and $R^{32}$ is alkyl having 1 to 20 carbons herein. In compounds (AO-2) and (AO-5), $R^{30}$ is alkyl having 1 to 20 carbons. In compound (AO-5), $R^{31}$ is hydrogen, methyl or O. (oxygen radical), ring K and ring L are 1,4-cyclohexylene or 1,4-phenylene, and x is 0, 1 or 2.

4. Liquid Crystal Composite

Compound (1) has suitable polymerization reactivity, high conversion and high compatibility in the liquid crystal composition. A liquid crystal composite is formed by polymerizing the polymerizable composition containing compound (1) and the liquid crystal composition. Compound (1) forms the polymer in the liquid crystal composition by polymerization of the composition. The polymer is effective in generating pretilt in the liquid crystal molecules. The polymerization is preferably performed at temperature at which the polymerizable composition exhibits the liquid crystal phase. The polymerization is triggered by heat, light or the like. A preferred reaction includes photopolymerization. The photopolymerization performed at 100° C. or lower is preferred in order to prevent thermopolymerization at the same time. The polymerization may be allowed in a state in which an electric field or a magnetic field is applied.

The polymerization reactivity and the conversion of compound (1) can be adjusted. Compound (1) is suitable for radical polymerization. Adding the polymerization initiator, compound (1) can be rapidly polymerized. Decrease of amount of remaining compound (1) is achieved by optimization of reaction temperature. Specific examples of a photoradical polymerization initiator include TPO, 1173 and 4265 from Darocur series, and 184, 369, 500, 651, 784, 819, 907, 1300, 1700, 1800, 1850 and 2959 from Irgacure series of BASF SE.

Additional examples of the photoradical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole-mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a 2,4-diethylxanthone-methyl p-dimethylaminobenzoate mixture and a benzophenone-methyltriethanolamine mixture.

After adding the photoradical polymerization initiator to the polymerizable composition, under a state in which the electric field is applied to the resulting material, the polymerization can be performed by ultraviolet light. However, an unreacted polymerization initiator or a decomposition product of the polymerization initiator might make display the defective such as image persistence. In order to avoid such the defectives, photopolymerization may be performed without adding the polymerization initiator. A preferred wavelength of irradiating light is in the range of approximately 150 nanometers to approximately 500 nanometers. A further preferred wavelength is in the range of approximately 250 nanometers to approximately 450 nanometers, and a most preferred wavelength is in the range of approximately 300 nanometers to approximately 400 nanometers.

When storing the polymerizable compound, the polymerization inhibitor may be added thereto in order to inhibit the polymerization. The polymerizable compound is ordinarily added to the composition without removing the polymerization inhibitor. Examples of the polymerization inhibitor include hydroquinone, a hydroquinone derivative such as methylhydroquinone, 4-tert-butylcatechol, 4-methoxyphenol and phenothiazine.

5. Liquid Crystal Display Device

An effect of the polymer in the liquid crystal display device is interpreted as described below. The polymerizable composition is a mixture of the liquid crystal compound, the polymerizable compound and so forth. Applying the electric field to the composition causes alignment of the liquid crystal molecules in the direction of the electric field. A molecules of the polymerizable compound is also aligned in an identical direction of the alignment. In the state, the polymerizable compound is polymerized by irradiating ultraviolet light. As a result, a polymer network is formed in the polymerizable composition. The liquid crystal molecules in a state of being aligned in the direction of the electric field are stabilized by effect of the network. Even when the electric field is removed, the effect is maintained. Accordingly, a response time of the device is decreased.

The polymerizable composition is preferably polymerized in the display device. One example is as described below. A display device having two glass substrates composed of transparent electrodes and an alignment film. A polymerizable composition containing compound (1), a liquid crystal composition, an additive and so forth is prepared as a component. The composition is injected into the display device. The display device is irradiated by ultraviolet light while applying the electric field to polymerize compound (1). A liquid crystal composite is formed by the polymerization. A liquid crystal display device having the liquid crystal composite is easily produced by the method. Rubbing treatment to the alignment film may not be required in the method. In addition, a method of stabilizing the liquid crystal molecules in a state without the electric field may be adopted.

When the amount of addition of the polymerizable compound is in the range of approximately 0.1% by weight to approximately 2% by weight based on the weight of the liquid crystal composition, a liquid crystal display device having the PSA mode is prepared. The device having the PSA mode can be driven by a driving mode such as active matrix (AM) and passive matrix (PM). Such a device can be applied to any mode of a reflective mode, a transmissive mode and a transflective mode. An increase in the amount of addition of the polymerizable compound also allows preparation of a device having polymer dispersed mode.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be described in more detail by way of Examples. The invention is not limited by the Examples. The invention includes a mixture of a composition in Example 1 and a composition in Example 2. The invention also includes a mixture in which at least two compositions in Examples were mixed. A compound prepared was identified by a method such as an NMR analysis. Physical properties of the compound, the composition and the device were measured by the methods as described below.

1. Example of Compound (1)

NMR Analysis

For measurement, DRX-500 made by Bruker BioSpin Corporation was used. In $^1$H-NMR measurement, a sample was dissolved in a deuterated solvent such as CDCl3, and measurement was carried out under conditions of room temperature, 500 MHz and 16 times of accumulation. Tetramethylsilane was used as an internal standard. $^{19}$F-NMR measurement was carried out using $CFCl_3$ as an internal standard and accumulated in 24 times. In the explanation of nuclear magnetic resonance spectra, symbols s, d, t, q, quin, sex, m and br stand for a singlet, a doublet, a triplet, a quartet, a quintet, a sextet, a multiplet and being broad, respectively.

HPLC Analysis

For measurement, Prominence (LC-20 AD; SPD-20A) made by Shimadzu Corporation was used. As a column, YMC-Pack ODS-A (length: 150 mm, bore: 4.6 mm, particle diameter: 5 μm) made by YMC GmbH was used. As an eluate, acetonitrile and water were appropriately mixed and used. As a detector, a UV detector, an RI detector, a CORONA detector or the like was appropriately used. When the UV detector was used, a detection wavelength was adjusted to 254 nm. A sample was dissolved in acetonitrile and prepared to be a 0.1 wt % solution, and 1 microliter of the solution was injected into a sample injector. As a recorder, C-R7Aplus made by Shimadzu Corporation was used.

Ultraviolet-Visible Spectrophotometry

For measurement, PharmaSpec UV-1700 made by Shimadzu Corporation was used. A detection wavelength was adjusted to 190 to 700 nm. A sample was dissolved in acetonitrile and prepared to be a 0.01 mmol/L solution, and was measured in a quartz cell (light path length: 1 cm).

Sample for Measurement

When phase structure and a transition temperature (a clearing point, a melting point, a polymerization starting temperature or the like) were measured, a liquid crystal compound itself was used as a sample. When physical properties such as a maximum temperature of a liquid crystal compound, viscosity, optical anisotropy and dielectric anisotropy were measured, a mixture prepared by mixing the compound with a base liquid crystal was used as a sample. When the physical properties of a liquid crystal composition were measured, a liquid crystal composition itself was used as a sample.

Measuring Method

The physical properties were measured according to the methods described below. Most of the measuring methods are applied as described in the Standard of the Japan Electronics and Information Technology Industries Association (JEITA EIAJ ED-2521B) discussed and established by JEITA, or modified thereon. No thin film transistor (TFT) was attached to a TN device used for measurement.

(1) Phase Structure

A sample was placed on a hot plate of a melting point apparatus (FP-52 Hot Stage made by Mettler-Toledo International Inc.) equipped with a polarizing microscope, and states of phase and changes thereof were observed with the polarizing microscope while the sample was heated at a rate of 3° C. per minute, and a kind of the phase was identified.

(2) Transition Temperature (° C.)

For measurement, a differential scanning calorimeter, Diamond DSC System, made by PerkinElmer, Inc., or a high-sensitivity differential scanning calorimeter, X-DSC7000, made by SII NanoTechnology Inc. was used. A sample was heated and then cooled at a rate of 3° C. per minute, and starting points of endothermic peaks or exothermic peaks caused by phase changes of the samples were characterized by extrapolation, and thus transition temperatures were determined. Temperatures at which compounds undergoes transition from solid to liquid crystal phase such as the smectic phase and the nematic phase were occasionally abbreviated as "minimum temperature of the liquid crystal phase." Temperature at which a compound undergoes transition from the liquid crystal phase to the isotropic liquid was occasionally abbreviated as "clearing point."

The crystals were expressed as C. When kinds of the crystals were distinguishable, each of the crystals were expressed as $C_1$ or $C_2$. The smectic phase and the nematic phase was expressed as S and N, respectively. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. A transition temperature was expressed such as "C 50.0 N 100.0 I", for example. The expression indicates that a transition temperature from the crystals to the nematic phase is 50.0° C., and a transition temperature from the nematic phase to the liquid is 100.0° C.

(3) Maximum Temperature of Nematic Phase ($T_{NI}$ or NI; ° C.)

A sample was placed on a hot plate in a melting point measuring apparatus equipped with a polarizing microscope and was heated at a rate of 1° C. per minute. Temperature when part of the sample began to change from a nematic phase to an isotropic liquid was measured. A higher limit of a temperature range of the nematic phase may be occasionally abbreviated as "maximum temperature." When the sample was a mixture of a liquid crystal compound and the base liquid crystal, the maximum temperature was expressed in terms of a symbol $T_{NI}$. When the sample was a mixture of the liquid crystal compound and a compound having components such as component B, C and D, the maximum temperature was expressed in terms of a symbol NI.

(4) Minimum Temperature of Nematic Phase ($T_c$; ° C.)

Samples each having a nematic phase were kept in freezers at temperatures of 0° C., −10° C., −20° C., −30° C. and −40° C. for 10 days, and then liquid crystal phases were observed. For example, when the sample maintained the nematic phase at −20° C. and changed to the crystals or the smectic phase at −30° C., $T_c$ was expressed as $T_c \leq −20°$ C. A lower limit of the temperature range of the nematic phase is occasionally abbreviated as "minimum temperature."

(5) Viscosity (Bulk Viscosity; η; Measured at 20° C.; mPa·s)

Viscosity was measured using a cone-plate (E type) rotational viscometer made by Tokyo Keiki, Inc.

(6) Optical Anisotropy (Refractive Index Anisotropy; Δn; Measured at 25° C.)

Measurement was carried out by an Abbe refractometer having a polarizing plate mounted on an ocular, when a wavelength of the light for measurements was set at 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy (Δn) was calculated from an equation: Δn=n∥−n⊥.

(7) Specific Resistance (ρ; Measured at 25° C.; Ωcm)

Into a vessel equipped with electrodes, 1.0 milliliter of sample was injected. A DC voltage (10 V) was applied to the vessel, and a DC current after 10 seconds of the applying was measured. A specific resistance was calculated from the following equation: (specific resistance)={(voltage)×(electric capacity of a vessel)}/{(direct current)×(dielectric constant of vacuum)}.

(8) Voltage Holding Ratio (VHR-1; Measured at 25° C.; %)

A TN device used for measurement had a polyimide alignment film and a distance (cell gap) between two glass substrates was 5 micrometers. A sample was put in the device, and then the device was sealed with an ultraviolet-curable adhesive. The device was charged by applying a pulse voltage (60 microseconds at 5 V). A decaying voltage was measured for 16.7 milliseconds by a high-speed voltmeter, and area A between a voltage curve and a horizontal axis in a unit cycle was determined. Area B was regard as an area without decay. A voltage holding ratio is expressed in terms of a percentage of area A to area B.

(9) Voltage Holding Ratio (VHR-2; Measured at 80° C.; %)

A voltage holding ratio was measured according to method described above except that the voltage holding ratio was measured at 80° C. instead of 25° C. The obtained results were expressed using VHR-2 as symbol.

(10) Viscosity (Rotational Viscosity; γ1; Measured at 25° C.; mPa·s)

Measurement was carried out according to the method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. Voltage was applied stepwise to the device in the range of 16 V to 19.5 V at an increment of 0.5 V. After 0.2 second with no voltage application, voltage was applied repeatedly under conditions of only one rectangular wave (rectangular pulse; 0.2 second) and no application (2 seconds). A peak current and a peak time of a transient current generated by the applied voltage were measured. A value of rotational viscosity was obtained from the measured values according to calculating equation (8) on page 40 of the paper presented by M. Imai et al. As dielectric anisotropy required for the calculation, a value measured in a section of dielectric anisotropy described below was used.

(11) Dielectric Anisotropy (Δ∈; Measured at 25° C.)

A sample was put in a TN device in which a distance (cell gap) between two glass substrates was 9 micrometers and a twist angle was 80 degrees. Sine waves (10 V, 1 kHz) of voltage were applied to the device, and after 2 seconds, a dielectric constant (∈∥) in the major axis direction of liquid crystal molecules was measured. Sine waves (0.5 V, 1 kHz) of voltage were applied to the device, and after 2 seconds, a dielectric constant (∈⊥) in the minor axis direction of the liquid crystal molecules was measured. A value of dielectric anisotropy was calculated from an equation: Δ∈=∈∥–∈⊥.

(12) Elastic Constant (K; Measured at 25° C.; pN)

HP4284A LCR Meter made by Yokogawa-Hewlett-Packard Co. was used for measurement. A sample was put in a horizontal alignment device in which a distance (cell gap) between two glass substrates was 20 micrometers. An electric charge of 0 V to 20 V was applied to the device, and electrostatic capacity and applied voltage were measured. The measured values of electrostatic capacity (C) and applied voltage (V) were fitted to equation (2.98) and equation (2.101) on page 75 of "Liquid Crystal Device Handbook" (Ekisho Debaisu Handobukku in Japanese; The Nikkan Kogyo Shimbun, Ltd.) and values of $K_{11}$ and $K_{33}$ were obtained from equation (2.99). Next, $K_{22}$ was calculated using the previously determined values of $K_{11}$ and $K_{33}$ in formula (3.18) on page 171. Elastic constant K is a mean value of the thus determined $K_{11}$, $K_{22}$ and $K_{33}$.

(13) Threshold Voltage (Vth; Measured at 25° C.; V)

An LCD-5100 luminance meter made by Otsuka Electronics Co., Ltd. was used for measurement. A light source was a halogen lamp. A sample was put in a normally white mode TN device in which a distance (cell gap) between two glass substrates was 0.45/An (m) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which 100% of transmittance was regarded as a maximum amount of light and 0% of transmittance was regarded as a minimum amount of light. A threshold voltage is expressed in terms of a voltage at 90% transmittance.

(14) Response Time (τ; Measured at 25° C.; Ms)

An LCD-5100 luminance meter made by Otsuka Electronics Co., Ltd. was used for measurement. A light source was a halogen lamp. A low-pass filter was set at 5 kHz. A sample was put in a normally white mode TN device in which a distance (cell gap) between two glass substrates was approximately 5.0 μm and a twist angle was 80 degrees. Rectangular waves (60 Hz, 5 V, 0.5 sec) was applied to the device. On the occasion, the device was irradiated with light from a direction perpendicular to the device, and an amount of light transmitted through the device was measured. One hundred % of transmittance was regarded as a maximum amount of light and 0% of transmittance was regarded as a minimum amount of light. A rise time (τr; millisecond) was a time from 90% of transmissivity to 10% thereof. A fall time (τf: millisecond) was a time from 10% of transmissivity to 90% thereof. Response time was defined as a sum of the rise time and the fall time.

Synthesis Example 1

Synthesis of 3-((4'-(methacryloyloxy)-[1,1'-biphenyl]-4-yl)oxy)-2-butene-2-yl methacrylate (No. 10)

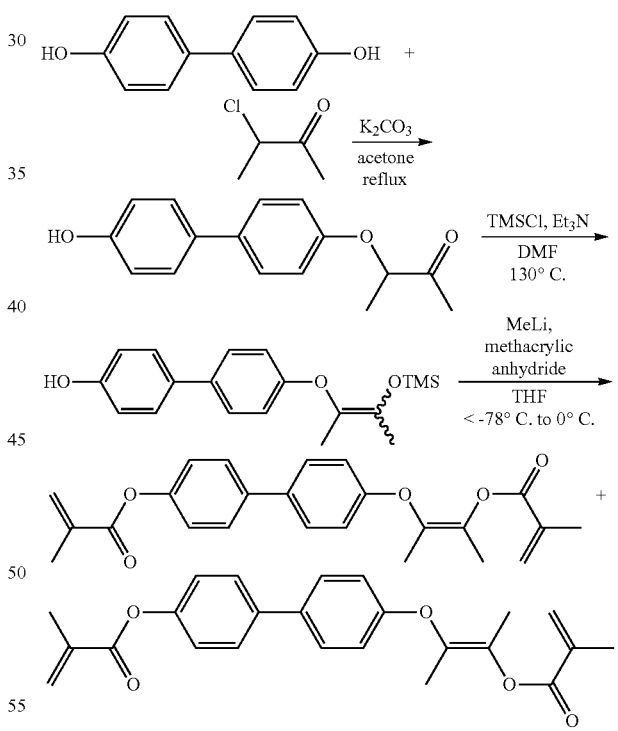

First Step

A mixture of [1,1'-biphenyl]-4,4'-diol (50.0 g, 269 mmol), potassium carbonate (37.1 g, 269 mmol) and 3-chloro-2-butanone (27.0 mL, 269 mmol) was refluxed on heating and stirring for 24 hours in acetone. The resulting reaction mixture was cooled to room temperature, and slowly poured into an aqueous solution of 11% ammonium chloride, and then an aqueous layer was extracted by ethyl acetate. Combined organic layers were washed with water and saturated brine, one by one, and dried over anhydrous magnesium sulfate, and then the resulting solution was concentrated under reduced pressure. In the resulting solid, chloroform was put, and the resulting mixture was stirred at room temperature for 30 minutes and filtered by aspirator, and the resulting filtrate was concentrated. In the resulting solid, ether and a 1 N sodium hydroxide aqueous solution was put, and the resulting mixture was stirred at room temperature for 10 minutes, and then the resulting solution was separated. An ether layer was extracted by a 0.1 N sodium hydroxide aqueous solution. Solution combined the aqueous layers was mixed with 2 N hydrochloric acid and the solution become acid, extracted by ether. Combined organic layers were washed with water and saturated brine, one by one, and then dried over anhydrous magnesium sulfate, and concentrated under reduced pressure. The resulting solid was recrystallized from hexane-acetone 3-((4'-hydroxy-[1,1'-biphenyl]-4-yl)oxy)butane-2-one (7.3 g, yield: 10.6%) was obtained.

Second Step

A mixture of 3-((4'-hydroxy-[1,1'-biphenyl]-4-yl)oxy)butane-2-one (7.20 g, 28.2 mmol), triethylamine (20.0 mL, 143.8 mmol) and chlorotrimethylsilane (10.8 mL, 85.2 mmol) in DMF was stirred at 130° C. for 24 hours. The resulting reaction mixture was cooled to room temperature, and then a saturated aqueous solution of sodium hydrogencarbonate was slowly poured thereinto, and then an aqueous layer was extracted by ether. Combined organic layers were washed with saturated aqueous solution of sodium hydrogencarbonate and saturated brine, one by one, and dried over anhydrous magnesium sulfate. A solvent was distilled off under reduced pressure and 4'-((3-((trimethylsilyl)oxy)-2-butene-2-yl)oxy)-[1,1'-biphenyl]-4-ol (12.8 g, crude yield: >99%) was obtained. The resulting composition was used for the next reaction without purification.

Third Step

To a THF solution of the crude product (12.8 g) obtained in the second step, methyllithium (1.13 M in a diethyl ether solution, 60 mL, 67.8 mmol) was slowly added dropwise at −78° C. The resulting reaction mixture was stirred at 0° C. for 30 minutes. After the resulting mixture was cooled to −78° C. again, methacrylic acid anhydride (10.5 mL, 70.5 mmol) was slowly added dropwise thereto. The resulting reaction mixture was warmed to 0° C., and poured into water. Then, an aqueous layer was extracted by ethyl acetate. Combined organic layers were washed with water, saturated aqueous solution of sodium hydrogencarbonate and saturated brine, one by one, and dried over anhydrous magnesium sulfate, and then concentrated under reduced pressure. The resulting solid was purified by a medium-pressure chromatography column and (E)-3-((4'-(methacryloyloxy)-[1,1'-biphenyl]-4-yl)oxy)-2-butene-2-yl methacrylate (2.64 g, yield: 24% (two steps)) and (Z)-3-((4'-(methacryloyloxy)-[1,1'-biphenyl]-4-yl)oxy)-2-butene-2-yl methacrylate (692 mg, yield: <6% (in two steps)) was obtained.

(E)-3-((4'-(methacryloyloxy)-[1,1'-biphenyl]-4-yl)oxy)-2-butene-2-yl methacrylate $^1$H-NMR (CDCl$_3$; δ ppm): 7.55 (brd, J=8.7 Hz, 2H), 7.52 (brd, J=8.7 Hz, 2H), 7.17 (brd, J=8.7 Hz, 2H), 7.11 (brd, J=8.7 Hz, 2H), 6.37 (brs, 1H), 6.28 (brs, 1H), 5.77 (brs, 1H), 5.72 (brs, 1H), 2.08 (dd, J=1.5, 1.0 Hz, 3H), 2.04 (dd, J=1.5, 1.0 Hz, 3H), 1.90 (q, J=1.6 Hz, 3H), 1.78 (q, J=1.6 Hz, 3H).

(Z)-3-((4'-(methacryloyloxy)-[1,1'-biphenyl]-4-yl)oxy)-2-butene-2-yl methacrylate $^1$H-NMR (CDCl$_3$; δ ppm): 7.54 (brd, J=8.7 Hz, 2H), 7.46 (brd, J=8.7 Hz, 2H), 7.17 (brd, J=8.7 Hz, 2H), 6.99 (brd, J=8.7 Hz, 2H), 6.37 (brs, 1H), 6.01 (brs, 1H), 5.77 (brs, 1H), 5.50 (brs, 1H), 2.08 (dd, J=1.5, 1.0 Hz, 3H), 2.02 (q, J=1.2 Hz, 3H), 1.92 (q, J=1.2 Hz, 3H), 1.84 (dd, J=1.5, 1.0 Hz, 3H).

Synthesis Example 2

Synthesis of 3'-fluoro-4"-((3-(methacryloyloxy)-2-butene-2-yl)oxy-[1,1':4',1"-terphenyl]-4-yl methacrylate (No. 21))

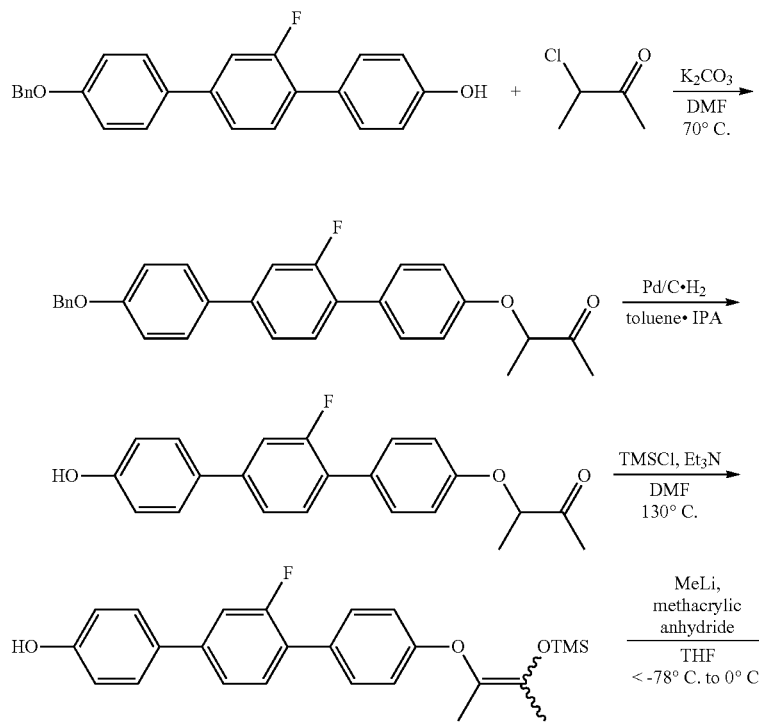

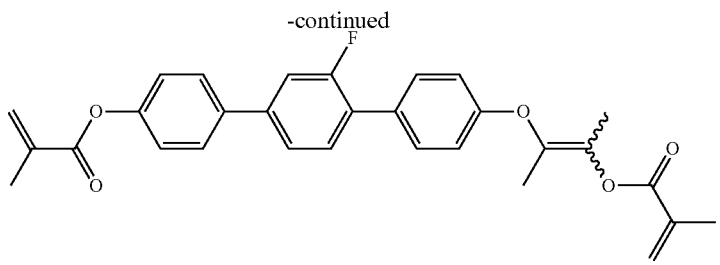

First Step

A mixture of 4"-(benzyloxy)-2'-fluoro-[1,1':4',1"-terphenyl]-4-ol (10.0 g, 27.0 mmol) prepared according to a publicly known method, potassium carbonate (3.73 g, 27.0 mmol) and 3-chloro-2-butanone (3.50 g, 32.8 mmol) was stirred at 70° C. for 15 hours in DMF. The resulting reaction mixture was cooled to room temperature, and poured into water, and then an aqueous layer was extracted by toluene. Combined organic layers were washed with an aqueous solution of sodium hydroxide, water and saturated brine, one by one, dried over anhydrous magnesium sulfate, and then concentrated under reduced pressure. The resulting solid was purified by silica gel chromatography and 3-((4"-(benzyloxy)-2'-fluoro-[1,1':4',1"-terphenyl]-4-yl)oxy)butane-2-one (10.3 g, yield: 86.4%) was obtained.

Second Step

A mixture of 3-((4"-(benzyloxy)-2'-fluoro-[1,1':4',1"-terphenyl]-4-yl)oxy)butane-2-one (10.3 g, 23.4 mmol) and 10% palladium on carbon was stirred in a mixed solvent of toluene and isopropyl alcohol under hydrogen for 12 hours. The resulting reaction mixture was filtered, and the filtrate was concentrated under reduced pressure. The resulting solid was recrystallized from a mixed toluene/heptane solvent and 3-((2'-fluoro-4"-hydroxy[1,1':4',1"-terphenyl]-4-yl)oxy)butane-2-one (7.52 g, yield: 91.8%) was obtained.

Third Step and Fourth Step

In manners which are similar to the operations in Second step and Third step in Synthesis Example 1, from 3-((2'-fluoro-4"-hydroxy[1,1':4',1"-terphenyl]-4-yl)oxy)butane-2-one (7.52 g, 21.5 mmol), a mixture of (E)-3'-fluoro-4"-(3-(methacryloyloxy)-2-butene-2-yl)oxy-[1,1':4',1"-terphenyl]-4-yl methacrylate and (Z)-3'-fluoro-4"-(3-(methacryloyloxy)-2-butene-2-yl)oxy-[1,1':4',1"-terphenyl]-4-yl methacrylate (4.89 g, yield: 46.7%) was obtained.

Synthesis Example 3

Synthesis of 7-((3-methacryloyloxy)-2-butene-2-yl)oxy)phenanthrene-2-yl methacrylate (No. 8)

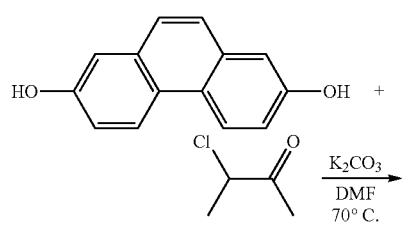

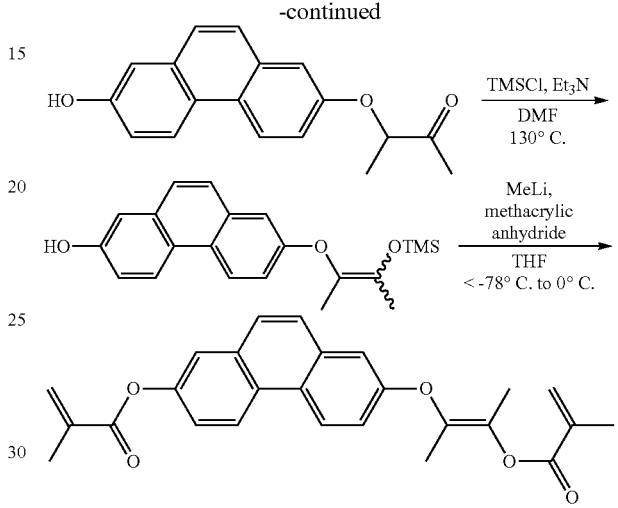

A reaction was carried out in a manner which is similar to the reaction described in Synthesis Example 1 but phenanthrene-2,7-diol prepared by publicly known method instead of [1,1'-biphenyl]-4,4'-diol in Synthesis Example 1 was used, and mixture of (E)-7-((3-methacryloyloxy)-2-butene-2-yl)oxy)phenanthrene-2-yl methacrylate and (Z)-7-((3-methacryloyloxy)-2-butene-2-yl)oxy)phenanthrene-2-yl methacrylate was obtained. The resulting mixture was purified by a medium-pressure chromatography column and (E)-7-((3-methacryloyloxy)-2-butene-2-yl)oxy)phenanthrene-2-yl methacrylate was obtained.

$^1$H-NMR (CDCl$_3$; δ ppm): 8.60 (d, J=9.0 Hz, 1H), 8.59 (d, J=9.0 Hz, 1H), 7.72 (d, J=9.0 Hz, 1H), 7.68 (d, J=9.0 Hz, 1H), 7.63 (d, J=2.5 Hz, 1H), 7.47 (d, J=2.5 Hz, 1H), 7.42 (dd, J=9.0, 2.5 Hz, 1H), 7.41 (dd, J=9.0, 2.5 Hz, 1H), 6.43 (brs, 1H), 6.32 (brs, 1H), 5.81 (brs, 1H), 5.74 (brs, 1H), 2.12 (m, 3H), 2.07 (m, 3H), 1.94 (m, 3H), 1.84 (m, 3H).

Synthesis Example 4

Synthesis of 3-((4'-(methacryloyloxy)-[1,1'-binaphthalene]-4-yl)oxy)-2-butene-2-yl methacrylate (No. 17)

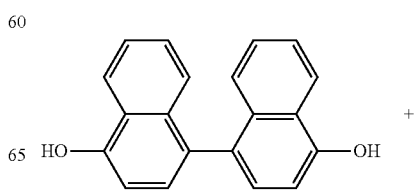

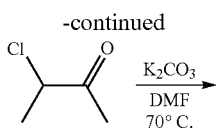

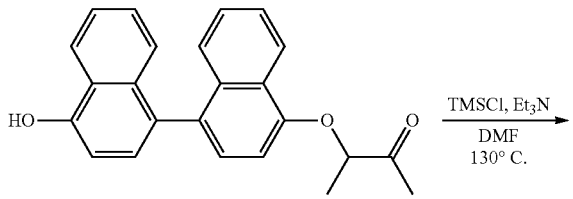

(methacryloyloxy)-[1,1'-binaphthalene]-4-yl)oxy)-2-butene-2-yl methacrylate and (Z)-3-((4'-(methacryloyloxy)-[1,1'-binaphthalene]-4-yl)oxy)-2-butene-2-yl methacrylate. The resulting mixture was purified by a medium-pressure chromatography column, and (E)-3-((4'-(methacryloyloxy)-[1,1'-binaphthalene]-4-yl)oxy)-2-butene-2-yl methacrylate was obtained.

$^1$H-NMR (CDCl$_3$; δ ppm): 8.42 (d, 1H), 7.97 (d, 1H), 7.53-7.44 (m, 4H), 7.43-7.37 (m, 3H), 7.35-7.30 (m, 2H), 7.16 (d, 1H), 6.58 (brs, 1H), 6.32 (brs, 1H), 5.91 (brs, 1H), 5.75 (brs, 1H), 2.21 (m, 3H), 2.07 (m, 3H), 2.00 (m, 3H), 1.92 (m, 3H).

Synthesis Example 5

Synthesis of 3-((4"-(methacryloyloxy)-[1,1':4',1"-terphenyl]-4-yl)oxy)-2-butene-2-yl methacrylate (No. 20)

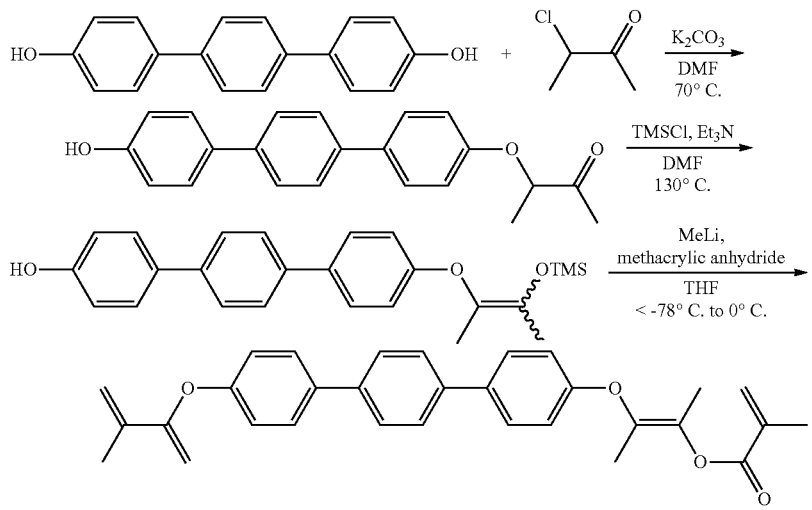

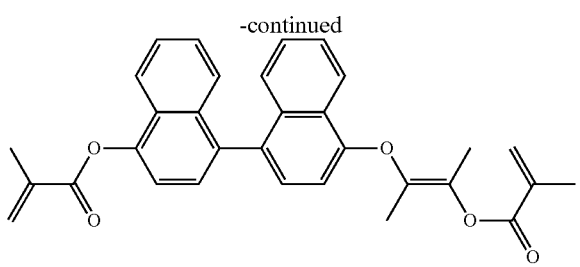

A reaction was carried out in a manner which is similar to the reaction described in Synthesis Example 1 but [1,1'-binaphthalene]-4,4'-diol prepared by publicly known method instead of changing [1,1'-biphenyl]-4,4'-diol in Synthesis Example 1 was used, and mixture of (E)-3-((4'-(methacryloyloxy)-[1,1':4',1"-terphenyl]-4-yl)oxy)-2-butene-2-yl methacrylate and (Z)-3-((4"-(methacryloiloxy)-[1,1':4',1"-terphenyl]-4-yl)oxy)-2-butene-2-yl methacrylate was obtained. The resulting mixture was purified by a medium-pressure chromatography column, and (E)-3-((4"-(methacryloyloxy)-[1,1':4',1"-terphenyl]-4-yl)oxy)-2-butene-2-yl methacrylate was obtained.

$^1$H-NMR (CDCl$_3$; δ ppm): 7.68-7.61 (m, 6H), 7.61-7.56 (m, 2H), 7.24-7.19 (m, 2H), 7.16-7.11 (m, 2H), 6.38 (brs, 1H), 6.29 (brs, 1H), 5.78 (brs, 1H), 5.73 (brs, 1H), 2.09 (m, 3H), 2.05 (m, 3H), 1.91 (m, 3H), 1.79 (m, 3H).

Compounds No. 1 to No. 63 shown below can be prepared in a manner which is similar to the methods described in Synthesis Examples 1 to 5.

75 76
(No. 1)
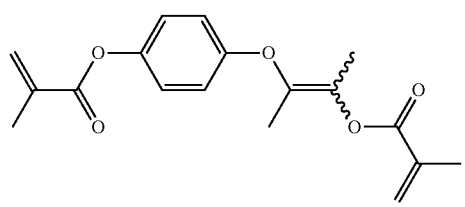
(No. 2)
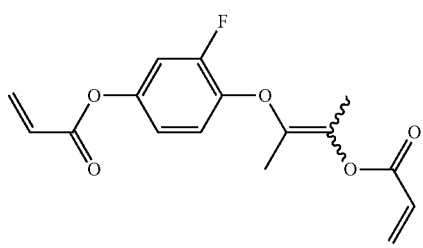
(No. 3)
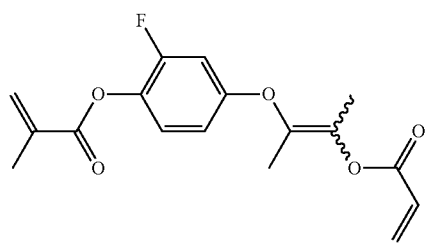
(No. 4)
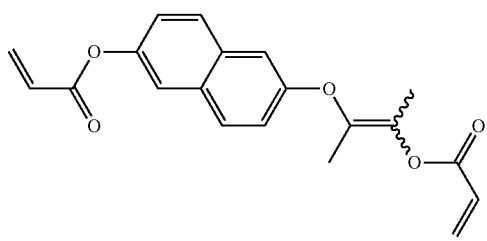
(No. 5)
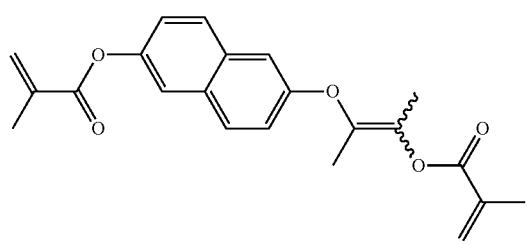
(No. 6)
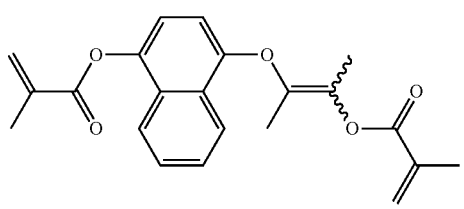
(No. 7)
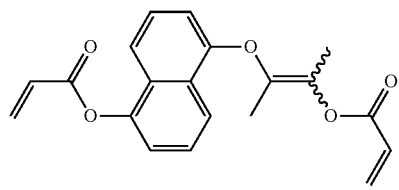
(No. 8)
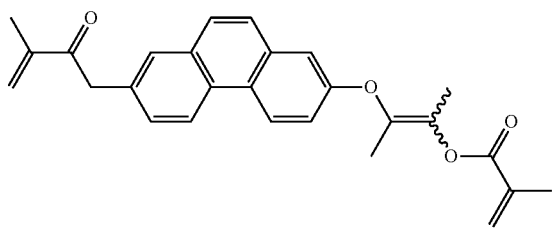
(No. 9)
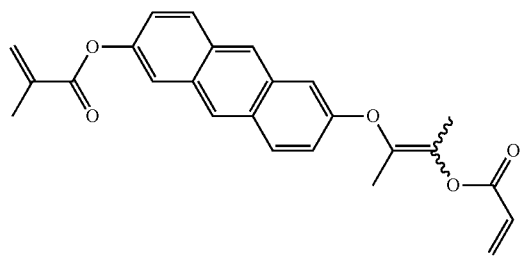
(No. 10)
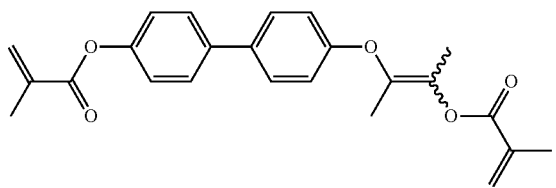
(No. 11)
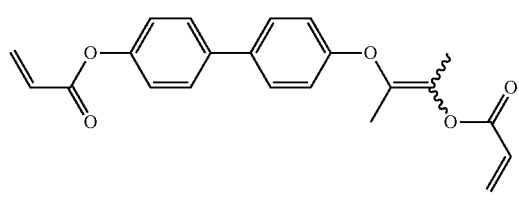
(No. 12)
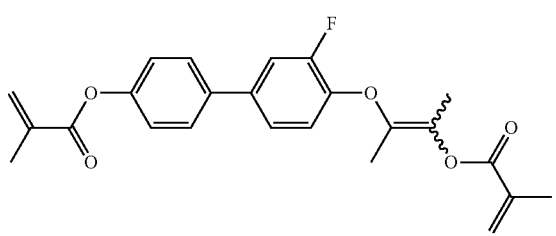

-continued
(No. 13)
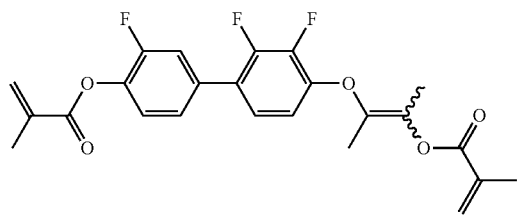
(No. 14)
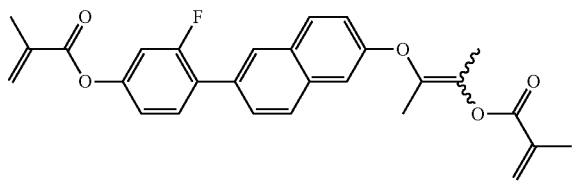
(No. 15)
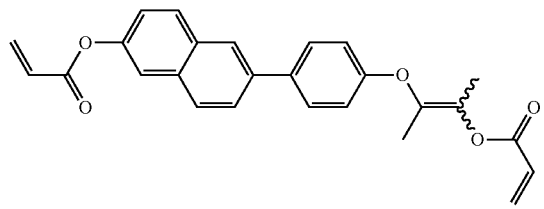
(No. 16)
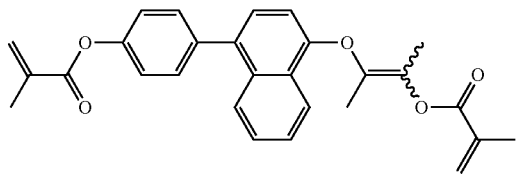
(No. 17)
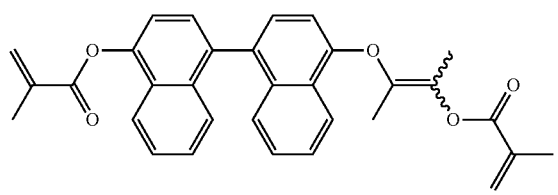
(No. 18)
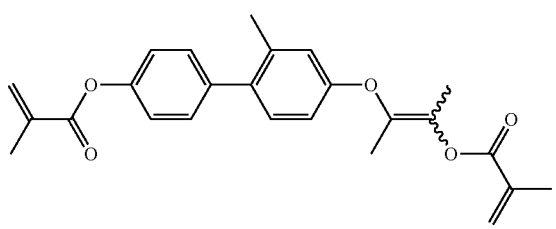
(No. 19)
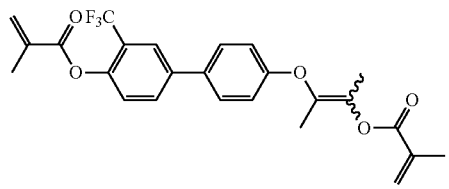
(No. 20)
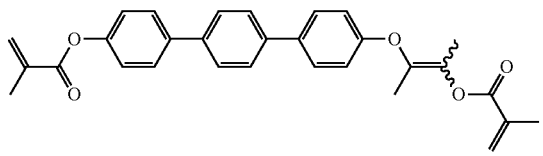
(No. 21)
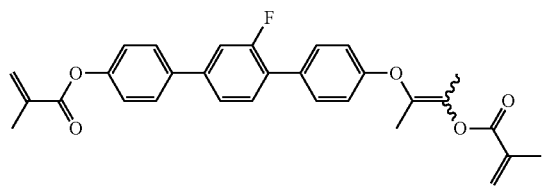
(No. 22)
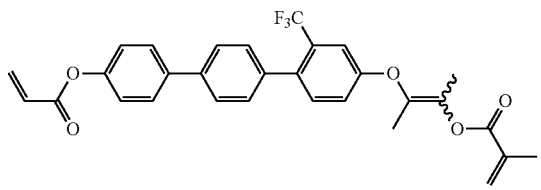
(No. 23)
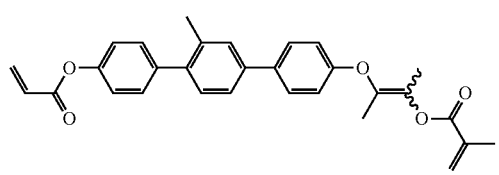
(No. 24)
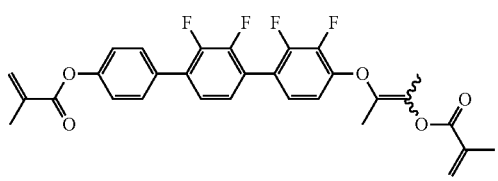
(No. 25)
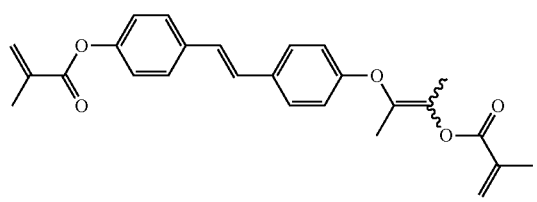
(No. 26)
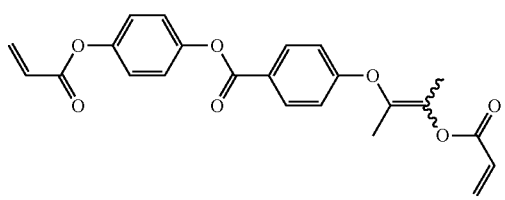

-continued
(No. 27)
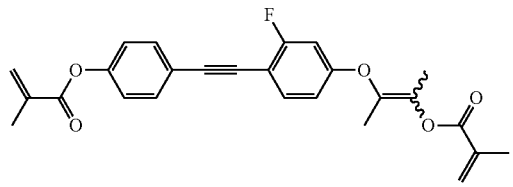
(No. 28)
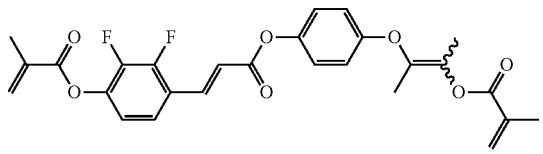
(No. 29)
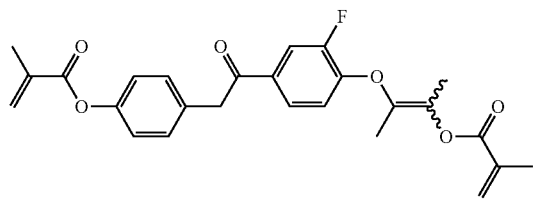
(No. 30)
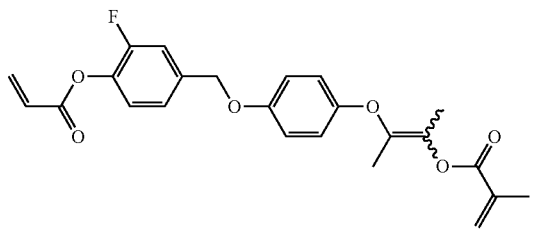
(No. 31)
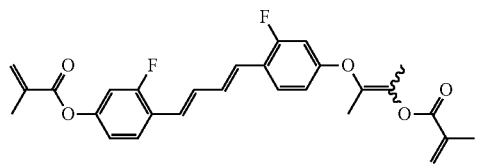
(No. 32)
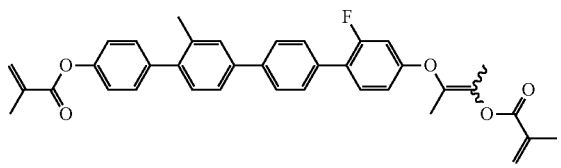
(No. 33)
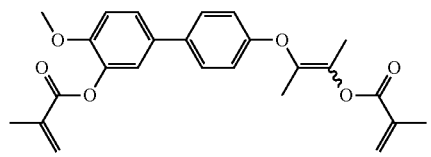
(No. 34)
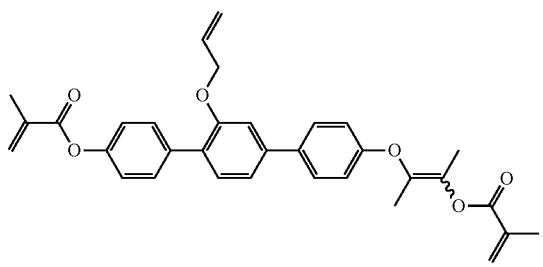
(No. 35)
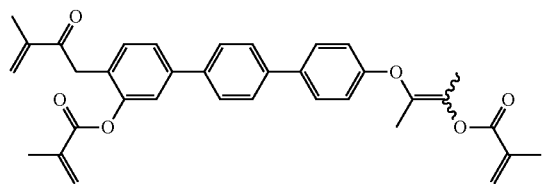
(No. 36)
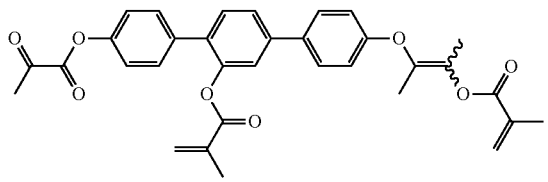
(No. 37)
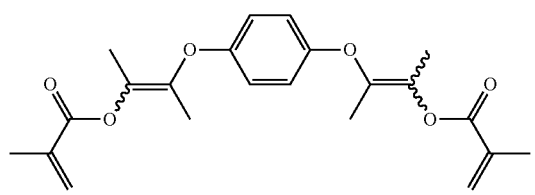
(No. 38)
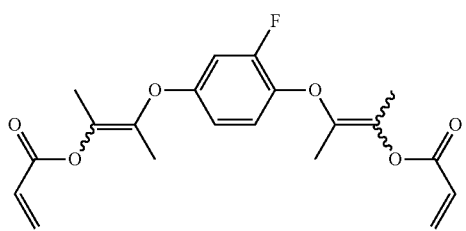
(No. 39)
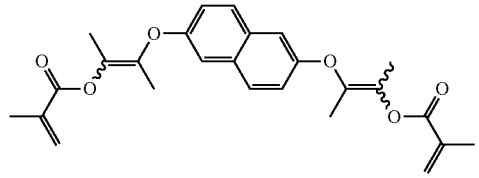
(No. 40)
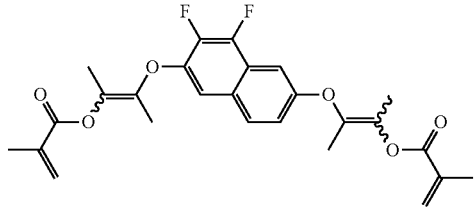

-continued
(No. 41)
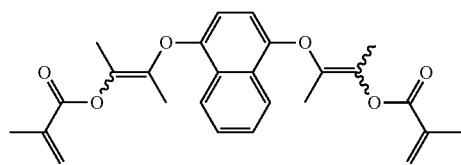
(No. 42)
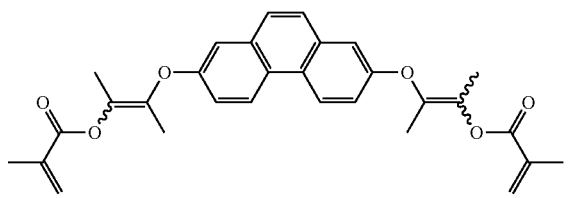
(No. 43)
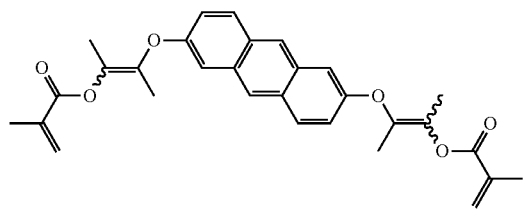
(No. 44)
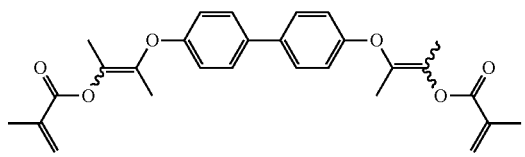
(No. 45)
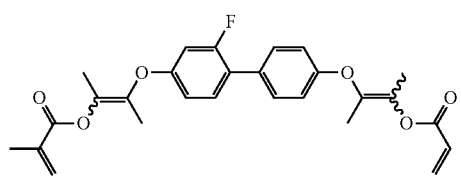
(No. 46)
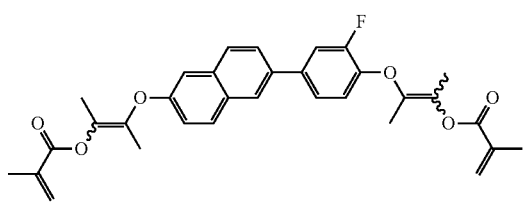
(No. 47)
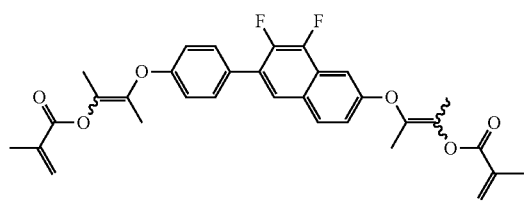
(No. 48)
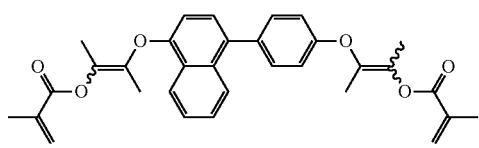
(No. 49)
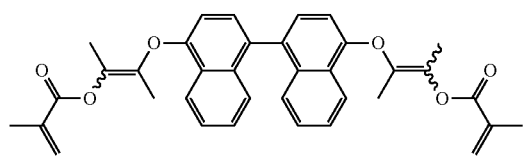
(No. 50)
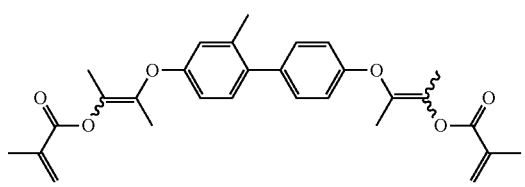
(No. 51)
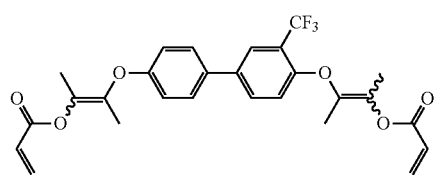
(No. 52)
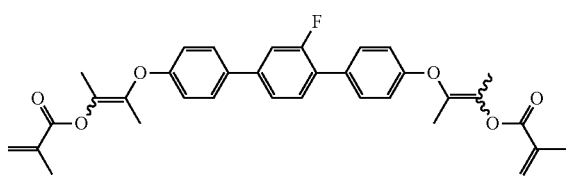
(No. 53)
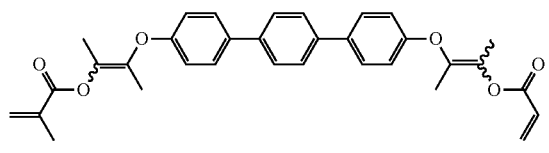
(No. 54)
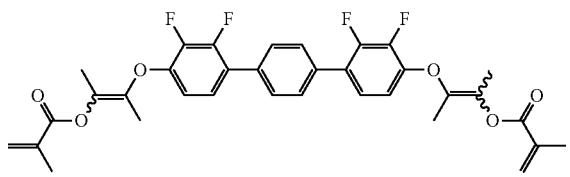

(No. 55)
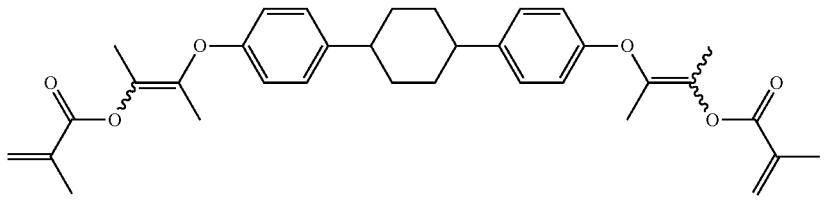
(No. 56)
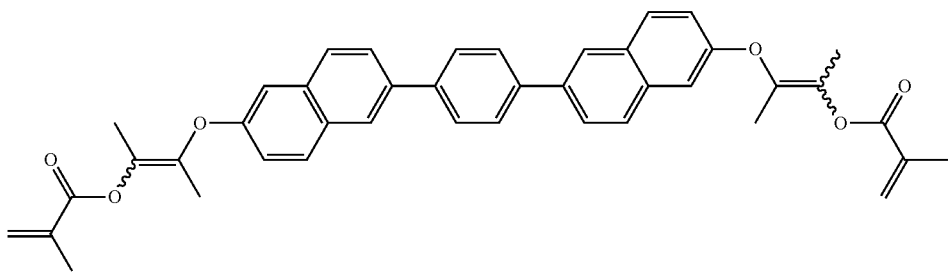
(No. 57)
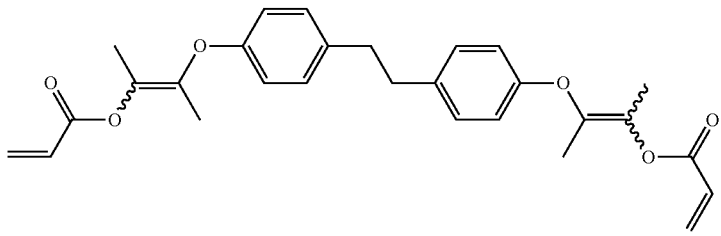
(No. 58)
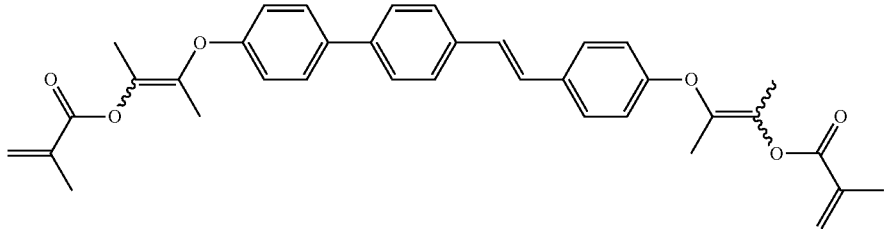
(No. 59)
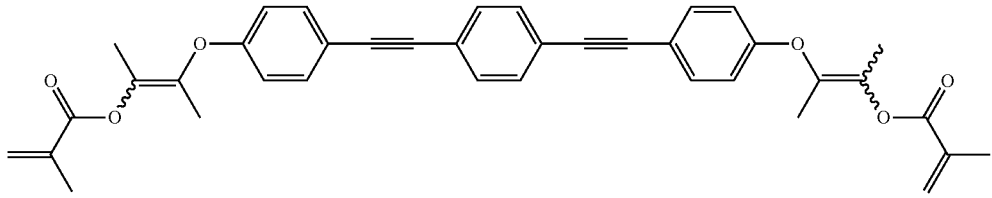
(No. 60)
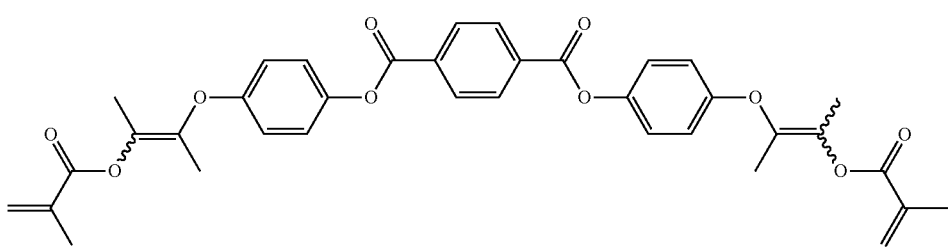

-continued

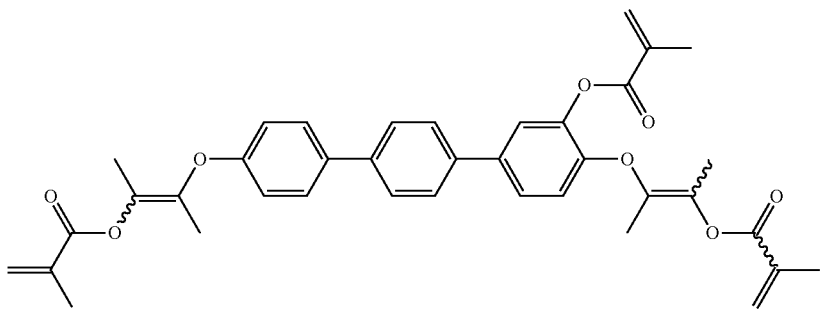
(No. 61)

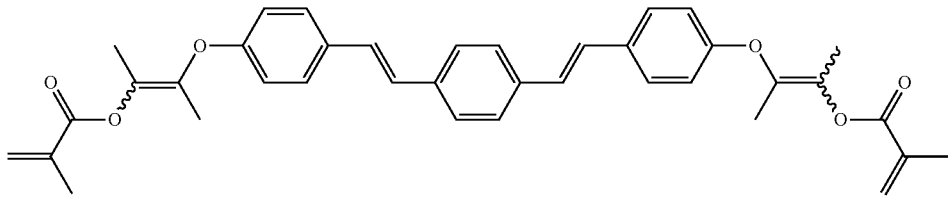
(No. 62)

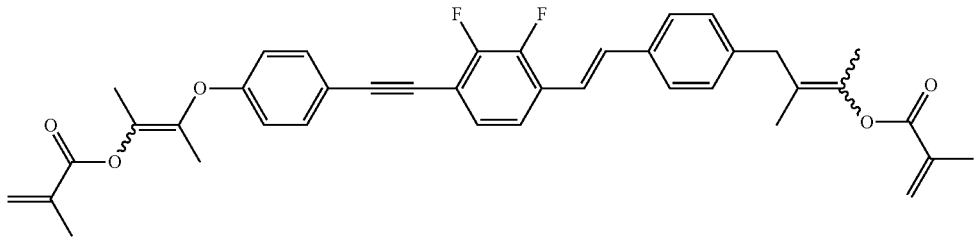
(No. 63)

Comparative Experiment 1

Quantitative Determination of an Unreacted Polymerizable Compound

Polymerizable compound (No. 8) was added to a liquid crystal composition at a ratio of 0.3% by weight and dissolved thereinto. The resulting polymerizable composition was irradiated with ultraviolet light having an intensity of 75 mW/cm$^2$ for 200 seconds (15,000 mJ) or 400 seconds (30,000 mJ). A mercury-xenon lamp, EXECURE4000-D, made by HOYA CANDEO OPTRONICS Corporation was used for irradiation of ultraviolet light. An amount of remaining polymerizable compound in the resulting liquid crystal composite was measured by HPLC. Meanwhile, an unreacted material was also measured on comparative compound (R-1) in a similar manner. The results are shown in Table 1.

TABLE 1

Comparison of amount of unreacted material

| Compound | Structural formula | Unreacted material (% by weight) | |
|---|---|---|---|
| | | 15,000 mJ | 30,000 mJ |
| Compound (No. 8) | | 38.7 | 2.0 |
| Comparative compound (R-1) | | 40.1 | 21.0 |

The amount of unreacted material (remaining polymerizable compound) in compound (No. 8) is smaller than the amount in the comparative compound. Therefore, compound (No. 8) is superior, compared with comparative compound (R-1) in the polymerization reactivity. The unreacted material in compound (No. 8) is significantly small, particularly in the case of irradiation with ultraviolet light of 30,000 mJ. More specifically, when compound (No. 8) was irradiated by a predetermined amount or more of ultraviolet light, significant high polymerization reactivity of the compound was found. In the both viewpoints of stability in storage and high polymerization reactivity, compound (No. 8) is preferred.

2. Example of Polymerizable Composition

Description of compounds in Examples were expressed using symbols as definitions in Table 2 below. In Table 2, a configuration of 1,4-cyclohexylene is trans. A parenthesized number on the right of a description of compound structure in Examples corresponds to the number of the compound. A symbol (-) means the other liquid crystal compound. A content (percentage) of a liquid crystal compound is expressed in ratio of weight percent (% by weight) based on the liquid crystal composition. Values of physical properties of the composition were summarized in a last part. The physical properties were measured in accordance with the methods described above, and measured values were directly described (without extrapolation).

TABLE 2

Method for Description of Compounds using Symbols
R—(A$_1$)—Z$_1$- · · · · -Z$_n$—(A$_n$)—R'

| | Symbol |
|---|---|
| 1) Left-terminal Group R- | |
| C$_n$H$_{2n+1}$— | n- |
| C$_n$H$_{2n+1}$O— | nO— |
| C$_m$H$_{2m+1}$OC$_n$H$_{2n}$— | mOn- |
| CH$_2$=CH— | V- |
| C$_n$H$_{2n+1}$—CH=CH— | nV- |
| CH$_2$=CH—C$_n$H$_{2n}$— | Vn- |
| C$_m$H$_{2m+1}$—CH=CH—C$_n$H$_{2n}$— | mVn- |
| CF$_2$=CH— | VFF— |
| CF$_2$=CH—C$_n$H$_{2n}$— | Vffn- |
| 2) Right-terminal Group -R' | |
| —C$_n$H$_{2n+1}$ | -n |
| —OC$_n$H$_{2n+1}$ | —On |
| —COOCH$_3$ | -EMe |
| —CH=CH$_2$ | -V |
| —CH=CH—C$_n$H$_{2n+1}$ | -Vn |
| —C$_n$H$_{2n}$—CH=CH$_2$ | -nV |
| —C$_m$H$_{2m}$—CH=CH—C$_n$H$_{2n+1}$ | -mVn |
| —CH=CF$_2$ | -VFF |
| —F | —F |
| —Cl | —CL |
| —OCF$_3$ | —OCF3 |
| —OCF$_2$H | —OCF2H |
| —CF$_3$ | —CF3 |
| —OCH=CH—CF$_3$ | —OVCF3 |
| —C≡N | —C |
| 3) Bonding Group -Z$_n$- | |
| —C$_n$H$_{2n}$— | n |
| —COO— | E |
| —CH=CH— | V |
| —CH$_2$O— | 1O |
| —OCH$_2$— | O1 |
| —CF$_2$O— | X |
| —C≡C— | T |

TABLE 2-continued

Method for Description of Compounds using Symbols
R—(A$_1$)—Z$_1$- · · · · -Z$_n$—(A$_n$)—R'

| | Symbol |
|---|---|
| 4) Ring Structure -A$_n$- | |
| (cyclohexylene) | H |
| (phenylene) | B |
| (phenylene with F) | B(F) |
| (phenylene with 2-F) | B(2F) |
| (phenylene with F,F) | B(F,F) |
| (phenylene with 2F,5F) | B(2F,5F) |
| (phenylene with 2F,3F) | B(2F,3F) |
| (pyrimidine) | Py |
| (dioxane) | G |
| (cyclohexenylene) | ch |

TABLE 2-continued

Method for Description of Compounds using Symbols
R—(A₁)—Z₁-· · · · ·-Zₙ—(Aₙ)—R'

Symbol

5) Examples of Description

Example 1. 3-HB-CL

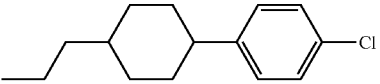 [SMILES: CCCC1CCC(c2ccc(Cl)cc2)CC1]

Example 2. 5-HHBB(F,F)-F

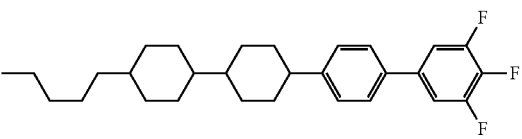 [SMILES: CCCCCC1CCC(C2CCC(c3ccc(-c4cc(F)c(F)c(F)c4)cc3)CC2)CC1]

Example 3. 3-HB-O2

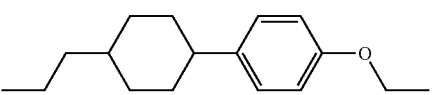 [SMILES: CCCC1CCC(c2ccc(OCC)cc2)CC1]

Example 4. 3-HBB(F,F)-F

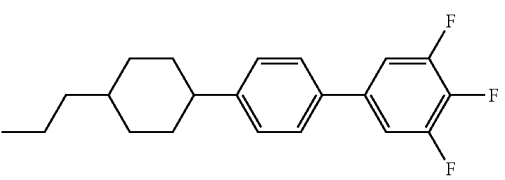 [SMILES: CCCC1CCC(c2ccc(-c3cc(F)c(F)c(F)c3)cc2)CC1]

Example 1

| | | |
|---|---|---|
| 3-HB—O2 | (2-5) | 7% |
| 5-HB—CL | (5-2) | 13% |
| 3-HBB(F, F)—F | (6-24) | 10% |
| 3-PyB(F)—F | (5-15) | 10% |
| 5-PyB(F)—F | (5-15) | 10% |
| 3-PyBB—F | (6-80) | 10% |
| 4-PyBB—F | (6-80) | 10% |
| 5-PyBB—F | (6-80) | 12% |
| 5-HBB(F)B-2 | (4-5) | 8% |
| 5-HBB(F)B-3 | (4-5) | 10% |

To the composition described above, compound (No. 10) was added at a ratio of 0.1% by weight.
NI=98.3° C.; η=40.8 mPa·s; Δn=0.192; Δ∈=8.5.

Example 2

| | | |
|---|---|---|
| 2-HB—C | (8-1) | 5% |
| 3-HB—C | (8-1) | 12% |
| 3-HB—O2 | (2-5) | 15% |
| 2-BTB-1 | (2-10) | 3% |
| 3-HHB—F | (6-1) | 4% |
| 3-HHB-1 | (3-1) | 8% |
| 3-HHB—O1 | (3-1) | 5% |
| 3-HHB-3 | (3-1) | 14% |
| 3-HHEB—F | (6-10) | 4% |
| 2-HHB(F)—F | (6-2) | 8% |
| 3-HHB(F)—F | (6-2) | 8% |
| 5-HHB(F)—F | (6-2) | 8% |
| 3-HHB(F, F)—F | (6-3) | 6% |

To the composition described above, compound (No. 21) was added at a ratio of 0.3% by weight.
NI=94.7° C.; η=15.1 mPa·s; Δn=0.097; Δ∈=4.8.

Example 3

| | | |
|---|---|---|
| 7-HB(F, F)—F | (5-4) | 4% |
| 3-HB—O2 | (2-5) | 6% |
| 2-HHB(F)—F | (6-2) | 10% |
| 3-HHB(F)—F | (6-2) | 10% |
| 5-HHB(F)—F | (6-2) | 10% |
| 2-HBB(F)—F | (6-23) | 10% |
| 3-HBB(F)—F | (6-23) | 10% |
| 5-HBB(F)—F | (6-23) | 14% |
| 2-HBB—F | (6-22) | 4% |
| 3-HBB—F | (6-22) | 4% |
| 5-HBB—F | (6-22) | 3% |
| 3-HBB(F, F)—F | (6-24) | 5% |
| 5-HBB(F, F)—F | (6-24) | 10% |

To the composition described above, compound (No. 17) was added at a ratio of 0.2% by weight.
NI=83.9° C.; η=25.2 mPa·s; Δn=0.114; Δ∈=5.7.

Example 4

| | | |
|---|---|---|
| 5-HB—CL | (5-2) | 16% |
| 3-HH-4 | (2-1) | 12% |
| 3-HH-5 | (2-1) | 5% |
| 3-HHB—F | (6-1) | 4% |
| 3-HHB—CL | (6-1) | 3% |
| 4-HHB—CL | (6-1) | 4% |
| 3-HHB(F)—F | (6-2) | 10% |
| 4-HHB(F)—F | (6-2) | 9% |
| 5-HHB(F)—F | (6-2) | 7% |
| 7-HHB(F)—F | (6-2) | 8% |
| 5-HBB(F)—F | (6-23) | 4% |
| 1O1—HBBH-5 | (4-1) | 3% |
| 3-HHBB(F, F)—F | (7-6) | 3% |
| 4-HHBB(F, F)—F | (7-6) | 3% |
| 5-HHBB(F, F)—F | (7-6) | 3% |
| 3-HH2BB(F, F)—F | (7-15) | 3% |
| 4-HH2BB(F, F)—F | (7-15) | 3% |

To the composition described above, compound (No. 8) was added at a ratio of 0.15% by weight.
NI=115.4° C.; η=19.6 mPa·s; Δn=0.091; Δ∈=3.8.

Example 5

| | | |
|---|---|---|
| 3-HHB(F, F)—F | (6-3) | 9% |
| 3-H2HB(F, F)—F | (6-15) | 8% |
| 4-H2HB(F, F)—F | (6-15) | 8% |
| 5-H2HB(F, F)—F | (6-15) | 8% |
| 3-HBB(F, F)—F | (6-24) | 20% |
| 5-HBB(F, F)—F | (6-24) | 20% |
| 3-H2BB(F, F)—F | (6-27) | 11% |
| 5-HHBB(F, F)—F | (7-6) | 3% |
| 5-HHEBB—F | (7-17) | 2% |
| 3-HH2BB(F, F)—F | (7-15) | 4% |
| 1O1—HBBH-4 | (4-1) | 3% |
| 1O1—HBBH-5 | (4-1) | 4% |

To the composition described above, compound (No. 10) was added at a ratio of 0.3% by weight.

NI=97.3° C.; η=35.0 mPa·s; Δn=0.116; Δ∈=9.1.

Example 6

| | | |
|---|---|---|
| 5-HB—F | (5-2) | 12% |
| 6-HB—F | (5-2) | 9% |
| 7-HB—F | (5-2) | 7% |
| 2-HHB—OCF3 | (6-1) | 8% |
| 3-HHB—OCF3 | (6-1) | 8% |
| 4-HHB—OCF3 | (6-1) | 7% |
| 5-HHB—OCF3 | (6-1) | 5% |
| 3-HH2B—OCF3 | (6-4) | 4% |
| 5-HH2B—OCF3 | (6-4) | 4% |
| 3-HHB(F, F)—OCF2H | (6-3) | 4% |
| 3-HHB(F, F)—OCF3 | (6-3) | 4% |
| 3-HH2B(F)—F | (6-5) | 3% |
| 3-HBB(F)—F | (6-23) | 9% |
| 5-HBB(F)—F | (6-23) | 10% |
| 5-HBBH-3 | (4-1) | 3% |
| 3-HB(F)BH-3 | (4-2) | 3% |

To the composition described above, compound (No. 21) was added at a ratio of 0.2% by weight.

NI=85.8° C.; η=14.5 mPa·s; Δn=0.092; Δ∈=4.4.

Example 7

| | | |
|---|---|---|
| 5-HB—CL | (5-2) | 11% |
| 3-HH-4 | (2-1) | 8% |
| 3-HHB-1 | (3-1) | 5% |
| 3-HHB(F, F)—F | (6-3) | 8% |
| 3-HBB(F, F)—F | (6-24) | 18% |
| 5-HBB(F, F)—F | (6-24) | 13% |
| 3-HHEB(F, F)—F | (6-12) | 13% |
| 4-HHEB(F, F)—F | (6-12) | 4% |
| 5-HHEB(F, F)—F | (6-12) | 3% |
| 2-HBEB(F, F)—F | (6-39) | 3% |
| 3-HBEB(F, F)—F | (6-39) | 5% |
| 5-HBEB(F, F)—F | (6-39) | 4% |
| 3-HHBB(F, F)—F | (7-6) | 5% |

To the composition described above, compound (No. 17) was added at a ratio of 0.35% by weight.

NI=80.8° C.; η=22.5 mPa·s; Δn=0.101; Δ∈=8.8.

Example 8

| | | |
|---|---|---|
| 3-HH-4 | (2-1) | 4% |
| 3-HHB-1 | (3-1) | 3% |
| 3-HHB—O1 | (3-1) | 5% |
| 3-HBB(F, F)—F | (6-24) | 30% |
| 5-HBB(F, F)—F | (6-24) | 25% |
| 3-HHB(F, F)—F | (6-3) | 4% |
| 3-H2HB(F, F)—F | (6-15) | 8% |
| 4-H2HB(F, F)—F | (6-15) | 10% |
| 5-H2HB(F, F)—F | (6-15) | 8% |
| 3-HHBB(F, F)—F | (7-6) | 3% |

To the composition described above, compound (No. 8) was added at a ratio of 0.15% by weight.

NI=75.1° C.; η=28.8 mPa·s; Δn=0.104; Δ∈=8.0.

Example 9

| | | |
|---|---|---|
| 3-HB—CL | (5-2) | 6% |
| 5-HB—CL | (5-2) | 4% |
| 3-HHB—OCF3 | (6-1) | 5% |
| 3-H2HB—OCF3 | (6-13) | 5% |
| 5-H4HB—OCF3 | (6-19) | 15% |
| V—HHB(F)—F | (6-2) | 5% |
| 3-HHB(F)—F | (6-2) | 6% |
| 5-HHB(F)—F | (6-2) | 6% |
| 3-H4HB(F, F)—CF3 | (6-21) | 8% |
| 5-H4HB(F, F)—CF3 | (6-21) | 10% |
| 5-H2HB(F, F)—F | (6-15) | 5% |
| 5-H4HB(F, F)—F | (6-21) | 7% |
| 2-H2BB(F)—F | (6-26) | 5% |
| 3-H2BB(F)—F | (6-26) | 8% |
| 3-HBEB(F, F)—F | (6-39) | 5% |

To the composition described above, compound (No. 10) was added at a ratio of 0.3% by weight.

NI=70.4° C.; η=25.2 mPa·s; Δn=0.096; Δ∈=8.3.

Example 10

| | | |
|---|---|---|
| 5-HB—CL | (5-2) | 17% |
| 7-HB(F, F)—F | (5-4) | 5% |
| 3-HH-4 | (2-1) | 9% |
| 3-HH-5 | (2-1) | 6% |
| 3-HB—O2 | (2-5) | 15% |
| 3-HHB-1 | (3-1) | 10% |
| 3-HHB—O1 | (3-1) | 5% |
| 2-HHB(F)—F | (6-2) | 6% |
| 3-HHB(F)—F | (6-2) | 7% |
| 5-HHB(F)—F | (6-2) | 7% |
| 3-HHB(F, F)—F | (6-3) | 5% |
| 3-H2HB(F, F)—F | (6-15) | 4% |
| 4-H2HB(F, F)—F | (6-15) | 4% |

To the composition described above, compound (No. 21) was added at a ratio of 0.1% by weight.

NI=70.1° C.; η=12.9 mPa·s; Δn=0.073; Δ∈=2.6.

Example 11

| | | |
|---|---|---|
| 5-HB—CL | (5-2) | 3% |
| 7-HB(F)—F | (5-3) | 5% |
| 3-HH-4 | (2-1) | 8% |
| 3-HH—EMe | (2-2) | 23% |
| 3-HHEB—F | (6-10) | 10% |
| 5-HHEB—F | (6-10) | 9% |
| 3-HHEB(F, F)—F | (6-12) | 10% |
| 4-HHEB(F, F)—F | (6-12) | 5% |
| 4-HGB(F, F)—F | (6-103) | 5% |
| 5-HGB(F, F)—F | (6-103) | 6% |
| 2-H2GB(F, F)—F | (6-106) | 4% |
| 3-H2GB(F, F)—F | (6-106) | 5% |
| 5-GHB(F, F)—F | (6-109) | 7% |

To the composition described above, compound (No. 17) was added at a ratio of 0.4% by weight.

NI=84.3° C.; η=21.1 mPa·s; Δn=0.066; Δ∈=5.8.

Example 12

| | | |
|---|---|---|
| 1V2—BEB(F, F)—C | (8-15) | 5% |
| 3-HB—C | (8-1) | 15% |

-continued

| | | |
|---|---|---|
| 2-BTB-1 | (2-10) | 10% |
| 5-HH—VFF | (2-1) | 28% |
| 3-HHB-1 | (3-1) | 6% |
| VFF—HHB-1 | (3-1) | 9% |
| VFF2—HHB-1 | (3-1) | 11% |
| 3-H2BTB-2 | (3-17) | 6% |
| 3-H2BTB-3 | (3-17) | 5% |
| 3-H2BTB-4 | (3-17) | 5% |

To the composition described above, compound (No. 8) was added at a ratio of 0.15% by weight.
NI=88.6° C.; η=11.9 mPa·s; Δn=0.134; Δ∈=5.6.

Example 13

| | | |
|---|---|---|
| 5-HB(F)B(F, F)XB(F, F)—F | (7-41) | 5% |
| 3-BB(F)B(F, F)XB(F, F)—F | (7-47) | 4% |
| 4-BB(F)B(F, F)XB(F, F)—F | (7-47) | 7% |
| 5-BB(F)B(F, F)XB(F, F)—F | (7-47) | 4% |
| 3-HH—V | (2-1) | 38% |
| 3-HH—V1 | (2-1) | 7% |
| 3-HHEH-5 | (3-13) | 4% |
| 3-HHB-1 | (3-1) | 4% |
| V—HHB-1 | (3-1) | 5% |
| V2—BB(F)B-1 | (3-6) | 5% |
| 1V2—BB—F | (5-1) | 3% |
| 3-BB(F, F)XB(F, F)—F | (6-97) | 11% |
| 3-HHBB(F, F)—F | (7-6) | 3% |

To the composition described above, compound (No. 10) was added at a ratio of 0.2% by weight.
NI=83.9° C.; η=14.8 mPa·s; Δn=0.109; Δ∈=7.0.

Example 14

| | | |
|---|---|---|
| 3-GB(F)B(F, F)XB(F, F)—F | (7-57) | 5% |
| 5-HB(F)B(F, F)XB(F, F)—F | (7-41) | 4% |
| 3-BB(F)B(F, F)XB(F, F)—F | (7-47) | 5% |
| 4-BB(F)B(F, F)XB(F, F)—F | (7-47) | 7% |
| 5-BB(F)B(F, F)XB(F, F)—F | (7-47) | 3% |
| 3-HH—V | (2-1) | 36% |
| 3-HH—V1 | (2-1) | 7% |
| 3-HHEH-5 | (3-13) | 4% |
| 3-HHB-1 | (3-1) | 4% |
| V—HHB-1 | (3-1) | 5% |
| V2—BB(F )B-1 | (3-6) | 5% |
| 1V2—BB—F | (5-1) | 3% |
| 3-BB(F, F)XB(F, F)—F | (6-97) | 5% |
| 3-GB(F, F)XB(F, F)—F | (6-113) | 4% |
| 3-HHBB(F, F)—F | (7-6) | 3% |

To the composition described above, compound (No. 21) was added at a ratio of 0.3% by weight.
NI=86.4° C.; η=17.8 mPa·s; Δn=0.110; Δ∈=8.6.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

A liquid crystal display device having a mode such as a PSA mode can be prepared by polymerizing a polymerizable composition containing polymerizable compound (1) and a liquid crystal composition. The liquid crystal display device has properties of a wide temperature range in which the device can be used, a short response time, a high voltage holding ratio, a low threshold voltage, a large contrast ratio and a long service life. Accordingly, compound (1) can be used for a liquid crystal projector, a liquid crystal television or the like. Compound (1) can also be used as a raw material of an optically anisotropic body.

What is claimed is:

1. A polymerizable compound represented by formula (1):

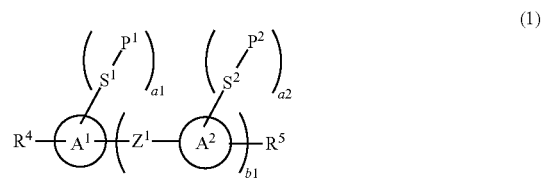

(1)

wherein, in formula (1),
$P^1$ and $P^2$ are independently a polymerizable group;
$S^1$ and $S^2$ are independently a single bond or alkylene having 1 to 10 carbons, in the alkylene, at least one of —$CH_2$— may be replaced by —O—, —CO—, —COO— or —OCO—, at least one of —$CH_2$—$CH_2$— may be replaced by —CH=CH— or —C≡C—, and in the divalent groups, at least one of hydrogen may be replaced by halogen or alkyl having 1 to 3 carbons;
$R^4$ is hydrogen or —$S^1$—$P^1$, and $R^5$ is hydrogen or —$S^2$—$P^2$;
a1 and a2 are independently 0, 1, 2, 3 or 4; and
a total of —$S^1$—$P^1$ and —$S^2$—$P^2$ is 2 to 8, and at least one of all of —$S^1$—$P^1$ and all of —$S^2$—$P^2$ is a monovalent group represented by formula (A):

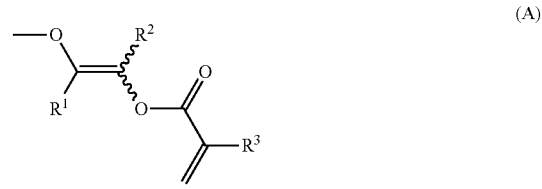

(A)

wherein, in formula (A), $R^1$ and $R^2$ are independently alkyl having 1 to 3 carbons, and $R^3$ is hydrogen or methyl; and
in formula (1),
ring $A^1$ and ring $A^2$ are independently a divalent group derived from alicyclic hydrocarbon having 3 to 18 carbons, aromatic hydrocarbon having 6 to 18 carbons or heteroaromatic hydrocarbon having 3 to 18 carbons, in the divalent groups, at least one of hydrogen may be replaced by halogen, alkyl having 1 to 12 carbons, alkoxy having 1 to 12 carbons, alkenyl having 1 to 12 carbons or alkenyloxy having 1 to 12 carbons, and in the monovalent hydrocarbon groups, at least one of hydrogen may be replaced by halogen;
$Z^1$ is a single bond or alkylene having 1 to 10 carbons, in the alkylene, at least one of —$CH_2$— may be replaced by —O—, —CO—, —COO— or —OCO—, at least one of —$CH_2$—$CH_2$— may be replaced by —CH=CH—, —C($CH_3$)=CH—, —CH=C($CH_3$)—, —C($CH_3$)=C($CH_3$)— or —CH≡CH—, and in the divalent groups, at least one of hydrogen may be replaced by halogen; and b1 is 0, 1, 2 or 3.

2. The polymerizable compound according to claim 1, represented by formula (1), wherein, in formula (1), $P^1$ and $P^2$ are independently acryloyloxy or methacryloyloxy;

$S^1$ and $S^2$ are independently a single bond or alkylene having 1 to 4 carbons, in the alkylene, at least one of —$CH_2$— may be replaced by —O—, at least one of —$CH_2$—$CH_2$— may be replaced by —CH=CH— or —C≡C—, and in the divalent groups, at least one of hydrogen may be replaced by fluorine or alkyl having 1 to 3 carbons;

a1 and a2 are independently 0, 1, 2 or 3; and a total of —$S^1$—$P^1$ and —$S^2$—$P^2$ is 2 to 6, and at least one of all of —$S^2$—$P^1$ and all of —$S^2$—$P^2$ is a monovalent group represented by formula (A):

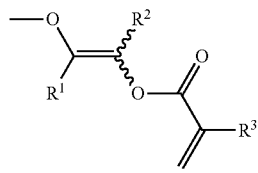

(A)

wherein, in formula (A), $R^1$ and $R^2$ are methyl, and $R^3$ is hydrogen or methyl; and in formula (1), ring $A^1$ and ring $A^2$ are independently a divalent group derived from aromatic hydrocarbon having 6 to 18 carbons or heteroaromatic hydrocarbon having 3 to 18 carbons, in the divalent groups, at least one of hydrogen may be replaced by fluorine, chlorine, alkyl having 1 to 4 carbons, alkoxy having 1 to 4 carbons, alkenyl having 1 to 4 carbons or alkenyloxy having 1 to 4 carbons, and in the monovalent hydrocarbon groups, at least one of hydrogen may be replaced by fluorine or chlorine;

$Z^1$ is a single bond or alkylene having 1 to 4 carbons, in the alkylene, at least one of —$CH_2$— may be replaced by —O—, —CO—, —COO— or —OCO—, and at least one of —$CH_2$—$CH_2$— may be replaced by —CH=CH—, —C($CH_3$)=CH—, —CH=C($CH_3$)—, —C($CH_3$)=C($CH_3$)— or —CH≡CH—, and in the divalent groups, at least one of hydrogen may be replaced by fluorine or chlorine; and b1 is 0, 1 or 2.

3. The polymerizable compound according to claim 2, represented by formula (1-1):

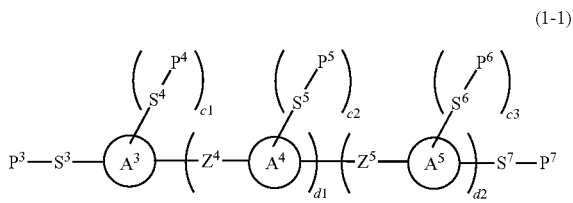

(1-1)

wherein, in formula (1-1), $P^3$, $P^4$, $P^5$, $P^6$ and $P^7$ are independently acryloyloxy or methacryloyloxy;

$S^3$, $S^4$, $S^5$, $S^6$ and $S^7$ are independently a single bond or alkylene having 1 to 4 carbons, in the alkylene, at least one of —$CH_2$— may be replaced by —O—, at least one of —$CH_2$—$CH_2$— may be replaced by —CH=CH— or —C≡C—, and in the divalent groups, at least one of hydrogen may be replaced by fluorine, methyl or ethyl;

c1, c2 and c3 are independently 0, 1 or 2, and a sum of c1, d1 pieces of c2 for each c2 and d2 pieces of c3 for each c3 is 0, 1 or 2; and at least one of —$S^3$—$P^3$, of all of —$S^4$—$P^4$, all of —$S^5$—$P^5$, all of —$S^6$—$P^6$ and —$S^7$—$P^7$ is a monovalent group represented by formula (A):

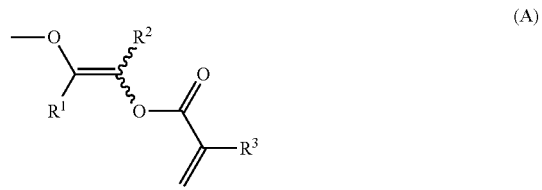

(A)

wherein, in formula (A), $R^1$ and $R^2$ are methyl, and $R^3$ is hydrogen or methyl; and in formula (1-1), ring $A^3$, ring $A^4$ and ring $A^5$ are independently 1,4-phenylene, naphthalene-1,4-diyl, naphthalene-1,5-diyl, naphthalene-2,6-diyl, fluorene-2,7-diyl or phenanthrene-2,7-diyl, and in the rings, at least one of hydrogen may be replaced by fluorine, alkyl having 1 to 3 carbons, and alkyl having 1 to 3 carbons in which at least one of hydrogen was replaced by fluorine or chlorine;

$Z^4$ and $Z^5$ are independently a single bond, alkylene having 1 to 4 carbons, —COO—, —OCO—, —$CH_2$O—, —O$CH_2$—, —$CF_2$O—, —O$CF_2$—, —CH=CH—, —CH=CH—COO—, —OCO—CH=CH—, —C($CH_3$)=CH—COO—, —OCO—CH=C($CH_3$)—, —CH=C($CH_3$)—COO—, —OCO—($CH_3$)C=CH—, —C($CH_3$)=C($CH_3$)—COO—, —OCO—C($CH_3$)=C($CH_3$)—, —CO—CH=CH—, —CH=CH—CO—, —C($CH_3$)=C($CH_3$)—, —CH=CH—$CH_2$O—, —O$CH_2$—CH=CH—, —CH=CH—O$CH_2$—, —$CH_2$O—CH=CH— or —CH≡CH—; and d1 and d2 are independently 0 or 1.

4. The polymerizable compound according to claim 3, represented by formula (1-1), wherein, in formula (1-1), $P^3$, $P^4$, $P^5$, $P^6$ and $P^7$ are independently acryloyloxy or methacryloyloxy;

$S^3$, $S^4$, $S^5$, $S^6$ and $S^7$ are independently a single bond or —OC($CH_3$)=C($CH_3$);

c1, c2 and c3 are independently 0, 1 or 2, and a sum of c1, d1 pieces of c2 for each c2 and d2 pieces of c3 for each c3 is 0, 1 or 2; and at least one of —$S^3$—$P^3$, of all of —$S^4$—$P^4$, all of —$S^5$—$P^5$, all of —$S^6$—$P^6$ and —$S^7$—$P^7$ is a monovalent group represented by formula (A):

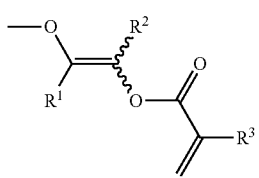

(A)

wherein, in formula (A), $R^1$ and $R^2$ are methyl, and $R^3$ is hydrogen or methyl; and in formula (1-1),
 ring $A^3$, ring $A^4$ and ring $A^5$ are independently 1,4-phenylene, naphthalene-1,4-diyl, naphthalene-1,5-diyl, naphthalene-2,6-diyl, fluorene-2,7-diyl or phenanthrene-2,7-diyl, and in the rings, at least one of hydrogen may be replaced by fluorine, methyl or trifluoromethyl;
 $Z^4$ and $Z^5$ are independently a single bond, ethylene, —COO—, —OCO—, —CH=CH—, —CH=CH—COO—, —OCO—CH=CH— or —C≡C—; and
 d1 and d2 are independently 0 or 1.

5. The polymerizable compound according to claim 4, represented by formulas (1-1-1) to (1-1-3):

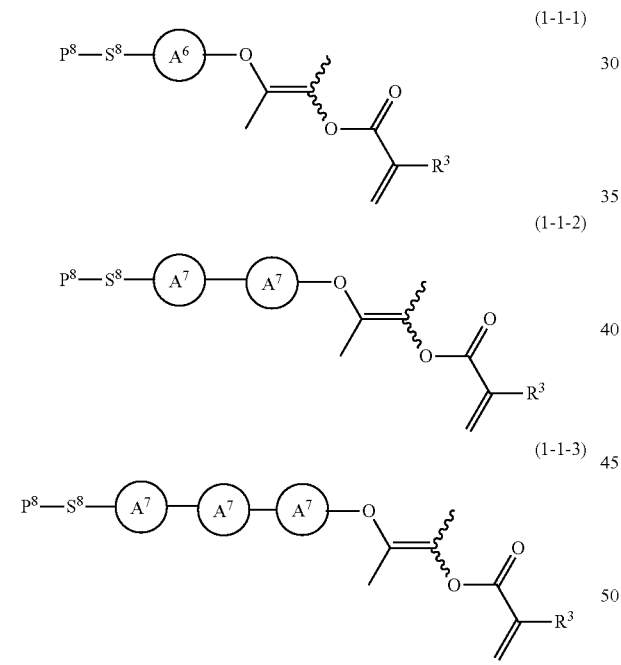

(1-1-1)

(1-1-2)

(1-1-3)

wherein, in formulas (1-1-1) to (1-1-3), $P^8$ is acryloyloxy or methacryloyloxy; $S^8$ is a single bond or —OC(CH$_3$)=C(CH$_3$)—; ring $A^6$ is naphthalene-1,4-diyl, naphthalene-2,6-diyl, fluorene-2,7-diyl or phenanthrene-2,7-diyl; ring $A^7$ is 1,4-phenylene in which at least one of hydrogen may be replaced by fluorine or methyl, naphthalene-1,4-diyl or naphthalene-2,6-diyl; and $R^3$ is hydrogen or methyl.

6. A polymerizable composition, containing at least one polymerizable compound according to claim 1.

7. The polymerizable composition according to claim 6, further containing at least one compound selected from the group of compounds represented by formulas (2) to (4):

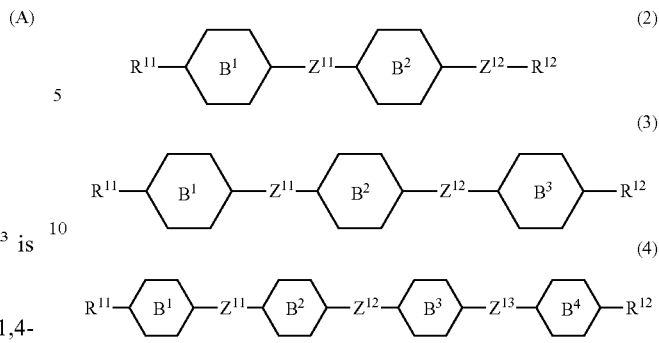

(2)

(3)

(4)

wherein, in formulas (2) to (4),
 $R^{11}$ and $R^{12}$ are independently alkyl having 1 to 10 carbons or alkenyl having 2 to 10 carbons, and in the alkyl or the alkenyl, at least one of —CH$_2$— may be replaced by —O—, and at least one of hydrogen may be replaced by fluorine;
 ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and
 $Z^{11}$, $Z^{12}$ and $Z^{13}$ are independently a single bond, —CH$_2$CH$_2$—, —CH=CH—, —C≡C— or —COO—.

8. The polymerizable composition according to claim 6, further containing at least one compound selected from the group of compounds represented by formulas (5) to (7):

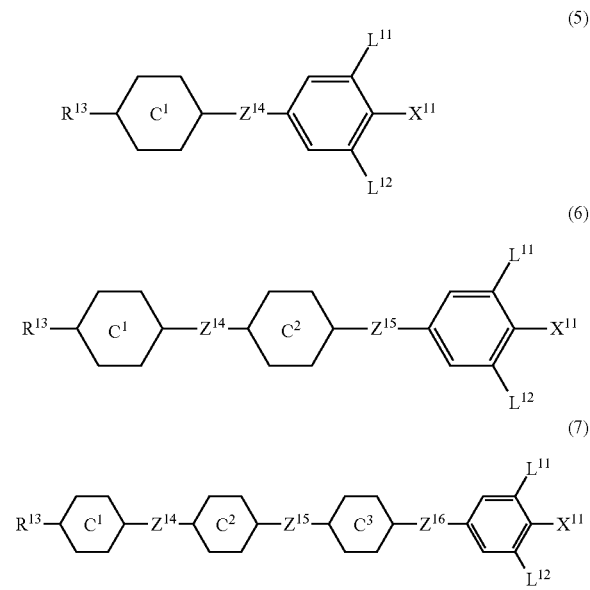

(5)

(6)

(7)

wherein, in formulas (5) to (7),
 $R^{13}$ is alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine;
 $X^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;
 ring $C^1$, ring $C^2$ and ring $C^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

9. The polymerizable composition according to claim 6, further containing at least one compound selected from the group of compounds represented by formula (8):

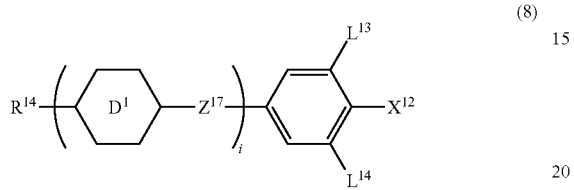

(8)

wherein, in formula (8), $R^{14}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$X^{12}$ is —C≡N or —C≡C—C≡N;

ring $D^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{17}$ is a single bond, —$CH_2CH_2$—, —C≡C—, —COO—, —$CF_2O$—, —$OCF_2$— or —$CH_2O$—;

$L^{13}$ and $L^{14}$ are independently hydrogen or fluorine; and i is 1, 2, 3 or 4.

10. A liquid crystal display device, including the polymerizable composition according to any one of claims 6 to 9.

* * * * *